US008278313B2

(12) United States Patent
Liu et al.

(10) Patent No.: US 8,278,313 B2
(45) Date of Patent: Oct. 2, 2012

(54) MACROCYCLIC SPIRO PYRIMIDINE DERIVATIVES

(75) Inventors: Huaqing Liu, Buffalo Grove, IL (US); John R. Koenig, Chicago, IL (US); Marlon D. Cowart, Round Lake Beach, IL (US); Lawrence A. Black, Libertyville, IL (US)

(73) Assignee: Abbott Laboratories, Abbott Park, IL (US)

(*) Notice: Subject to any disclaimer, the term of this patent is extended or adjusted under 35 U.S.C. 154(b) by 256 days.

(21) Appl. No.: 12/401,385

(22) Filed: Mar. 10, 2009

(65) Prior Publication Data
US 2009/0233904 A1 Sep. 17, 2009

Related U.S. Application Data

(60) Provisional application No. 61/035,440, filed on Mar. 11, 2008.

(51) Int. Cl.
*A61K 31/517* (2006.01)
(52) U.S. Cl. .................... 514/266.2; 544/283
(58) Field of Classification Search ........... 544/283
See application file for complete search history.

(56) References Cited

U.S. PATENT DOCUMENTS

| | | | |
|---|---|---|---|
| 2,932,650 A | 4/1960 | Cope et al. | |
| 3,247,206 A | 4/1966 | Yost et al. | |
| 5,071,999 A | 12/1991 | Schenke et al. | |
| 5,252,747 A | 10/1993 | Chu et al. | |
| 5,442,044 A | 8/1995 | Hoover et al. | |
| 7,135,476 B2 * | 11/2006 | Clark .................... | 514/267 |
| 2005/0084446 A1 | 4/2005 | Schmitt et al. | |
| 2005/0101602 A1 | 5/2005 | Basha et al. | |
| 2006/0019985 A1 | 1/2006 | Ma et al. | |
| 2008/0194538 A1 | 8/2008 | Cowart et al. | |

FOREIGN PATENT DOCUMENTS

| | | |
|---|---|---|
| DE | 3726908 A1 | 2/1989 |
| EP | 0202062 | 11/1986 |
| JP | 2001039950 | 2/2001 |
| WO | WO9203415 | 3/1992 |
| WO | WO9510519 | 4/1995 |
| WO | WO9623782 | 8/1996 |
| WO | WO9921855 | 5/1999 |
| WO | WO9940070 | 8/1999 |
| WO | WO0170673 | 9/2001 |
| WO | WO0230890 A1 | 4/2002 |
| WO | WO2004056784 | 7/2004 |
| WO | WO2004103992 A1 | 12/2004 |
| WO | WO2005040159 A1 | 5/2005 |
| WO | WO2005040167 A1 | 5/2005 |
| WO | WO2005054239 A1 | 6/2005 |
| WO | WO2005082854 A1 | 9/2005 |
| WO | WO2005082855 A1 | 9/2005 |
| WO | WO2005097794 A1 | 10/2005 |
| WO | WO2006021544 A1 | 3/2006 |
| WO | WO2006040281 | 4/2006 |
| WO | WO2006048750 A2 | 5/2006 |
| WO | WO2006050965 A1 | 5/2006 |
| WO | WO2007072163 A2 | 6/2007 |

OTHER PUBLICATIONS

Akdis, et al., "Histamine Receptors Are Hot in Immunopharmacology," European Journal of Pharmacology, 2006, vol. 533, pp. 69-76.
Anquetin, et al., "Design, Synthesis and Activity Against Toxoplasma Gondii, Plasmodium Spp., and Mycobacterium Tuberculosis of New 6-fluoroquinolones," European Journal of Medicinal Chemistry, 2006, vol. 41 (12), pp. 1478-1493.
Baas, et al., "Vitamin A Analogues. IV. Attempted Synthesis of 2,4,4-trimethyl-tetrahydrothiopyrone-3," Tetrahedron, 1966, vol. 22 (1), pp. 285-291.
Becker, et al., "A Short Synthesis of 1-Azaadamantan-4-One and the 4r and 4s Isomers of 4-Amino-1-Azaadamantane," Synthesis, 1992, vol. 11, pp. 1080-1082.
Bell, et al., "Involvement of Histamine H4 and H1 Receptors in Scratching Induced by Histamine Receptor Agonists in Balb C Mice," British Journal of Pharmacology, 2004, vol. 142, pp. 374-380.
Bennett, et al., "A Peripheral Mononeuropathy in Rat that Produces Disorders of Pain Sensation like those Seen in Man," Pain, 1988, vol. 33 (1), pp. 87-107.
Bergmann, et al., "High Yields of Diazabicycloalkanes and Oxazabicycloalkanes Containing Medium and Large Rings From Rhodium-Catalysed Hydroformylation Reactions Without the Need for High Dilution Conditions," Chemical Communications, 1999, vol. 14, pp. 1279-1280. Buckland, et al., "Histamine Induces Cytoskeletal Changes in Human Eosinophils via the H(4) Receptor," British Journal of Pharmacology, 2003, vol. 140, pp. 1117-1127.
Chaplan, et al., "Quantitative Assessment of Tactile Allodynia in the Rat Paw," Journal of Neuroscience Methods, 1994, vol. 53, pp. 55-63.
Cianchi, et al., "The role of Cyclooxygenase-2 in Mediating the Effects of Histamine on Cell Proliferation and Vascular Endothelial Growth Factor Production in Colorectal Cancer," Clinical Cancer Research, 2005, vol. 11 (19), pp. 6807-6815.
Coge, et al., "Structure and Expression of the Human Histamine H4-Receptor Gene," Biochemical and Biophysical Research Communications, 2001, vol. 284 (2), pp. 301-309.
Collins, et al., "Emerging Therapies for Neuropathic Pain," Expert Opinion on Emerging Drugs, 2005, vol. 10 (1), pp. 95-108.
Coruzzi, et al., "Anti-Inflammatory and Antinociceptive Effects of the Selective Histamine H4-Receptor Antagonists JNJ7777120 and VUF6002 in a Rat Model of Carrageenan-Induced Acute Inflammation," European Journal of Pharmacology, 2007, vol. 563 (1-3), pp. 240-244.

(Continued)

*Primary Examiner* — James O Wilson
*Assistant Examiner* — Brian McDowell
(74) *Attorney, Agent, or Firm* — Nancy J. Gettel; Portia Chen

(57) ABSTRACT

Macrocyclic Spiro pyrimidine compounds of formula (I):

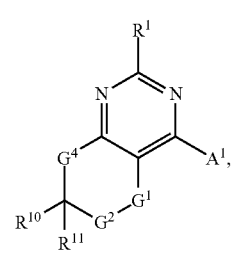

compositions comprising such compounds, methods for making the compounds, and methods of treating and preventing the progression of diseases, conditions, and disorders using such compounds and compositions are described herein.

6 Claims, No Drawings

OTHER PUBLICATIONS

Coruzzi, et al., 35th Meeting of the European Histamine Research Society in Delphi, Greece (May 10-13, 2006) presentation O44.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Culbertson, et al., "Quinolone Antibacterial Agents Substituted at the 7-position With Spiroamines. Synthesis and Structure-Activity Relationships," Journal of Medicinal Chemistry, 1990, vol. 33 (8), pp. 2270-2275.
De Esch, et al., "The Histamine H4 Receptor as a New Therapeutic Target for Inflammation," Trends in Pharmacological Science, 2005, vol. 26 (9), pp. 462-469.
Dixon, "Efficient Analysis of Experimental Observations," Annual Review of Pharmacology and Toxicology, 1980, vol. 20, pp. 441-462.
Dray, et al., "Pharmacology of Chronic Pain," Trends in Pharmacological Sciences, 1994, vol. 15 (6), pp. 190-197.
Dunford, et al., "The Histamine H4 Receptor Mediates Allergic Airway Inflammation by Regulating the Activation of CD4+ T cells," The Journal of Immunology, 2006, vol. 176 (11), pp. 7062-7070.
Dworkin, "An Overview of Neuropathic Pain: Syndromes, Symptoms, Signs, and Several Mechanisms," Clinical Journal of Pain, 2002, vol. 18 (6), pp. 343-349.
Esbenshade, et al., "Pharmacological and Behavioral Properties of A-349821, a Selective and Potent Human Histamine H3 Receptor Antagonist," Biochemical Pharmacology, 2004, vol. 68 (5), pp. 933-945.
Fogel, et al., "Influence of H3/H4 Receptor Antagonist Thioperamide on Regional Haemodynamics in Rats with Trinitrobenzene Sulfonic Acid-Induced Colitis 35th Meeting of the European Histamine Research Society in Delphi, Greece," 2006, pp. 32.
Frohlich, et al. "A Novel Synthesis of 3,3-(Spiro)Substituted Azetidines" Heterocycles, 1994, vol. 37 (3), pp. 1879-1891.
Furniss, et al., Vogel's Textbook of Practical Organic Chemistry, 5th Edition, Longman Scientific & Technical, 1989, Table of Contents.
Grzybowska-Kowalczyk, et al., "Distribution Pattern of Histamine H4 Receptor in Human Synovial Tissue from Patients with Rheumatoid Arthritis," Inflammation Research, 2007, vol. 56 (Suppl. 1), pp. S59-S60.
Gutzmer, et al., "Histamine H4 Receptor Stimulation Suppresses IL-12p70 Production and Mediates Chemotaxis in Human Monocyte-derived Dendritic Cells," Journal of Immunology, 2005, vol. 174 (9), pp. 5224-5232.
Hanus, et al., "Stereoelectronic Effects on the Fragmentation of 2,9-Diazabicyclo[4.4.0]Decame Derivatives," 1984, vol. 19 (9), pp. 459-460.
Higuchi, et al., "Pro-Drugs as Novel Drug Delivery Systems," American Chemical Society, 1975, Table of Contents.
Honore, et al., "Interleukin-1 alphabeta Gene-Deficient Mice Show Reduced Nociceptive Sensitivity in Models of Inflammatory and Neuropathic Pain but not Post-operative Pain," Behavioral Brain Research, 2006, vol. 167 (2), pp. 355-364.
Horner, et al., "Zur Kenntnis Der Elektroreduktiven Spaltungder N-N-Bindung 2," Justus Liebigs Annalen der Chemie, 1978, vol. 9, pp. 1505-1517.
Ikawa, et al., "Histamine H4 Receptor Expression in Human Synovial Cells Obtained from Patients Suffering from Rheumatoid Arthritis," Biological and Pharmaceutical Bulletin, 2005, vol. 28 (10), pp. 2016-2018.
International Search Report for Application No. PCT/US2009/036728, mailed on Jun. 22, 2009, 2 pages.
Iselin, et al., "A New Synthesis of 2,7"-Naphthyridine Derivatives," Journal of the American Chemical Society, 1954, vol. 76, pp. 3220-3222.
Joshi, et al., "Animal Models of Pain for Drug Discovery," Expert Opinion on Drug Discovery, 2006, vol. 1 (4), pp. 323-334.
Joshi, et al., "Involvement of the TTX-resistant Sodium Channel Nav 1.8 in Inflammatory and Neuropathic, but not Post-operative, Pain States," Pain, 2006, vol. 123 (1-2), pp. 75-82.
Kemp, et al., "Synthetic Routes to 1,5-Diazacyclooctanes via 2,6-Diketo- 1,5-diazabicyclo[3.3.]octanes," Journal of Organic Chemistry, 1979, vol. 44 (25), pp. 4473-4476.
Kim, et al., "An Experimental Model for Peripheral Neuropathy Produced by Segmental Spinal Nerve Ligation in the Rat," Pain, 1992, vol. 50 (3), pp. 355-363.
Kobashi, et al., "Structure Activity Relation Study of Matrine-type Alkaloids. Part III," Yakugaku Zasshi, 2003, vol. 123 (5), pp. 337-347.
Krivdin, et al., "13C-13C Coupling Constants in Structural Studies: XXXII. Additivity of Spin-Spin Couplings in Sterically Strained Heterocycles," Russian Journal of Organic Chemistry, 2003, vol. 39 (5), pp. 698-704.
Krueger, et al., "G Protein-Dependent Pharmacology of Histamine H3 Receptor Ligands: Evidence for Heterogeneous Active State Receptor Conformations," Journal of Pharmacology and Experimental Therapeutics, 2005, vol. 314 (1), pp. 271-281.
Lazar-Molnar, "Signal-Transduction Pathways of Histamine Receptors" in: Histamine: Biology and Medical Aspects, Falus A., et al., eds., Spring Med Publishing Ltd., 2004, pp. 89-96.
Li, et al., "A Practical Stereoselective Synthesis of (2S, 4S)- 4-tert-Butoxycarbonylamino-2-Methylpyrrolidine 1," Tetrahedron Letters, 1995, vol. 36 (46), pp. 8391-8394.
Li, et al., "Synthesis and Structure-activity Relationships of 2-pyridones: a Novel Series of Potent DNA Gyrase Inhibitors as Antibacterial Agents," Journal of Medicinal Chemistry, 1996, vol. 39 (16), pp. 3070-3088.
Li, et al., "Synthesis and Structure-activity Relationships of 2-pyridones: II. 8-(Fluoro-substituted pyrrolidinyl)-2-pyridones as Antibacterial Agents," Bioorganic and medicinal chemistry letters, 1998, vol. 8 (15), pp. 1953-1958.
Li, et al., "Enantioselective Oxidative Biaryl Coupling Reactions Catalyzed by 1,5-Diazadecalin Metal Complexes: Efficient Formation of Chiral Functionalized BINOL Derivatives," Journal of Organic Chemistry, 2003, vol. 68 (14), pp. 5500-5511.
Linden, et al., "Dispiro[fluorene-9,5"-[1,2,3,4]tetrathiane-6",9"-fluorene," Acta Crystallographica Section C, 2001, vol. 57 (Pt 6), pp. 764-766.
Liu, et al., "Cloning and Pharmacological Characterization of a Fourth Histamine Receptor (H4) Expressed in Bone Marrow," Molecular Pharmacology, 2001, vol. 59, pp. 420-426.
Liu, et al., "Comparison of Human, Mouse, Rat, and Guinea Pig Histamine H4 Receptors Reveals Substantial Pharmacological Species Variation," Journal of Pharmacology and Experimental Therapeutics, 2001, vol. 299, pp. 121-130.
Maffei, et al., "Silvio Maffei e Silvio Pietra.—Idrogenazione di alcune fenazine e chinossaline," Gazzetta Chimica Italiana, 1958, vol. 88, pp. 556-563.
Maslinska, et al., Toll-like Receptors (TLRs) and Histamine Receptor H4 in Articular Tissues of Patients with Rheumatoid Arthritis (RA), 34th Meeting of the European Histamine Research Society in Bled, Slovenia, 2005, Poster P-03.
Murahashi, et al., "Catalytic Alkyl Group Exchange Reaction of Primary and Secondary Amines," Journal of the American Chemical Society, 1983, vol. 105, pp. 5002-5011.
Nguyen, et al., "Discovery of a Novel Member of the Histamine Receptor Family," Molecular Pharmacology, 2001, vol. 59 (3), pp. 427-433.
Oda, et al., "Molecular Cloning of Monkey Histamine H4 Receptor," Journal of Pharmacological Sciences, 2005, vol. 98 (3), pp. 319-322.
Parsons, et al., "Histamine and its Receptors," British Journal of Pharmacology, 2006, vol. 147 Suppl 1, pp. 5127-5135.
Ponomarev, et al., "1-(alpha-furyl)-5-methyl-3-aminohexane," Metody Polucheniya Khimicheskikh Reaktivov i Preparativ, 1967, vol. 17, pp. 165-166.
Porreca, et al., "Antinociceptive Pharmacology of N-[[4-(4,5-Dihydro-1 H-imidazol-2-yl)phenylmethyl]-242-[[(4- methoxy-2,6-dimethylphenyl)sulfonyl]methylanninojethoxyl-N-methylacetamide, Fumarate (LF22-0542), a Novel Nonpeptidic Bradykinin B1 Receptor Antagonist," Journal of Pharmacology and Experimental Therapeutics, 2006, vol. 318, pp. 195-205.
Roche, Bioreversible Carries in Drug Design Theory and Application, Pergamon Press, 1987, Table of Contents.

Satoh, T.; et al. Tetrahedron "New method for generation of β-oxido carbenoid via ligand exchange reaction of sulfoxides: A versatile procedure for on-carbon homologation of carbonyl compounds" 1994, 50, 11839-52.

Smith, et al., "Neuropathic Pain and the Electrophysiology and Pharmacology of Nerve Injury," Drug Development Research, 2001, vol. 54 (3), pp. 140-153.

Stark, Expert Opinion in Therapeutic Patents "Recent advances in histamine $H_3/H_4$ receptor ligands" 2003, vol. 13, pp. 851-865.

Steiner, et al., "Tricyclic Epines. Novel (E)- and (Z)-11H-Dibenz[b,e]azepines as Potential Central Nervous System Agents. Variation of the Basic Side Chain," Journal of Medicinal Chemistry, 1986, vol. 29 (10), pp. 1877-1888.

Stetter, et al., "Herstellung Cyclischer Diamine Des Mittleren Ringgebietes Durch Ringoffnung Bicyclischer Verbindungen," Chemische Berichte, 1958, vol. 91, pp. 1982-1988.

Stetter, et al., "Makrocyclische Diamide, ausgehend Von Aromatischen Diaminen," Chemische Berichte, 1958, vol. 91, pp. 677-680.

Suess, et al., "Regiospezifische Reduktionen von 1,3,3-trisubstituierten Succinimiden Mit Diboran," Helvetica Chimica Acta, 1977, vol. 60 (5), pp. 1650-1656.

Surleraux, et al., "Design of HIV-1 Protease Inhibitors Active on Multidrug-Resistant Virus," Journal of Medicinal Chemistry, 2005, vol. 48 (6), pp. 1965-1973.

Taniyama, et al., "Studies on Nocardamin and its Related Compounds. II. Synthesis of 2-(2-Aminoethyl) Azetidine," Yakugaku Zasshi, 1961, vol. 81, pp. 1497-1500.

Thurmond, et al., "A Potent and Selective Histamine H4 Receptor Antagonist with Anti-Inflammatory Properties," Journal of Pharmacology and Experimental Therapeutics, 2004, vol. 309, pp. 404-413.

Varga, et al., "Inhibitory Effects of Histamine H4 Receptor Antagonists on Experimental Colitis in the Rat.," European Journal of Pharmacology, 2005, vol. 522, pp. 130-138.

Vinik, et al., "Diabetic Neuropathies," The Medical Clinics of North America, 2004, vol. 88 (4), pp. 947-999.

Vogel, Drug Discovery and Evaluation: Pharmacological Assays, 2nd Edition, Springer-Verlag Berlin Heidelberg, 2002, pp. 702-706.

Wender, et al., "Organobis(cuprates): A New Class of Reagents and Method for Spiroannelation," Journal of the American Chemical Society, 1988, vol. 110, pp. 2218-2223.

Yoshida, et al., "Studies on Quinolone Antibacterials. V. Synthesis and Antibacterial Activity of Chiral 5-Amino-7-(4-Substituted-3-Amino-1-Pyrrolidinyl)-6-Fluoro-1,4-Dihydro-8-Methyl-4-Oxoquinoline-3-Carboxylic Acids and Derivatives," Chemical and Pharmaceutical Bulletin, 1996, vol. 44 (7), pp. 1376-1386.

Zhu, et al., "Asymmetric Synthesis. 29. Preparation of 1, 8-Diazaspiro[5.5]undecane Derivatives," Journal of Organic Chemistry, 1993, vol. 58 (23), pp. 6451-6456.

Zhu, et al., "Cloning, Expression, and Pharmacological Characterization of a Novel Human Histamine Receptor," Molecular Pharmacology, 2001, vol. 59 (3), pp. 434-441.

Jablonowska, et al., Distribution Pattern of Histamine H4 Receptor in Human Synovial Tissue from Patients with Rheumatoid Arthritis, 35th Meeting of the European Histamine Research Society in Delphi, Greece, Presentation 036, May 10-13, 2006.

* cited by examiner

MACROCYCLIC SPIRO PYRIMIDINE DERIVATIVES

CROSS-REFERENCE TO RELATED APPLICATIONS

This application claims priority to provisional application Ser. No. 61/035,440 filed Mar. 11, 2008, which is incorporated herein by reference.

BACKGROUND OF THE INVENTION

1. Technical Field

The invention relates to macrocyclic spiro pyrimidine compounds, compositions comprising the compounds, methods for making the compounds, and methods of treating conditions and disorders using such compounds and compositions.

2. Description of Related Technology

Histamine modulates a number of physiological activities, acting through specific histamine receptors (reviewed in Parsons and Ganellin, British Journal of Pharmacology (2006) 147, S127-S135; Igaz and Hegyesi, in Histamine: Biology and Medical Aspects (2004), 89-96; Editor(s): A. Falus; Published S. Karger A G, Basel). Four histamine receptors have been identified as playing distinct physiological roles. These are the histamine $H_1$ receptor, the histamine $H_2$ receptor, the histamine $H_3$ receptor, and the histamine $H_4$ receptor. Compounds that modulate, or affect, the activity of these receptors may be used to treat diseases. For example, the well-known role of $H_1$ receptors in modulating allergic reaction has led to the clinical development of drugs that treat allergic rhinitis and other diseases by antagonizing the action of naturally-occurring, or endogenous, histamine in the body. Histamine $H_2$ receptor antagonists have been developed and proven clinically useful in treating diseases associated with excess stomach acidity. The histamine $H_3$ receptor is found predominantly on nerve terminals in the central nervous system (CNS) and the peripheral nervous system, i.e., periphery, and antagonists of this receptor have been documented in studies that benefit mammalian cognitive process, improve wakefulness, suppress symptoms of allergic rhinitis, and suppress weight gain. The histamine $H_4$ receptor is the most recently identified histamine receptor and has been characterized as a distinct histamine receptor. The histamine $H_4$ receptor has been found in a number of mammalian tissues and has been determined to modulate a number of physiological processes, including immunological function.

By use of histamine $H_4$ ligands in animal disease models as well as in in vitro and ex vivo studies, the histamine $H_4$ receptor has been demonstrated to play an important role in various physiological and pathophysiological processes. Separately, in experiments with histamine $H_4$ deficient (knock out) animals and cells and tissues from such histamine $H_4$ deficient animals, the histamine $H_4$ receptor has been demonstrated to play an important role in various physiological and pathophysiological processes. Examples of diseases and disorders where histamine $H_4$ receptors have been found to play an important role include, for example, asthma, allergy, rheumatoid arthritis, and inflammation.

The activity of histamine $H_4$ receptors can be modified or regulated by the administration of histamine $H_4$ receptor ligands. The ligands can demonstrate antagonist, inverse agonist, or partial agonist activity.

Histamine $H_4$ ligands in different structural classes have been reviewed in (Schwartz, Expert Opinion in Therapeutic Patents (2003) vol. 13, pp. 851-865). It would be beneficial to provide additional compounds demonstrating $H_4$ receptor-modulating activity that can be incorporated into pharmaceutical compositions useful for therapeutic methods.

SUMMARY OF THE INVENTION

The invention is directed to macrocyclic spiro derivatives, particularly macrocyclic spiro pyrimidine derivatives, as well as compositions comprising and methods of using the same. Compounds of the invention have the formula (I):

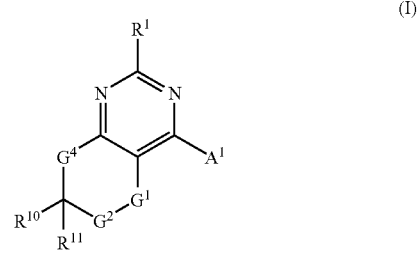

or a pharmaceutically acceptable salt, ester, amide, prodrug thereof, wherein $G^1$ is selected from oxygen, sulfur, S(O), S(O)$_2$, NR$^8$ and alkylene;

$G^2$ is selected from oxygen, sulfur, S(O), S(O)$_2$, NR$^8$, and alkylene;

wherein each carbon of the alkylene groups of $G^1$ and $G^2$ may be optionally substituted with one or more groups selected from acyl, acyloxy, alkenyl, alkoxy, alkoxyalkyl, alkoxyalkoxy, alkoxycarbonyl, alkyl, alkylcarbonyl, alkylcycloalkyl, alkylsulfonyl, alkylthio, alkynyl, amido, carboxy, cyano, cyanoalkyl, cycloalkoxyalkyl, cycloalkyl, fluorine, fluoroalkoxy, fluoroalkyl, fluorocycloalkyl, fluorocycloalkylalkyl, formyl, haloalkoxy, haloalkyl, halogen, hydroxy, hydroxyalkyl, mercapto, nitro, and oxo;

provided that only one of $G^1$ or $G^2$ can be oxygen, sulfur, S(O), S(O)$_2$ or NR$^8$;

$G^4$ is CH$_2$ or a bond;

$R^1$ is selected from hydrogen, NH$_2$, —NH(acyl), —NH(alkyl), —N(alkyl)$_2$, —NH(C=O)aryl, —NH-alkylene(NR$^8$R$^9$), —NH(C=O)-alkylene(NR$^8$R$^9$), —NR$^8$(C=O)NR$^8$R$^9$, —NH-alkylene-heteroaryl, —NHOH, —NHOCH$_3$, —O-alkylene(NR$^8$R$^9$), alkoxy, alkoxycarbonyl, alkyl, carboxy, —(C=O)—(NR$^8$R$^9$), —(C=O)—NH-alkylene(NR$^8$R$^9$), cyano, cyanoalkyl, cycloalkyl, fluoroalkyl, fluorocycloalkyl, hydroxyalkyl, and piperazine;

$R^6$ at each occurrence is independently selected from hydrogen, alkoxyalkyl, alkyl, alkylcycloalkyl, cyanoalkyl, cycloalkoxyalkyl, cycloalkyl, fluoroalkyl, fluorocycloalkyl, fluorocycloalkylalkyl, and hydroxyalkyl;

$R^7$ at each occurrence is independently is selected from alkoxyalkyl, fluoroalkyl, fluorocycloalkyl, fluorocycloalkylalkyl, and hydroxyalkyl;

$R^8$ and $R^9$ are each independently selected from acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, fluoroalkyl, fluorocycloalkyl, fluorocycloalkylalkyl, heteroaryl, heterocycle, hydrogen, formyl, hydroxy, and hydroxyalkyl;

$R^{10}$ and $R^{11}$ taken together are alkylene, —OCH$_2$CH$_2$O—, —OCH$_2$CH$_2$CH$_2$O—, —CH$_2$CH$_2$OCH$_2$CH$_2$—, or

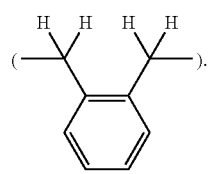
A$^1$ is a group of structure A$^2$ or A$^3$, wherein A$^2$ is
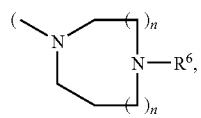  A
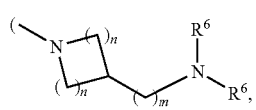  B
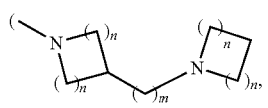  C
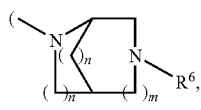  D
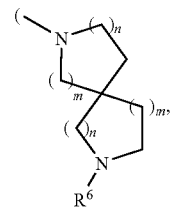  E
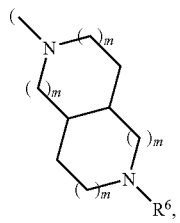  F
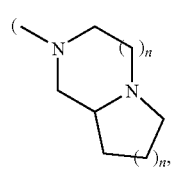  G
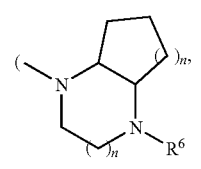  H
-continued
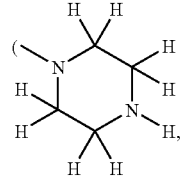  I
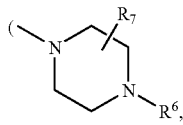  J
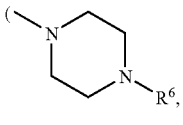  K
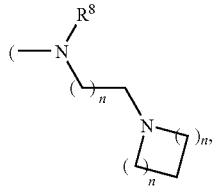  L
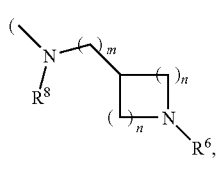  M
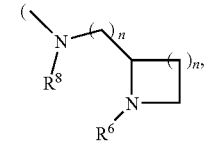  N
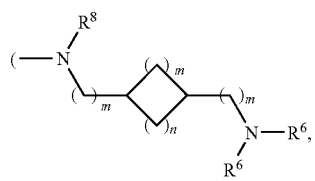  O
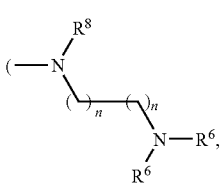  P
Q

| | | | |
|---|---|---|---|
| R | 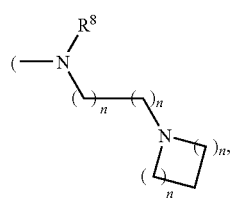 | Y3 | 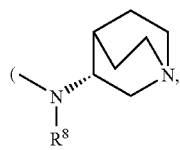 |
| S | 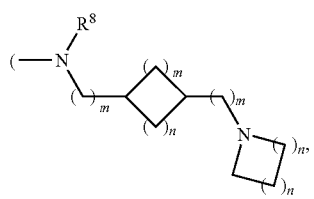 | Y4 | 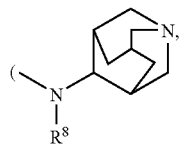 |
| T | 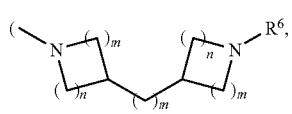 | Y5 | 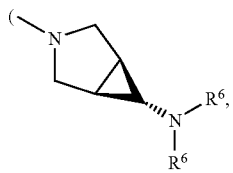 |
| U | 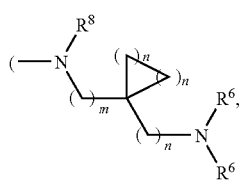 | Y6 | 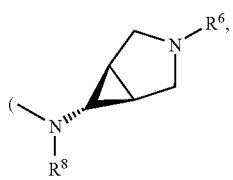 |
| V | 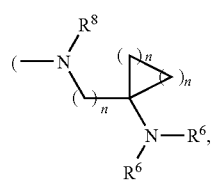 | Y7 | 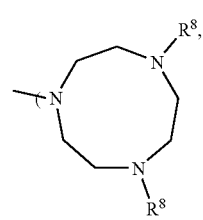 |
| W | 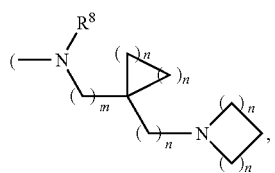 | Y8 | 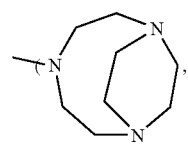 |
| X | 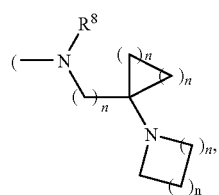 | Y9 | 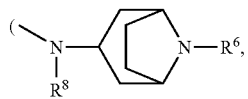 |
| Y1 | 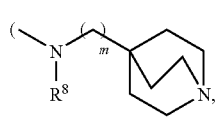 | Y10 |  |
| Y2 | 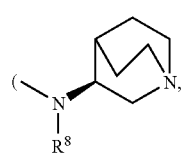 | Y11 | 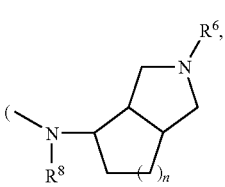 |
| | | Y12 | 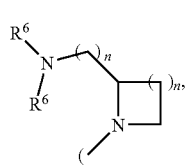 |

-continued

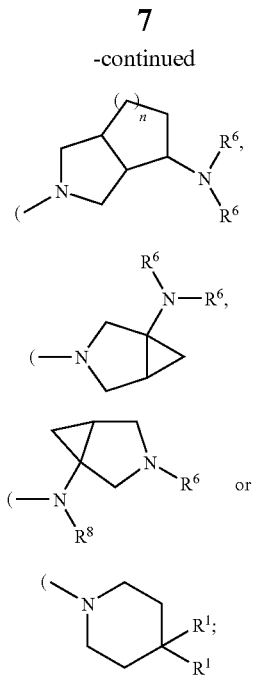

and A³ is selected from

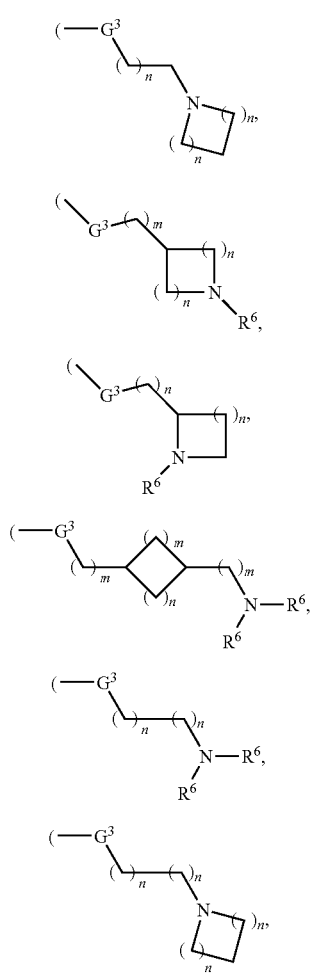

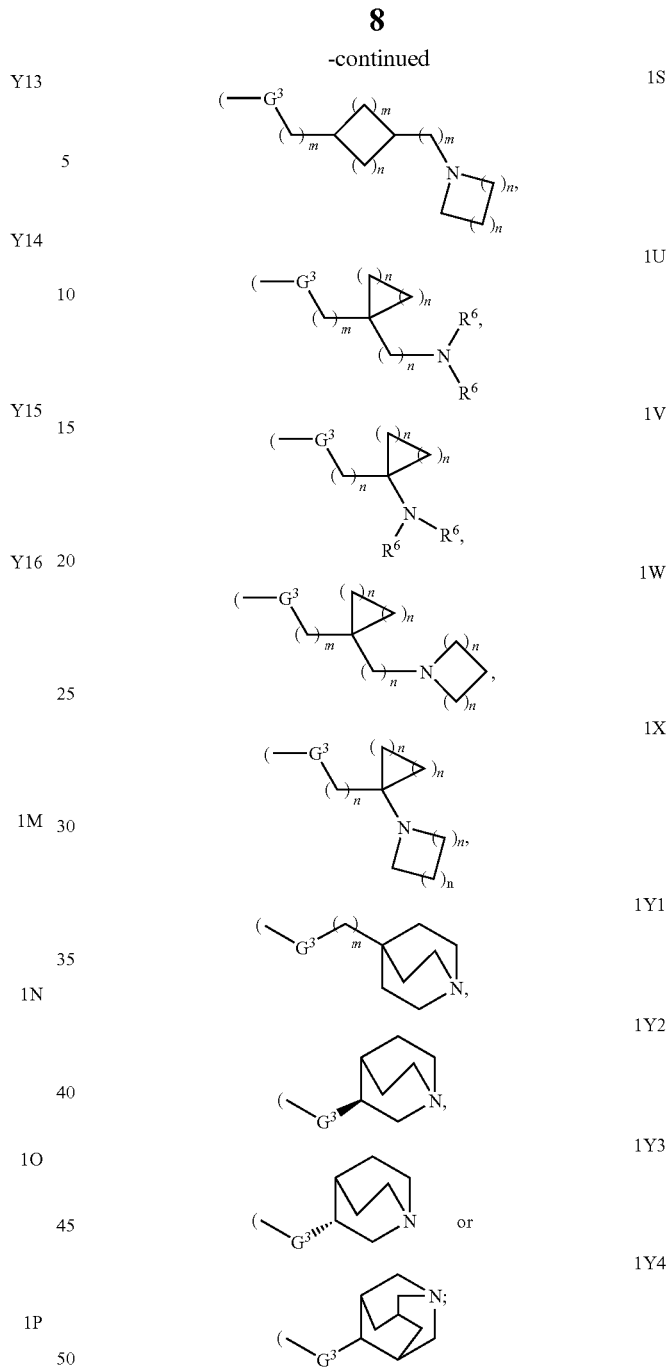

wherein G³ is O, S, S(O), S(O)₂;
n is 1, 2, or 3;
m is 0, 1, or 2;
wherein each carbon atom of groups A¹ may be optionally substituted with one or more groups selected from acyl, acyloxy, alkenyl, alkoxy, alkoxyalkoxy, alkoxyalkyl, alkoxycarbonyl, alkyl, alkylcarbonyl, alkylcycloalkyl, alkylsulfonyl, alkylthio, alkynyl, amido, carboxy, cyano, cyanoalkyl, cycloalkoxyalkyl, cycloalkyl, fluorine, fluoroalkoxy, fluoroalkyl, fluorocycloalkyl, fluorocycloalkylalkyl, formyl, haloalkoxy, haloalkyl, halogen, hydroxy, hydroxyalkyl, mercapto, and nitro.

Another aspect of the invention relates to pharmaceutical compositions comprising compounds of the invention. Such compositions can be administered in accordance with a method of the invention, typically as part of a therapeutic regimen for treatment or prevention of conditions and disorders related to histamine $H_4$ receptor activity.

In addition, compounds of the invention can have the formula (I) and also demonstrate an ability to modulate histamine $H_4$ receptor activity. In this aspect, the invention relates to a method of modulating histamine $H_4$ receptor activity. The method is useful for treating or preventing conditions and disorders related to histamine $H_4$ receptor modulation in mammals. More particularly, the method is useful for treating or preventing conditions and disorders related to the immune system involving inflammatory processes, autoimmune disease, and also in nervous system activities involved in pain, such as inflammatory pain, and non-inflammatory pain, especially neuropathic pain. Accordingly, the compounds and compositions of the invention are useful as a medicament for treating or preventing histamine $H_4$ receptor modulated disease. Examples of such conditions and disorders include, but are not limited to, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, osteoarthritis pain, post-surgical pain, non-inflammatory pain, neuropathic pain, subcategories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

Another aspect of the invention relates to the use of the compounds of the invention (compounds of formula (I)) in combination with histamine $H_1$ antagonists (such as loratidine), histamine $H_2$ antagonists (such as nizatidine), histamine $H_3$ antagonists (such as ABT-239 or GSK-189254), modulators of TNF-α (such as adalimumab), anti-inflammatory corticosteroids (such as dexamethasone), 5-lipoxygenase inhibitors (such as zileuton), leukotriene antagonists (such as zafirlukast) or LTB4 antagonists, with NSAIDS (such as ibuprofen) including, COX-2 inhibitors (such as celecoxib), with β-adrenergic receptor agonists such as salmeterol, anti-nociceptive opiate agonists (such as morphine), anti-nociceptive alpha adrenergic agonists (such as dexmedetomidine), TRPV1 antagonists, nicotinic agonists such as ABT-418 or (1S,5S)-3-(5,6-dichloro-3-pyridinyl)-3,6-diazobicyclo[3.2.0]heptane, CB-1 agonists, CB-2 agonists, P2X7 antagonists, metabotropic glutamate receptor antagonists, an anticonvulsant such as gabapentin or pregabilin, or a tricyclic antidepressant such as amitriptyline. The compounds, compositions comprising the compounds, and methods for treating or preventing conditions and disorders by administering the compounds, are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through a —C(=NH)— group, which also is defined as an imino group. Representative examples of alkoxyimino include, but are not limited to, methoxy(imino), ethoxy(imino) and tert-butoxy(imino).

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through an NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylcycloalkyl" as used herein means an alkyl group, as defined herein, appended to the parent molecular moiety through a cycloalkyl group, as defined herein. Representative examples of alkylcycloalkyl include, but are not limited to, 4-ethylcyclohexyl, 3-methylcyclopentyl, 2-isopropylcyclopropyl and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an $-NH_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, $-NR^8R^9$, $(NR^8R^9)$carbonyl, $-SO_2NR^8R^9$, $-NR^8(C=O)NR^8R^9$, $-NR^8(C=O)$alkyl, and $N(R^8)SO_2(R^9)$. Where the aryl group is a phenyl group, the number of substituents is 0, 1, 2, 3, 4, or 5. Where the aryl group is a bicyclic aryl, the number of substituents is 0, 1, 2, 3, 4, 5, 6, or 7. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a $-C(=O)-$ group.

The term "carboxy" as used herein means a $-CO_2H$ group.

The term "cyano" as used herein means a $-CN$ group, attached to the parent molecular moiety through the carbon.

The term "cyanoalkyl" as used herein means a $-CN$ group attached to the parent molecular moiety through an alkyl group. Representative examples of "cyanoalkyl" include, but are not limited to, 3-cyanopropyl, and 4-cyanobutyl.

The term "cyanophenyl" as used herein means a $-CN$ group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 10 carbons. Examples of cycloalkyl include cyclopropyl, cyclobutyl, cyclopentyl, cyclohexyl, cycloheptyl, and cyclooctyl. $C_3$-$C_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, fluoroalkoxy, formyl, haloalkoxy, haloalkyl, halogen, hydroxy, hydroxyalkyl, mercapto, oxo, nitro, alkylthio, $-NR^8R^9$, $(NR^8R^9)$carbonyl, $-SO_2N(R^8)$ $(R^9)$, $-NR^8(C=O)NR^8R^9$, $-NR^8(C=O)$alkyl, and $-N(R^8)SO_2(R^9)$, wherein, $R^8$ and $R^9$ are defined herein.

The term "cycloalkoxy" as used herein, means a cycloalkyl group, as defined herein, appended to the parent molecular moiety through an oxygen atom. Representative examples of cycloalkoxy include, but are not limited to, cyclohexyloxy and cyclopropoxy.

The term "cycloalkoxyalkyl" as used herein means a cycloalkoxy group, as defined herein, appended to the parent molecular moiety through an alkyl group, wherein alkyl is as defined herein. Representative examples of cycloalkoxyalkyl include, but are not limited to, cyclobutoxymethyl, cyclopentyloxymethyl, 2-(cyclopentyloxy)ethyl and cyclohexyloxymethyl.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. ($C_3$-$C_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through an alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" or "fluorine" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "fluorocycloalkyl" as used herein means a fluoro as defined herein, attached to a cycloalkyl moiety, attached to the parent molecular moiety through the cycloalkyl group. Representative examples of fluorocycloalkyl include, but are not limited to, 4-fluorocyclohexyl, 2,2-difluorocyclobutyl and the like.

The term "fluorocycloalkylalkyl" as used herein means a fluorocycloalkyl group as defined herein, attached to the parent molecular moiety through an alkyl group. Representative examples of fluorocycloalkylalkyl include, but are not limited to, (4-fluorocyclohexyl)methyl, (2,2-difluorocyclobutyl)methyl and the like.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing one or more heteroatoms independently selected from nitrogen, oxygen, and sulfur. Such rings can be monocyclic or bicyclic as further described herein.

The terms "monocyclic heteroaryl" or "5- or 6-membered heteroaryl ring", as used herein, refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contain 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and or one oxygen atom. The 5- or 6-membered heteroaryl is connected to the parent molecular moiety through any carbon atom or any substitutable nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring wherein one or more of the atoms of the ring have been replaced with at least one heteroatom selected from oxygen, sulfur, and nitrogen. The bicyclic heteroaryl of the invention maybe attached to the parent molecular moiety through any available carbon atom or nitrogen atom contained within the heteroaryl ring. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —$NR^8R^9$, ($NR^8R^9$)carbonyl, —$SO_2N(R^8)(R^9)$, —$NR^8(C=O)NR^8R^9$, —$NR^8(C=O)Oalkyl$, and —$N(R^8)SO_2(R^9)$. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring contains zero, one, or two double bonds provided that the ring, when taken together with a substituent, does not tautomerize with a substituent to form an aromatic ring and one, two, three, or four heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, hexahydropyrrolo[3,4-b]pyrrol-1(2H)-yl, tetrahydro-1H-pyrrolo[3,4-b]pyridin-6(2H,7H,7aH)-yl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, $-NR^8R^9$, $(NR^8R^9)$carbonyl, $-SO_2N(R^8)(R^9)$, $-NR^8(C=O)NR^8R^9$, $-NR^8(C=O)Oalkyl$, and $-N(R^8)SO_2(R^9)$.

The term "hydroxy" or "hydroxyl" as used herein means an $-OH$ group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyl iodide, benzyl iodide, triethylsilyltriflate, acetyl chloride, benzyl chloride, or dimethylcarbonate. A protecting group also may be appended onto a hydroxy group by reaction of the compound that contains the hydroxy group with acid and an alkyl acetal.

The term "imino" as defined herein means a $-C(=NH)-$ group.

The term "mercapto" as used herein means a $-SH$ group.

The term "$(NR^8R^9)$" as used herein means both an $R^8$ and $R^9$ group, wherein $R^8$ and $R^9$ are each as defined for compounds of formula (I), are appended to the parent molecular moiety through a nitrogen atom. The "$(NR^8R^9)$" is appended to the parent molecular moiety through the nitrogen atom.

The term "$(NR^8R^9)$alkyl" as used herein means an $-NR^8R^9$ group, as defined herein, appended to the parent molecular moiety through an alkyl group, as defined herein. Representative examples of $(NR^8R^9)$alkyl include, but are not limited to, 2-(methylamino)ethyl, 2-(dimethylamino)ethyl, 2-(amino)ethyl, 2-(ethylmethylamino)ethyl, and the like.

The term "$(NR^8R^9)$carbonyl" as used herein means an $-NR^8R^9$ group, as defined herein, appended to the parent molecular moiety through a carbonyl group, as defined herein. Representative examples of $(NR^8R^9)$carbonyl include, but are not limited to, aminocarbonyl, (methylamino)carbonyl, (dimethylamino)carbonyl, (ethylmethylamino)carbonyl, and the like.

The term "$-NR^8(C=O)Oalkyl$" as used herein means an amino group attached to the parent moiety to which is further appended a $R^8$ group as defined herein, and a $(C=O)$, i.e. carbonyl, group to which is appended an Oalkyl, i.e. alkoxy, group. Representative examples of $-NR^8(C=O)Oalkyl$ include, but are not limited to, methyl N-methylcarbamate, tert-butyl N-methylcarbamate, and the like.

The term "$-NR^8(C=O)NR^8R^9$" as used herein means an amino group attached to the parent moiety to which is further appended a $R^8$ group as defined herein, and a $(C=O)NR^8R^9$, i.e. $(NR^8R^9)$carbonyl, as defined herein. Representative examples of $-NR^8(C=O)NR^8R^9$ include, but are not limited to, methylurea, phenyl urea, and the like.

The term "$(NR^8R^9)$sulfonyl" as used herein means a $-NR^8R^9$ group, as defined herein, appended to the parent molecular moiety through a sulfonyl group, as defined herein. Representative examples of $(NR^8R^9)$sulfonyl include, but are not limited to, aminosulfonyl, (methylamino)sulfonyl, (dimethylamino)sulfonyl and (ethylmethylamino)sulfonyl.

The term "$-N(R^8)SO_2(R^9)$" as used herein means an amino group attached to the parent moiety to which is further appended with a $R^8$ group as defined herein, and a $SO_2$ group to which is appended an $(R^9)$ group as defined herein. Representative examples of $-N(R^8)SO_2(R^9)$ include, but are not limited to, N-methylmethanesulfonamide.

The term "$-SO_2(NR^8R^9)$" as used herein means a $NR^8R^9$ group appended to the parent moiety through a sulfonyl group. Representative examples of $-SO_2(NR^8R^9)$ include, but are not limited to (dimethylamino)sulfonyl and N-cyclohexyl-N-methylsulfonyl.

The term "nitro" as used herein means a $-NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-$C=O)_2O$, a diaryl anhydride, for example as represented by (aryl-$C=O)_2O$, an acyl halide, an alkylchloroformate, or an alkylsulfonylhalide, an arylsulfonylhalide, or halo-CON(alkyl)$_2$, for example acetyl chloride, benzoyl chloride, benzyl bromide, benzyloxycarbonyl chloride, formylfluoride, phenylsulfonyl chloride, pivaloyl chloride, (tert-butyl-O—C=O)$_2$O, trifluoroacetic anhydride, and triphenylmethylchloride.

The term "oxo" as used herein means (=O).

The term "sulfonyl" as used herein means a —S(O)$_2$— group.

Antagonists are ligands that block receptor activation by an agonist. In the case of the histamine H$_4$ receptor, a histamine H$_4$ receptor antagonist blocks activation of the histamine H$_4$ receptor by a histamine H$_4$ receptor agonist such as the endogenous agonist ligand histamine. Inverse agonists are ligands that block receptor activation more generally: they block intrinsic activation of a receptor that occurs in the absence of an agonist activation by an agonist, and also block receptor activation by an agonist. Partial agonists are ligands that bind to receptors but only partially activate the receptor; in so doing, partial agonists compete with full agonists and block full activation of the receptor. In the case of the histamine H$_4$ receptor, the endogenous agonist histamine is a full agonist.

Compounds of the Invention

Compounds of the invention can have the formula (I) as described in the Summary of the Invention. In addition, certain embodiments of the invention further describe compounds of formula (I):

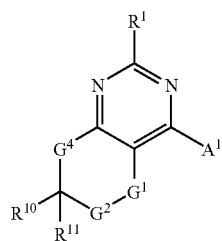

(I)

In compounds of formula (I), G$^1$ is oxygen, sulfur, S(O), S(O)$_2$, NR$^8$ or an alkylene group, for example a hydrocarbon chain of 1, 2, 3, 4, 5, 6, 7, 8, 9, or 10 carbons. Preferably, G$^1$ is —CH$_2$CH$_2$— or —CH$_2$—.

G$^2$ is selected from alkylene, oxygen, sulfur, S(O), S(O)$_2$, NR$^8$;

wherein each carbon of the alkylene groups of G$^1$ and G$^2$ may be optionally substituted with one or more groups selected from acyl, acyloxy, alkenyl, alkoxy, alkoxyalkyl, alkoxyalkoxy, alkoxycarbonyl, alkyl, alkylcarbonyl, alkylcycloalkyl, alkylsulfonyl, alkylthio, alkynyl, amido, carboxy, cyano, cyanoalkyl, cycloalkoxyalkyl, cycloalkyl, fluorine, fluoroalkoxy, fluoroalkyl, fluorocycloalkyl, fluorocycloalkylalkyl, formyl, haloalkoxy, haloalkyl, halogen, hydroxy, hydroxyalkyl, mercapto, nitro, and oxo;

provided that only one of G$^1$ or G$^2$ can be oxygen, sulfur, S(O), S(O)$_2$ or NR$^8$.

Preferably, G$^2$ is —CH$_2$— or —CH$_2$CH$_2$—.

G$^4$ is CH$_2$ or a bond.

Preferably, G$^4$ is a bond.

R$^1$ is selected from hydrogen, NH$_2$, —NH(acyl), —NH(alkyl), —N(alkyl)$_2$, NH(C=O)aryl, —NH-alkylene(NR$^8$R$^9$), —NH(C=O)-alkylene(NR$^8$R$^9$), —NH-alkylene-heteroaryl, —NHOH, —NHOCH$_3$, —O-alkylene(NR$^8$R$^9$), alkoxy, alkoxycarbonyl, alkyl, carboxy, —(C=O)—(NR$^8$R$^9$), —(C=O)—NH-alkylene(NR$^8$R$^9$), cyano, cyanoalkyl, cycloalkyl, fluoroalkyl, fluorocycloalkyl, hydroxyalkyl, and piperazine. Preferably, R$^1$ is NH$_2$.

R$^{10}$ and R$^{11}$ taken together are alkylene, —OCH$_2$CH$_2$O—, —OCH$_2$CH$_2$CH$_2$O—, —CH$_2$CH$_2$OCH$_2$CH$_2$—, or

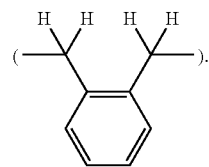

Preferably, R$^{10}$ and R$^{11}$ taken together are —CH$_2$CH$_2$CH$_2$CH$_2$— or —CH$_2$CH$_2$CH$_2$CH$_2$CH$_2$—.

A$^1$ is a group of structure A$^2$ or A$^3$ wherein A$^2$ is:

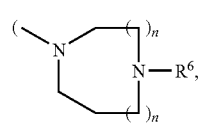

A

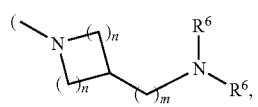

B

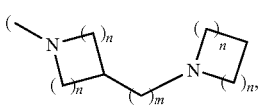

C

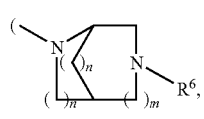

D

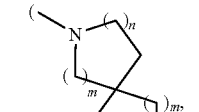

E

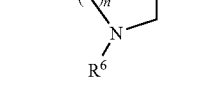

F

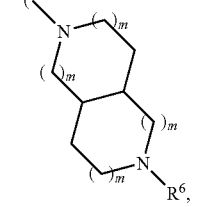

G

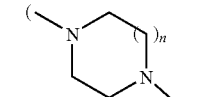

H

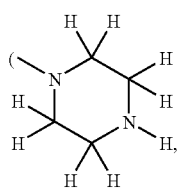 I
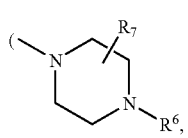 J
K
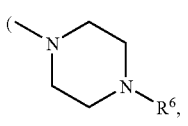 L
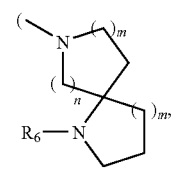 M
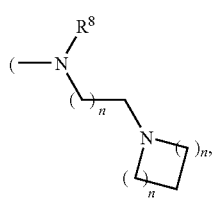 N
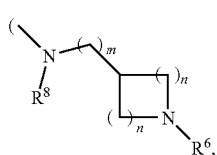 O
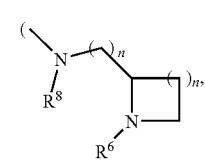 P
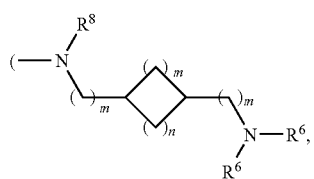 Q
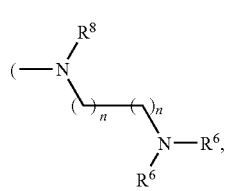
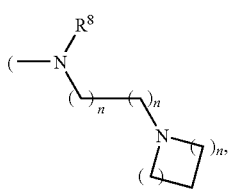 R
S
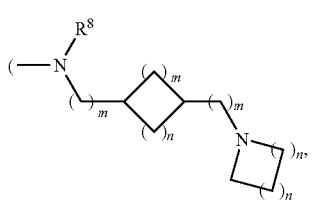 T
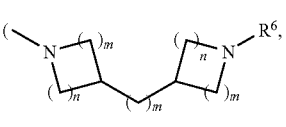 U
V
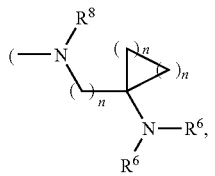 W
X
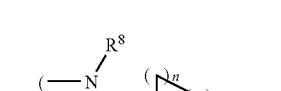 Y1
Y2
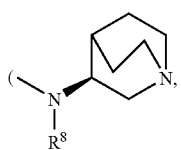

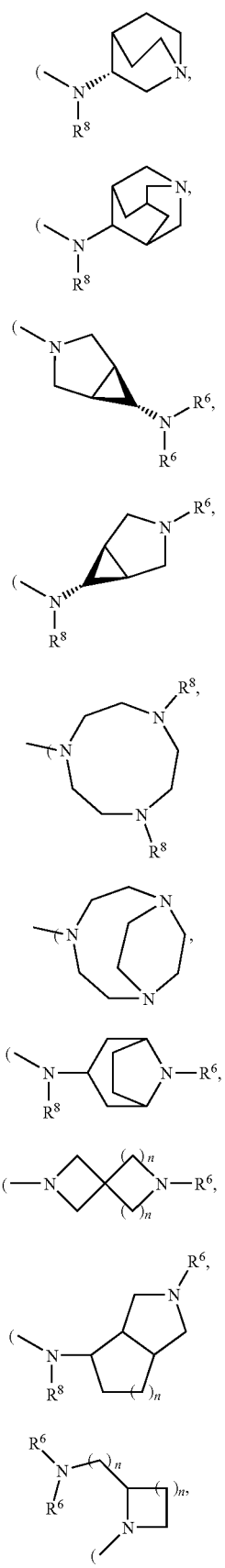
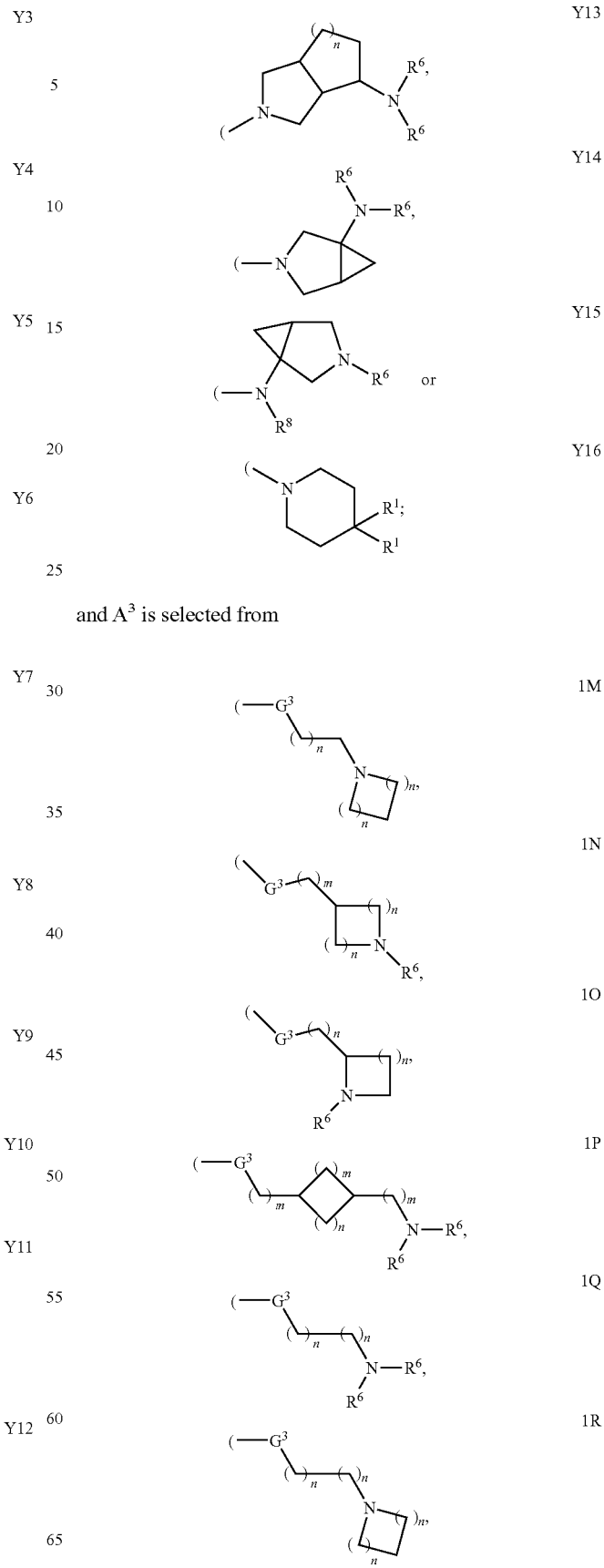
and $A^3$ is selected from

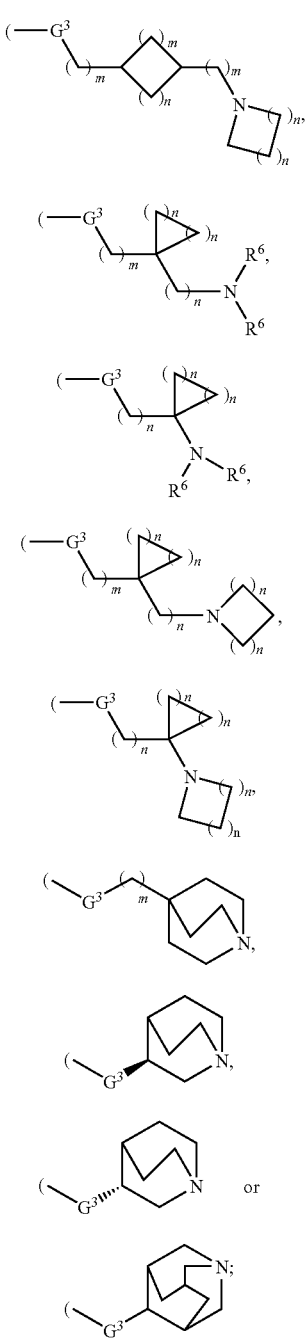

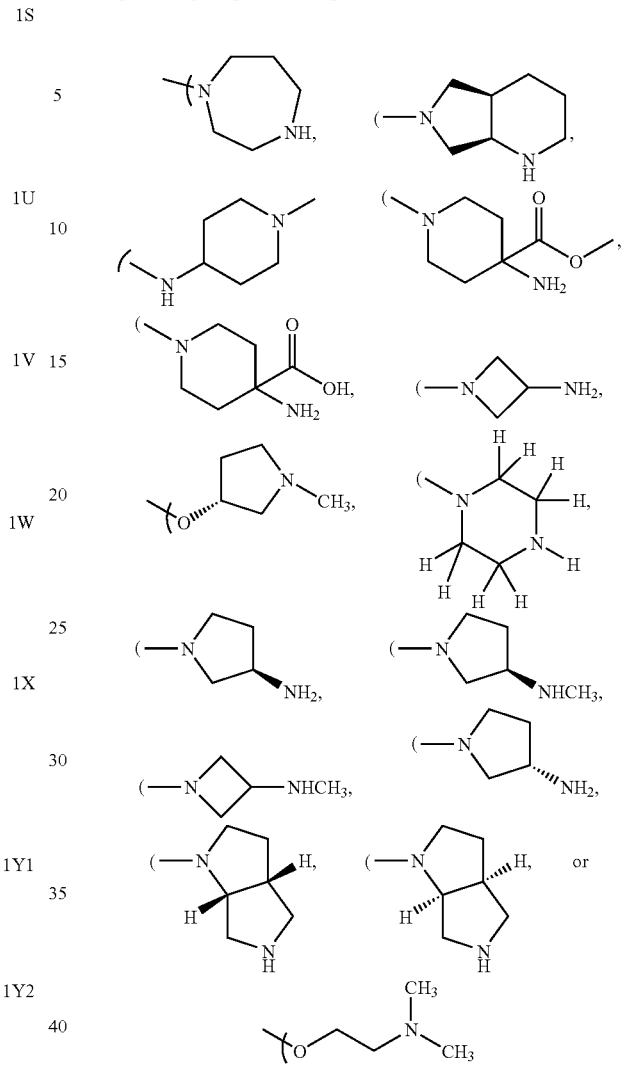

wherein $G^3$ is O, S, S(O), S(O)$_2$;

n is 1, 2, or 3;

m is 0, 1, or 2; and wherein each carbon atom of groups $A^1$ may be optionally substituted with one or more groups selected from acyl, acyloxy, alkenyl, alkoxy, alkoxyalkoxy, alkoxyalkyl, alkoxycarbonyl, alkyl, alkylcarbonyl, alkylcycloalkyl, alkylsulfonyl, alkylthio, alkynyl, amido, carboxy, cyano, cyanoalkyl, cycloalkoxyalkyl, cycloalkyl, fluorine, fluoroalkoxy, fluoroalkyl, fluorocycloalkyl, fluorocycloalkylalkyl, formyl, haloalkoxy, haloalkyl, halogen, hydroxy, hydroxyalkyl, mercapto, and nitro.

Specific groups contemplated for $A^1$ have the structure:

Suitable groups for $G^1$, $G^2$, $G^4$, $R^1$, $R^{10}$, $R^{11}$, and $A^1$ in compounds of formula (I) are each independently selected. The described embodiments of the present invention may be combined. Such combination is contemplated and within the scope of the present invention. For example, it is contemplated that preferred groups for any of $G^1$, $G^2$, $G^4$, $R^1$, $R^{10}$, $R^{11}$, and $A^1$ can be combined with groups defined for any other of $G^1$, $G^2$, $G^4$, $R^1$, $R^{10}$, $R^{11}$, and $A^1$, whether or not such group is preferred.

There also exists a pharmaceutical composition comprising a compound of formula (I) and a pharmaceutically acceptable carrier.

Representative examples of the invention are further described herein in the Examples. In particular, preferred embodiments contemplated as part of the invention also include 4'-(piperazin-1-yl)-6',7'-dihydro-5'H-spiro[cyclopentane-1,8'-quinazolin]-2'-amine, (R)-4'-(3-(methylamino)pyrrolidin-1-yl)-6',7'-dihydro-5'H-spiro[cyclopentane-1,8'-quinazolin]-2'-amine, 4'-(3-(methylamino)azetidin-1-yl)-6',7'-dihydro-5'H-spiro[cyclopentane-1,8'-quinazolin]-2'-amine, and (R)-4'-(3-aminopyrrolidin-1-yl)-6',7'-dihydro-5'H-spiro[cyclopentane-1,8'-quinazolin]-2'-amine. The practice of assigning names to chemical compounds from structures, and of assigning chemical structures from given chemical names, is well known to those of ordinary skill in the art.

Compounds of the invention may exist as stereoisomers, wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof, and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may be attached in such a manner that they are on the same side of the ring (cis) relative to each other, or on opposite sides of the ring relative to each other (trans). For example, cyclobutanes and cyclohexanes may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Methods of the Invention

Compounds and compositions of the invention are useful for modulating the histamine $H_4$ receptor, particularly by histamine $H_4$ receptor antagonism, partial agonism, or inverse agonism. In particular, the compounds and compositions of the invention can be used for treating and preventing disorders modulated by the histamine $H_4$ receptor. Typically, such disorders can be ameliorated by modulating histamine $H_4$ receptors in a mammal, preferably by administering a compound or composition of the invention, either alone or in combination with another active agent, for example, as part of a therapeutic regimen.

Certain substituted macrocyclic spiro pyrimidine compounds, including but not limited to those specified as compounds of the invention, demonstrate the ability to affect histamine $H_4$ receptor activity, and in particular demonstrate histamine $H_4$ receptor antagonism. Such compounds can be useful for the treatment and prevention of a number of histamine $H_4$ receptor-mediated diseases or conditions. Compounds of the invention demonstrate such activity and have the formula (I), as previously defined herein.

There is also disclosed a method of treating a mammal having a condition where modulation of histamine $H_4$ receptor activity is of therapeutic benefit, said method comprising administering to a subject having or susceptible to said disorder with a therapeutically effective amount of a compound of the formula (I), or a pharmaceutically acceptable salt, ester, amide, or prodrug thereof, as presented in the Summary of the Invention and Detailed Description sections of the present Invention.

There is also disclosed a method of treating a mammal having a condition where modulation of histamine $H_4$ receptor activity is of therapeutic benefit. The method comprises administering to a subject having or susceptible to said disorder a therapeutically effective amount of a compound of the formula (I), as previously defined.

The method is particularly beneficial when the condition or disorder is asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, or spinal cord injury pain.

In particular, it is particularly beneficial to administer compounds of formula (I) for the prevention and treatment of asthma.

It also is particularly beneficial to administer compounds of formula (I) for the prevention and treatment of inflammation.

It also is particularly beneficial to administer compounds of formula (I) for the prevention and treatment of pain. More particularly, it is beneficial to administer compounds of formula (I) for prevention and treatment of inflammatory pain. Compounds of formula (I) also demonstrate therapeutic benefit in treating and preventing non-inflammatory pain. In particular, compounds of formula (I) can be administered for treatment and prevention of neuropathic pain.

As an important consequence of the ability of the compounds of the invention to modulate the effects of histamine $H_4$ receptors in cells, the compounds described for the method of the invention can affect physiological processes in humans and animals. In this way, the compounds and compositions of formula (I) are useful for treating and preventing diseases and disorders modulated by histamine $H_4$ receptors. Typically, treatment or prevention of such diseases and disorders can be effected by modulating the histamine $H_4$ receptors in a mammal by the administration of a compound or composition of the invention, either alone or in combination with another active agent as part of a therapeutic regimen.

Particularly preferred are compounds of formula (I) for the method, include, but are not limited to, 4'-(piperazin-1-yl)-6',7'-dihydro-5'H-spiro[cyclopentane-1,8'-quinazolin]-2'-amine, (R)-4'-(3-(methylamino)pyrrolidin-1-yl)-6',7'-dihydro-5'H-spiro[cyclopentane-1,8'-quinazolin]-2'-amine, 4'-(3-(methylamino)azetidin-1-yl)-6',7'-dihydro-5'H-spiro[cyclopentane-1,8'-quinazolin]-2'-amine, and (R)-4'-(3-aminopyrrolidin-1-yl)-6',7'-dihydro-5'H-spiro[cyclopentane-1,8'-quinazolin]-2'-amine.

Compounds of formula (I) can be administered to a subject having such a disorder or susceptible to such disorders in a therapeutically effective amount. The compounds are particularly useful for a method of treating a mammal having a condition where modulation of histamine $H_4$ receptor activity is of therapeutic benefit, wherein the method is accomplished by administering a therapeutically effective amount of a compound of formula (I) to a subject having, or susceptible to, such a disorder.

Compounds useful for the method of the invention include, but are not limited to, those specified in the examples and possess an affinity for the histamine $H_4$ receptor. Such compounds therefore may be useful for the treatment and prevention of diseases or conditions related to histamine $H_4$ modulation. Examples of such diseases or conditions are, for example, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain. The ability of histamine $H_4$ receptor modulators, and consequently the compounds of the invention, to prevent or treat such disorders is demonstrated by evidence and examples found in references which follow.

Histamine $H_4$ receptor ligands have utility in treatment of a number of diseases and conditions, including asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

The histamine $H_4$ receptor, or gene message coding for the histamine $H_4$ receptor (detected as cDNA by reverse transcriptase polymerase chain amplification (RTPCR) of cellular messenger (mRNA)), has been detected in a number of cells and tissues critically affected in disease conditions. For example, the histamine $H_4$ receptor plays a critical role in inflammation, in autoimmune disorders such as rheumatoid arthritis, and in disorders of the immune system. For example, the histamine $H_4$ receptor has been detected in cells of the immune system and in organs of the immune system: neutrophils, eosinophils, basophils, dendritic cells, mast cells, bone marrow, thymus, spleen, brain. For examples, see Liu, et al. Molecular Pharmacology (2001) vol. 59 pp. 420-426; de Esch, et al. Trends in Pharmacological Sciences Vol. 26 No. 9 pp. 462-469; Oda, et al. Journal of the Pharmocological Society (2005) vol. 98, pp. 319-322; Zhu, et al. Molecular Pharmacology, (2001), v. 59, pp. 434-441; Gutzmer, et al. Journal of Immunology (2005) vol. 174 pp. 5224-5232; Coge, et al., Biochemical and Biophysical Research Communications (2001) vol. 284, pp. 301-309.

Histamine $H_4$ receptor is found at high (compared to normal) levels in disease tissues in rheumatoid arthritis, see for example, Grzybowska-Kowalczyk et al., Inflammation Research (2007), 56, Supplement 1, S1-S2; Maslinska, et al. 34th Meeting of the European Histamine Research Society in Bled, Slovenia 2005 poster number 3; Jablonowska, et al. 35th Meeting of the European Histamine Research Society in Delphi, Greece (May 10-13, 2006) presentation 036; Ikawa, et al. Biol. Pharm. Bull. (2005) vol. 28(10) pp. 2016-2018.

The role of histamine $H_4$ receptors in allergy, asthma, and allergic airway inflammation is shown by the finding that transgenic mice without histamine $H_4$ receptors are resistant to the development of disease in an animal model of asthma. The observation that a selective synthetic $H_4$ ligand elicits the same benefit in the asthma model also supports the benefits of $H_4$ ligands in treatment of disease. For example, see Dunford, et al. The Journal of Immunology (2006) vol. 176, pp. 7062-7070.

General reviews and papers on the role of histamine receptor in disease include Akdis and Simons, European Journal of Pharmacology (2006) vol. 533 pp. 69-76; de Esch, et al., Trends in Pharmacological Sciences Vol. 26 No. 9 pp. 462-469; Thurmond, et al., Journal of Pharmacology and Experimental Therapeutics (2004) vol. 309 pp. 404-413; Buckland, et al., British Journal of Pharmacology (2003) 140, 1117-1127. The utility for histamine $H_4$ receptor ligands in cancer is supported by the finding that the $H_4$ receptor has been found expressed on mammary cell carcinoma tissues, as reported by Maslinska, et al., 34th Meeting of the European Histamine Research Society in Bled, Slovenia (May 11-15, 2005) presentation. Histamine $H_4$ receptor activation was found to exert a proliferative effect in cancer tissues, Cianchi, et al., Clinical Cancer Research (2005) vol. 11 (19) pp. 6807-6815. In gastritis and gastric lesions, histamine $H_4$ ligands were found to reduce the lesions induced by administration of indomethacin in vivo: Coruzzi, et al. Jablonowska, et al. 35th Meeting of the European Histamine Research Society in Delphi, Greece (May 10-13, 2006) presentation O44. In colitis, histamine $H_4$ ligands were found to reduce the lesions induced by administration of trinitrobenzesulfonic acid in vivo: Varga, et al., European Journal of Pharmacology (2005) vol. 522 pp. 130-138; Fogel, et al., 35th Meeting of the European Histamine Research Society in Delphi, Greece (May 10-13, 2006) presentation P32. In itch and pruritis, the benefit of histamine $H_4$ receptor ligands has been shown by Bell, et al., British Journal of Pharmacology (2004) vol. 142, pp. 374-380.

The invention also relates to use of the compounds of the invention as histamine $H_4$ receptor ligands to treat pain, including distinctly different types of pain, including inflammatory pain, chemically induced pain, pain resulting from surgery, pain resulting from burns, pain resulting from osteoarthritis, non-inflammatory pain, and neuropathic pain. The usefulness of histamine $H_4$ receptor ligands in treating pain has been demonstrated (U.S. patent application Ser. No. 11/863,925; Coruzzi, et al., *Eur. J. Pharmacol.* 2007, 563, 240-244).

Neuropathic pain is distinct from other types of pain (e.g. inflammatory pain) in that it can develop in response to previous or ongoing tissue, nerve injury, or diabetes, but it persists long after signs of the original injury or damage have disappeared. Neuropathic pain is associated with allodynia, hyperalgesia, or causalgia (Dworkin Clinical Journal of Pain (2002) vol. 18(6) pp. 343-9). Allodynia is the perception of pain following a stimulus that would not normally be painful. Hyperalgesia is an enhanced response to a mildly noxious stimulus. Causalgia is described as a chronic burning pain that shows persistence in the absence of obvious noxious stimuli.

Neuropathic pain is not well treated with current therapies, and therefore there is a strong need for methods to treat this particular type of pain. The topic of neuropathic pain has been reviewed in the scientific literature, for example, Smith, et al., Drug Development Research (2001) vol. 54(3), pp. 140-153; Collins and Chessell, Expert Opinion on Emerging Drugs (2005) vol. 10(1), pp. 95-108; Vinik and Mehrabyan, Medical Clinics of North America (2004), vol. 88(4), pp. 947-999; Dray, Urban, and Dickenson, Trends in Pharmacological Sciences (1994) vol. 15(6) pp. 190-7; Dworkin, Clinical Journal of Pain (2002) vol. 18(6) pp. 343-9. A number of animal models of neuropathic pain that can be used to assess the ability of the compounds of the invention to treat neuropathic pain exist and are further discussed inter alia. Compounds of the invention are effective in treatment of neuropathic pain. Compounds of the invention are also effective in treating other types of pain, non-inflammatory pain, post surgical pain, and inflammatory pain.

Neuropathic pain is a description that encompasses more specific names of pain that are sub-categories of neuropathic pain (Dworkin, Clinical Journal of Pain (2002) vol. 18(6) pp. 343-9) including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

In addition to neuropathic pain, there are other types of pain that are not inflammatory or not due to ongoing inflammation, including osteoarthritis pain, cancer pain, and visceral pain. A general review of animal models of pain is found in Joshi and Honore, Expert Opinion in Drug Discovery (2004) 1, pp. 323-334.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in a pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 5 to about 500 micromoles/kg of body weight. For purposes of oral administration, more preferable doses can be in the range of from about 30 to about 500 micromoles/kg body weight. If desired, the effective daily dose can be divided into multiple doses for purposes of administration; consequently, single dose compositions may contain such amounts or submultiples thereof to make up the daily dose.

Methods for Preparing Compounds of the Invention

The compounds of the invention can be better understood in connection with the following synthetic schemes and methods, which illustrate a means by which the compounds can be prepared.

Abbreviations which have been used in the descriptions of the schemes and the examples that follow are: Boc for butyloxycarbonyl; DMF for N,N-dimethylformamide; DMSO for dimethyl sulfoxide; dppf for 1,1'-bis(diphenylphosphino)ferrocene; EDTA for ethylenediaminetetraacetic acid; $Et_2O$ for diethyl ether; EtOAc for ethyl acetate; HEK for human embryonic kidney cells; HPLC for high pressure liquid chromatography; MCPBA for 3-chloroperoxybenzoic acid; Me for methyl; MeOH for methanol; Ms for methanesulfonyl; Pd for palladium; tBu for tert-butyl; TEA for triethylamine; TFA for trifluoroacetic acid; THF for tetrahydrofuran; Tf for trifluoromethanesulfonyl; Ts for para-toluenesulfonyl; Tris for trishydroxymethylaminomethane; dba for dibenzylidineacetone; DMAP for 4-di(methylamino)pyridine; OAc for acetoxy; Ph for phenyl; HOAc for acetic acid; HMPA for hexamethylphosphoramide; MeI for methyl iodide; rt for "room temperature" or ambient temperature suitably ranging 17-30° C. CAS numbers may be used as identifiers of compounds available from descriptions reported in the literature or available commercially. CAS numbers are identifier numbers assigned to compounds by the Chemical Abstracts Service of the American Chemical Society and are well known to those of ordinary skill in the art.

The compounds of this invention can be prepared by a variety of synthetic procedures. Representative procedures are shown in, but are not limited to, Schemes 1-13.

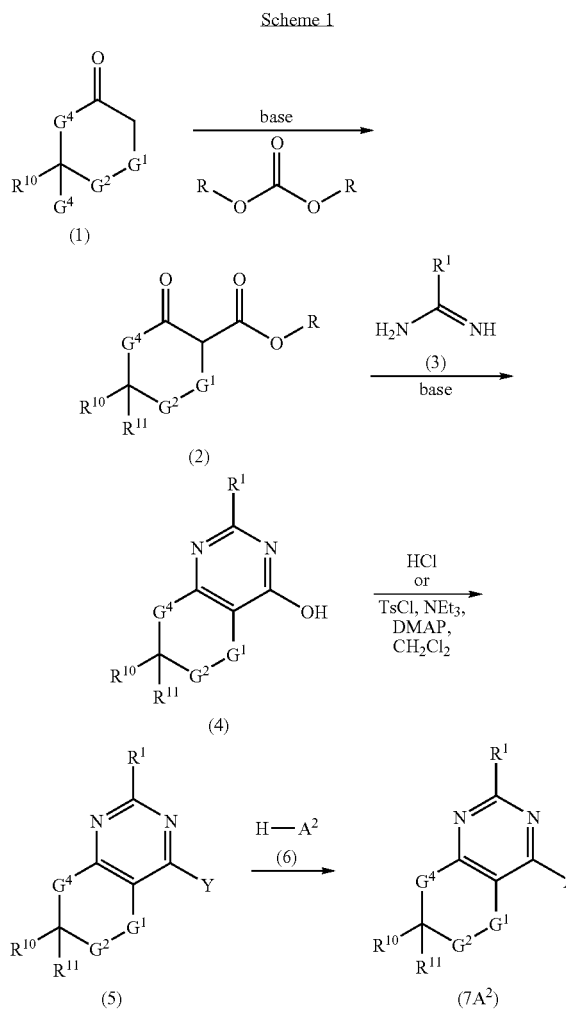

Compounds of formula ($7A^2$), wherein $R^1$, $R^{10}$, $R^{11}$, $A^2$, $G^1$, $G^2$, and $G^4$ are defined in formula (I), may be prepared as outlined in Scheme 1. Ketones of formula (1), which are obtained either from commercial sources or synthesized through the methods outlined herein, when treated with a base such as sodium hydride or butyllithium, followed by treatment with either a carbonate such as dimethyl carbonate, or a chloroformate such as ethyl chloroformate, will provide ketoester containing compounds of formula (2), wherein R is lower alkyl. Compounds of formula (2) when treated with a compound of formula (3), such as guanidine nitrate, in the presence of a base such as potassium carbonate under heated conditions in a solvent such as DMF will provide compounds of formula (4). Compounds of formula (4) can exist as shown in the structure in scheme 1 or in a tautomeric form. Compounds of formula (4) when treated with a chlorinating reagent such as but not limited to HCl, with or without heating as needed, will provide compounds of formula (5), wherein Y=Cl. Alternatively, compounds of formula (4) may also be treated with reagents such as para-toluenesulfonyl chloride, methylsulfonyl chloride or trifluoromethanesulfonyl chloride in the presence of a base such as triethylamine in a solvent such as pyridine or chloroform to provide compounds of formula (5) wherein Y=O—$SO_2$—R', wherein R' is lower alkyl, lower fluoroalkyl or aryl. Compounds of formula (5), wherein Y=Cl or —O—$SO_2$—R', when treated with compounds of formula (6), wherein (6) contains a primary or secondary nitrogen atom and H is a hydrogen atom on said nitrogen atom, under heated conditions in the presence or absence of a base such as triethylamine or diisopropylethylamine, in a solvent such as ethanol, 2-methoxyethanol, toluene or acetonitrile, will provide compounds of formula ($7A^2$).

Compounds of formula ($7A^2$), wherein $R^1$=H and $R^{10}$, $R^{11}$, $A^2$, $G^1$, $G^2$ and $G^4$ are defined in formula (I), may be prepared by treating a compound of formula (2) with thiourea with heating in the presence of a base such as sodium methoxide in a solvent such as methanol, followed by reduction of the resulting product using a reagent such as Raney nickel to provide compounds of formula (4) wherein $R^1$=H. Compounds of formula (4) wherein $R^1$=H can be treated according to the method above to provide compounds of formula ($7A^2$) wherein $R^1$=H.

Compounds of formula ($7A^2$) may be further reacted, according to conditions known to one skilled in the art, so as to alter functional groups contained within the compound (for example, the removal of a protecting group such as Boc or the hydrolysis of an ester group), in order to generate compounds of the present invention or used within the scope of other schemes described herein.

Compounds of formula (6) that contain two different nitrogen atoms may selectively react with compounds of formula (5) to provide one isomer of formula ($7A^2$). Such selectivity may be the result of substitution or protecting groups attached to one of the nitrogen atoms. Alternatively, compounds of formula (6) that contain two different N—H groups may react with compounds of formula (5) in a non-selective manner wherein a mixture of two different compounds of formula ($7A^2$) is obtained from the reaction. Mixtures of compounds of formula ($7A^2$) are generally separated by methods known to one skilled in the art, such as silica based column chromatography, selective recrystallization, or both.

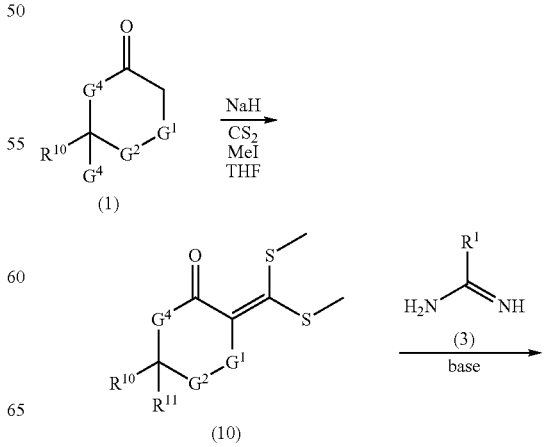

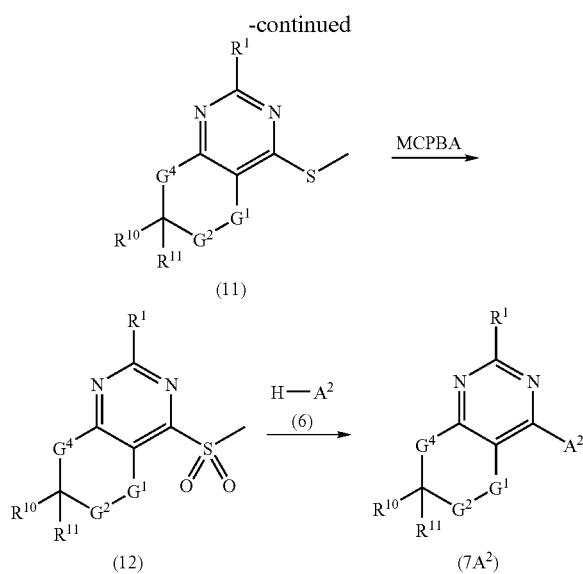

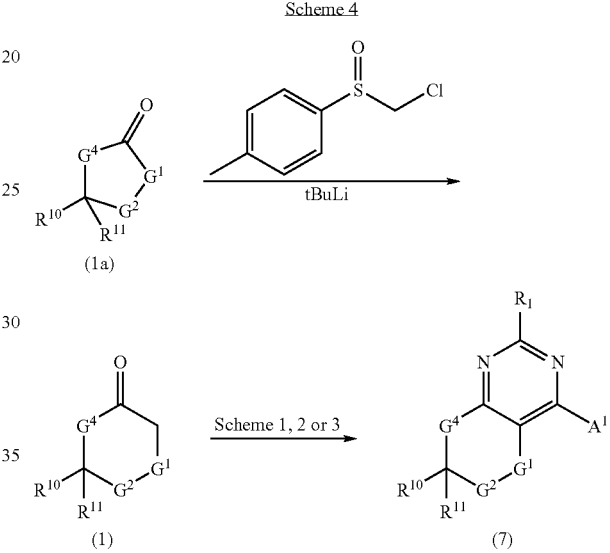

Alternatively, compounds of formula (7A²), which are representative of compounds of the present invention wherein R¹, R¹⁰, R¹¹, A², G¹, G², and G⁴ are defined in formula (I), may also be prepared as outlined in Scheme 2. Compounds of formula (1) when treated with carbon disulfide and iodomethane in the presence of a base such as but not limited to NaH in a solvent such as but not limited to THF will provide compounds of formula (10). Compounds of formula (10), when treated with a compound of formula (3), wherein R¹ is defined in formula (I), will provide sulfides of formula (11). Compounds of formula (11), when treated with an oxidizing agent such as MCPBA or Oxone® will provide sulfones of formula (12). Compounds of formula (12), when treated with compounds of formula (6), which contain a primary or secondary amine under heated conditions, in the presence or absence of a base such as triethyl amine or diisopropylethylamine, in a solvent such as ethanol or 2-methoxyethanol, will provide compounds of formula (7A²), which are representative of compounds of the present invention.

Scheme 3

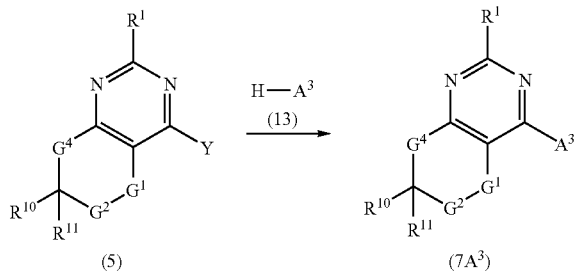

Compounds of formula (7A³), wherein R¹, R¹⁰, R¹¹, A³, G¹, G², and G⁴ are defined in formula (I), may be prepared as outlined in Scheme 3. Alcohols and thiols of formula (13), and alcohols and thiols that also contain an amine group wherein the nitrogen atom is protected with a synthetic protecting group such as a butoxycarbonyl group, which are obtained either from commercial sources or synthesized through the methods outlined herein, can be treated with a base such as sodium hydride, then treated with compounds of formula (5), wherein Y=Cl, p-toluenesulfonyl or SO₂Me, and then heated to provide compounds of formula (7A³). Alternative bases such as potassium tert-butoxide, potassium hydride, and potassium carbonate may also be employed. More generally, alcohols and thiols of formula (13) are described in the scientific literature and may be prepared by those of ordinary skill in the art of organic synthesis.

Compounds of formula (7A³) may be further reacted, according to conditions known to those of ordinary skill in the art of organic synthesis, to alter functional groups (for example, the removal of a protecting group such as Boc or the hydrolysis of an ester group), in order to generate compounds of the present invention or to be further transformed within the scope of other schemes described herein.

Compounds of formula (7), which are representative of compounds of the present invention wherein R¹, R¹⁰, R¹¹, A¹, G₂, and G⁴ are as defined in formula (I), and G¹ is alkylene, can be prepared as outlined in Scheme 4. Treatment of compounds of formula (1a) with p-toluenesulfonymethyl chloride in the presence of a base such as t-butyllithium will provide compounds of formula (1), wherein G¹ is alkylene. Further examples describing similar reactions are found in the following reference: Satoh, T.; et al. *Tetrahedron* 1994, 50, 11839-52. Compounds of formula (1), when treated as outlined in Schemes 1, 2 or 3, will provide compounds of formula (7), which are representative of compounds of the present invention wherein G¹ is alkylene.

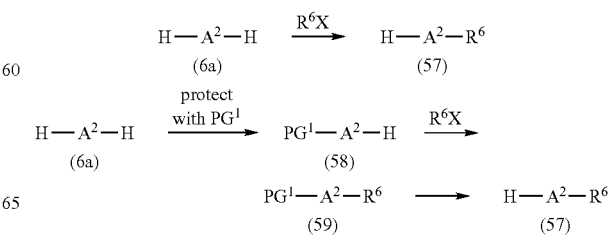

-continued

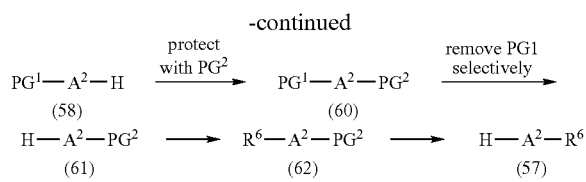

As outlined in Scheme 5, compounds of formula (6a) may contain two amine groups. The amine groups of compounds of formula (6a) may be either primary or secondary and can be used directly in Schemes 1 or 2 to provide compounds of formula (7A$^2$). Alternatively, compounds of formula (6a), which contain two N—H groups, may be treated with an appropriate reagent such as R$^6$—X, wherein X is a leaving group such as chlorine, bromine, iodine, mesylate, or triflate, to provide compounds of formula (57), wherein one of the two N—H groups is substituted with R$^6$. Substituting compounds of formula (57) for compounds of formula (6) in the procedures outlined in Scheme 1 or Scheme 2 will provide compounds of formula (7A$^2$), which are representative of the present invention.

Furthermore, compounds of formula (6a) that contain two amine groups may be treated with a reagent which will introduce a nitrogen protecting group (PG$^1$) on one of the amine groups. Some typical examples of common nitrogen protecting groups include, but are not limited to, benzyl, tert-butoxycarbonyl, benzyloxycarbonyl, or acetyl. Such groups are introduced by treating amines of formula (6a) with 1 equivalent of an appropriate reagent such as benzyl bromide, di-tert-butyl dicarbonate, benzyl chloroformate, or acetic anhydride, respectively, to provide mono-protected diamines of formula (58). Mono-amine protected compounds of formula (58) can be further treated with an appropriate reagent such as R$^6$—X, wherein R$^6$ is defined in formula (I) and X is a leaving group such as chlorine, bromine, iodine, mesylate, or triflate, to provide compounds of formula (59). Compounds of formula (59) can be deprotected to provide compounds of formula (57), which can then be used to replace compounds of formula (6) in the procedures outlined in Scheme 1 and Scheme 2 to provide compounds of formula (7A$^2$), which are representative of compounds of the present invention. Common conditions used for the deprotection of compounds of formula (59) to provide compounds of formula (57) include, but are not limited to, the following: catalytic hydrogenation (e.g. in the presence of palladium-on-carbon in a solvent such as ethanol under an atmosphere of hydrogen); acidic conditions (e.g. treatment with aqueous hydrochloric acid); or basic hydrolysis (e.g. treatment with aqueous sodium hydroxide and heat).

Alternatively, mono-protected diamines of formula (58) may be treated with an appropriate aldehyde or ketone under reductive amination conditions to provide diamines of formula (59). Conditions commonly used for reductive amination include treatment of an amine (58) with an aldehyde or ketone in the presence of NaBH$_3$CN or NaBH(OAc)$_3$.

Mono-protected compounds of formula (58) can be treated with a second protecting group (PG$^2$) to provide di-protected compounds of formula (60). In di-protected compounds of formula (60), it is preferred that the choice of protecting groups is such that the protecting group PG$^1$ can be removed selectively without removing PG$^2$. Selective deprotection of PG$^1$ from compounds of formula (60) provides compounds of formula (61). Mono-protected compounds of formula (61) can be treated with an appropriate reagent such as R$^6$—X, wherein R$^6$ is as defined in formula (I) and X is a leaving group such as chlorine, bromine, iodine, mesylate, or triflate, to provide compounds of formula (62). Alternatively, mono-protected compounds of formula (61), when treated with an appropriate aldehyde or ketone under reductive amination conditions, will provide compounds of formula (62). Compounds of formula (62) can be deprotected to provide compounds of formula (57).

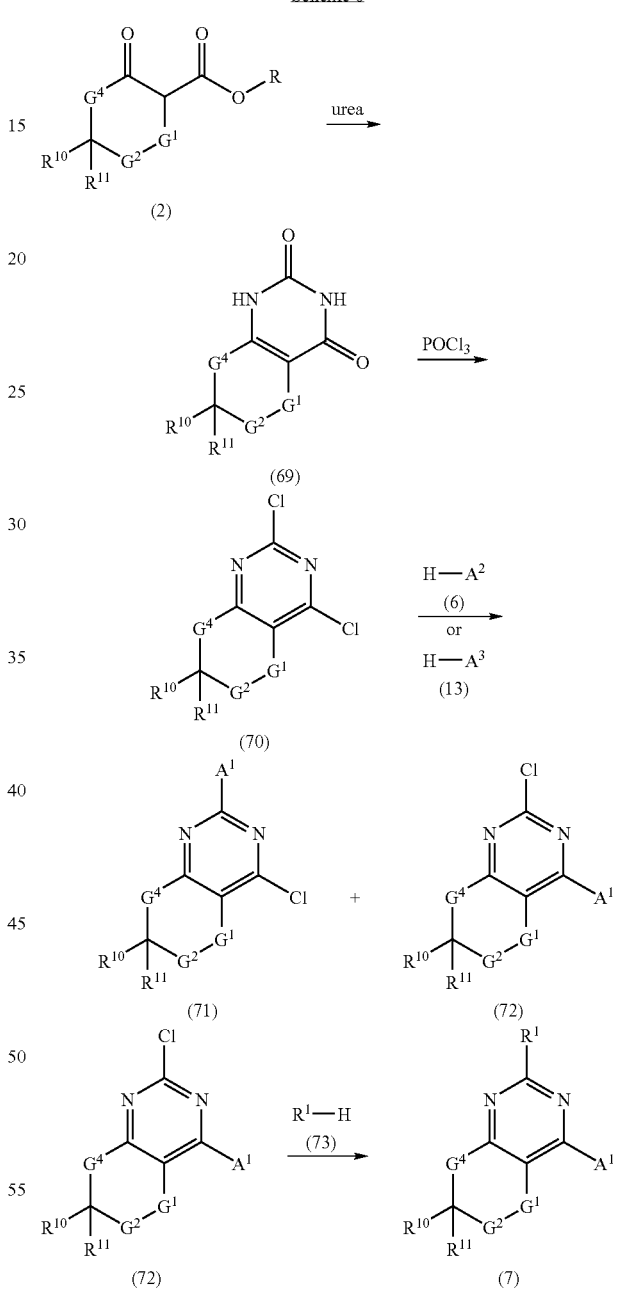

Compounds of formula (7), which are representative of compounds of the present invention wherein R$^1$, R$^{10}$, R$^{11}$, G$^1$, G$^2$, G$^4$, and A$^1$ are defined in formula (I), may be prepared as outlined in Scheme 6. Esters of formula (2), prepared as described in the above schemes, can be treated with an excess of urea and heated at 150-190° C. to provide compounds of formula (69). Compounds of formula (69) can exist as shown in the structure in Scheme 6 or in a tautomeric form. Compounds of formula (69) can be treated with POCl$_3$ with heating to provide compounds of formula (70). Compounds of formula (70) can be treated with compounds of formula (6), wherein (6) contains a primary or secondary nitrogen atom and H is a hydrogen atom on said nitrogen atom, under heated conditions in the presence or absence of a base such as triethylamine or diisopropylethylamine, in a solvent such as ethanol, 2-methoxyethanol, toluene, or acetonitrile, to provide a mixture of compounds of formula (71) and formula (72). Alternatively, compounds of formula (13) can be treated with a base such as sodium hydride or potassium carbonate in a solvent such as THF or DMF and then treated with a compound of formula (70) to provide a mixture of compounds of formula (71) and formula (72). Compounds of formula (71) and formula (72) can be separated by methods known to those skilled in the art, such as chromatography on silica gel or selective crystallization. Compounds of formula (72) can be reacted with a compound of formula (73), where $R^1$ is defined in formula (I), and where compound (73) contains an alcohol or a primary or secondary nitrogen atom and H is a hydrogen atom on said oxygen or nitrogen atom, under heated conditions in the presence or absence of a base such as triethylamine, diisopropylethylamine, or sodium hydride, in a solvent such as ethanol, 2-methoxyethanol, THF, toluene, DMF, or acetonitrile, to provide compounds of formula (7).

Compounds of formula (72) can also be treated with a catalyst such as PdCl$_2$(dppf)-CH$_2$Cl$_2$ under an atmosphere of carbon monoxide in the presence of an alcohol such as methanol in the presence of a base such as triethylamine while heating to provide compounds of formula (7), wherein $R^1$ is —(C=O)OR, wherein R is lower alkyl. Compounds of formula (7), wherein $R^1$ is —(C=O)OR, can be treated with an aqueous base such as 1 M sodium hydroxide in the presence of a solvent such as methanol to provide compounds of formula (7), wherein $R^1$ is —(C=O)OH. Compounds of formula (7), wherein $R^1$ is —(C=O)OH, can be coupled with amines under conditions known to those of ordinary skill in the art to provide compounds of formula (7), wherein $R^1$ is selected from —(C=O)—(NR$^8$R$^9$) and —(C=O)—NH-alkylene(NR$^8$R$^9$).

Compounds of formula (72) can also be treated with a reagent such as zinc cyanide, in the presence of a catalyst such as Pd(PPh$_3$)$_4$, in a solvent such as DMF, with heating, to provide compounds of formula (7), wherein $R^1$ is cyano.

Scheme 7

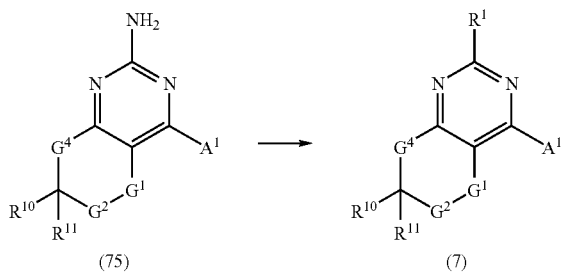

Compounds of formula (7), which are representative of compounds of the present invention wherein $R^{10}$, $R^{11}$, $G^1$, $G^2$, $G^4$, and $A^1$ are defined in formula (I), and wherein $R^1$ is limited to those compounds defined in formula (I) that are linked to the pyrimidine via a nitrogen atom, may be prepared as outlined in Scheme 7. 2-Aminopyrimidines of formula (75) can be prepared as described in the above schemes.

2-Aminopyrimidines of formula (75) can be reacted with reagents such as (alkyl-CO)$_2$O, Y'-alkyl, alkyl-CO—Y', aryl-CO—Y', Y'-alkylene(NR$^8$R$^9$), Y'—(C=O)-alkylene (NR$^8$R$^9$), and Y'-alkylene-heteroaryl, wherein Y' is a leaving group such as Cl, Br, OMs, OTs, or N-hydroxysuccinimide, optionally in the presence of a base such as Hunig's base, sodium hydride, pyridine or triethylamine, optionally in a solvent such as 2-methoxyethanol or DMF, and optionally with heating to provide compounds of formula (7), wherein $R^{10}$, $R^{11}$, $G^1$, $G^2$, $G^4$, and $A^1$ are defined in formula (I) and $R^1$ is selected from —NH(acyl), —NH(alkyl), —N(alkyl)$_2$, —NH(C=O)aryl, —NH-alkylene(NR$^8$R$^9$), —NH(C=O)-alkylene(NR$^8$R$^9$), and —NH-alkylene-heteroaryl.

Scheme 8

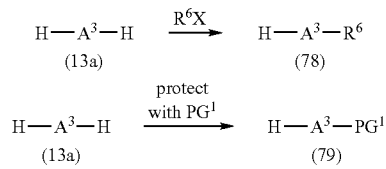

Compounds of formula (13a), wherein $A^3$ is defined in formula (I), are compounds in which one of the H groups is a proton on an oxygen or sulfur atom and the other H group is a proton on a nitrogen atom of a primary or secondary amine. Compounds of formula (13a) can be directly reacted in Scheme 3 of the above in the presence of a strong base such as sodium hydride to provide compounds of formula (7). Alternatively, compounds of formula (13a) may be treated with an appropriate reagent such as $R^6$—X, wherein X is a leaving group such as chlorine, bromine, iodine, mesylate, or triflate, to provide compounds of formula (78), wherein the nitrogen atom of (78) is substituted with $R^6$. (Scheme 8). Alternatively, mono-protected diamines of formula (13a) may be treated with an appropriate aldehyde or ketone under reductive amination conditions to provide compounds of formula (78). Conditions commonly used for reductive amination include treatment of an amine (13a) with an aldehyde or ketone in the presence of NaBH$_3$CN or NaBH(OAc)$_3$. Substituting compounds of formula (78) for compounds of formula (13) in the procedure outlined in Scheme 3 will provide compounds of formula (7A$^3$), which are representative of the present invention.

Compounds of formula (13a) may be treated with a reagent that will introduce a nitrogen protecting group (PG$^1$) on the nitrogen atom of (13a). Some typical examples of common nitrogen protecting groups include, but are not limited to, tert-butoxycarbonyl or benzyloxycarbonyl, which are introduced by treating compounds of formula (13a) with 1 equivalent of an appropriate reagent such as di-tert-butyl dicarbonate or benzyl chloroformate, respectively, to provide compounds of formula (79), wherein the protecting group (PG$^1$) is connected to the nitrogen atom. Substituting compounds of formula (79) for compounds of formula (13) in the procedure outlined in Scheme 3 will provide compounds of formula (7A$^3$), wherein the $A^3$ group of formula (7A$^3$) contains a protected nitrogen atom. This protected nitrogen atom of compounds of formula (7A$^3$) can be deprotected using conditions known to one skilled in the art, such as catalytic hydrogenation (e.g. in the presence of palladium-on-carbon in a solvent such as ethanol under an atmosphere of hydrogen) and acidic conditions (e.g. treatment with aqueous hydrochloric acid or with TFA) to provide compounds of formula (7A³), which are representative of the present invention.

Scheme 9

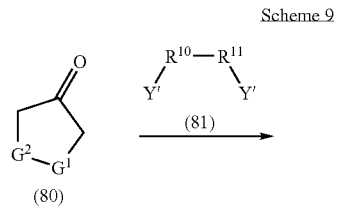

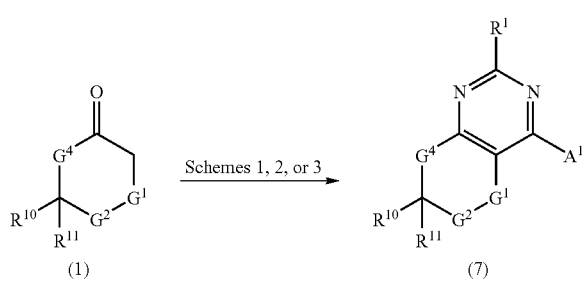

Compounds of formula (7), which are representative of compounds of the present invention wherein $R^1$, $A^1$, $G^1$, and $G^2$ are defined as in formula (I), and wherein $G^4$ is a bond and $R^{10}$ and $R^{11}$ taken together are —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, or —$CH_2CH_2OCH_2CH_2$— can be prepared as outlined in Scheme 9. Compounds of formula (80) can be reacted, with or without heat, in the presence of a base such as, but not limited to, potassium tert-butoxide or sodium hydride in a solvent such as THF with compounds of formula (81), wherein Y' is chloro, bromo, or iodo, to afford compounds of formula (1). Such reactions are known to those of ordinary skill in the art. Compounds of formula (1), when reacted as outlined in Schemes 1, 2, or 3, will provide compounds of formula (7), which are representative of compounds of the present invention.

Scheme 10

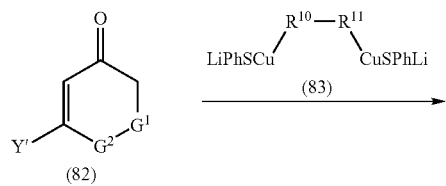

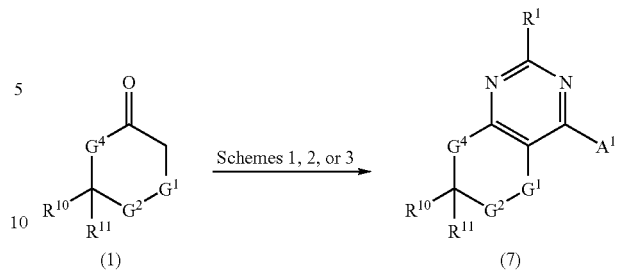

Compounds of formula (7), which are representative of compounds of the present invention wherein $R^1$, $A^1$, and $G^1$ are defined as in formula (I), and wherein $G^2$ is alkylene, $G^4$ is $CH_2$, and $R^{10}$ and $R^{11}$ taken together are —$CH_2CH_2$—, —$CH_2CH_2CH_2$—, —$CH_2CH_2CH_2CH_2$—, —$CH_2CH_2CH_2CH_2CH_2$—, or —$CH_2CH_2CH_2CH_2CH_2CH_2$—, can be prepared as outlined in Scheme 10. Compounds of formula (82), wherein Y' is chloro, bromo, or iodo, can be reacted with organobis(cuprates) of formula (83) to yield compounds of formula (1). Such reactions have been well-documented in the literature (Wender, et al, *J. Am. Chem. Soc.* 1988, 110, 2218-2223, and references cited therein). Compounds of formula (1), when reacted as outlined in Schemes 1, 2, or 3, will provide compounds of formula (7), which are representative of compounds of the present invention.

Scheme 11

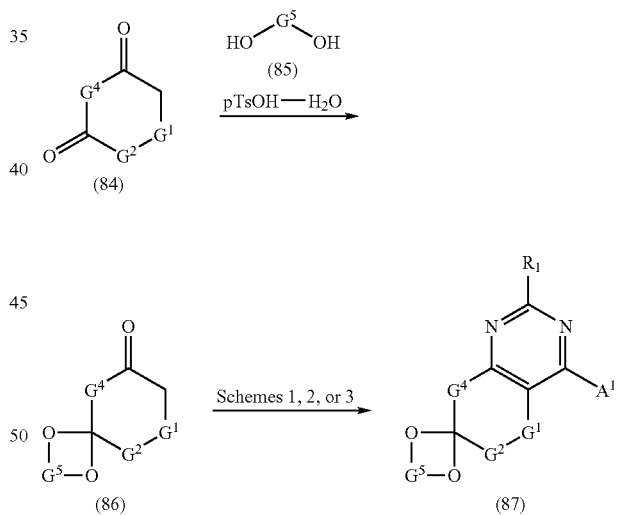

Compounds of formula (87), wherein $R^1$, $A^1$, $G^1$, and $G^4$ are defined as in formula (I), and wherein $G^2$ is alkylene and Gs is —$CH_2CH_2$— or —$CH_2CH_2CH_2$—, can be prepared as shown in Scheme 11. Compounds of formula (84) can be reacted with diols of formula (85), under Dean-Stark conditions and in the presence of para-toluenesulfonic acid, to afford compounds of formula (86). Such reactions are well-known to those of ordinary skill in the art. Processing compounds of formula (86) according to Schemes 1, 2, or 3 (substituting compounds of formula (86) for compounds of formula (1)) will then afford compounds of formula (87).

Scheme 12

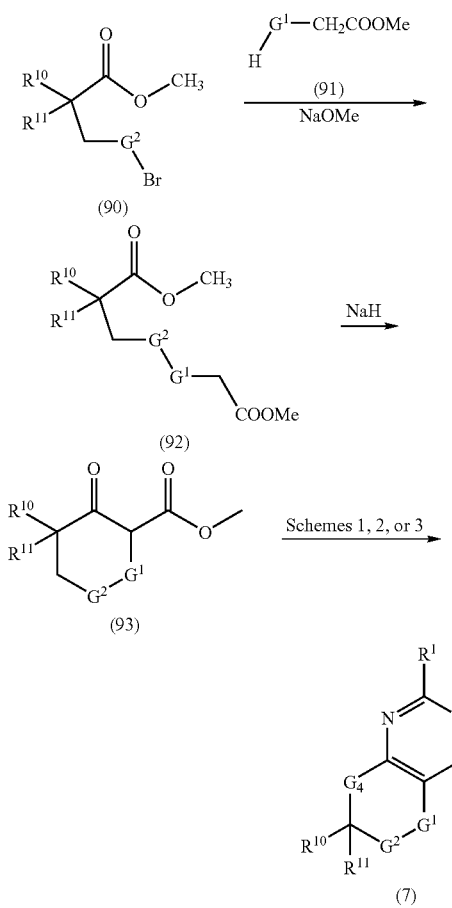

Compounds of formula (7), wherein $R^1$, $A^1$, $R^{10}$, and $R^{11}$ are defined as in formula (I), and wherein $G^4$ is a bond, $G^2$ is alkylene, and $G^1$=O, S, $NR^8$, or $NR^a$, wherein $R^a$ is hydrogen, an alkyl group, or a nitrogen protecting group such as Boc, alkylsulfonyl, arylsulfonyl, or phosphate, can be prepared as outlined in Scheme 12. Dialkylation via heating of compounds of formula (88) with compounds of formula (81), wherein Y' is a leaving group such as iodo, bromo, or chloro, in the presence of a base such as sodium hydride, in a solvent such as dioxane, can afford compounds of formula (89). Neat treatment of compounds of formula (89) with gaseous hydrogen bromide at ambient temperature, followed by reaction of the purified product with diazomethane in a solvent such as ether at 0° C., can result in compounds of formula (90). Heating of compounds of formula (91) with a base such as sodium methoxide in methanol, followed by treatment with compounds of formula (90) and subsequent heating, can afford compounds of formula (92). Heating of compounds of formula (92) with a base such as sodium hydride in a solvent such as benzene then can yield compounds of formula (93). (Similar reaction sequences can be found in the literature: e.g., Baas, et al., *Tetrahedron* 1966, 22, 285-291.) Processing of compounds of formula (93) according to the procedures outlined in Scheme 1, 2, or 3 (substituting compounds of formula (93) for compounds of formula (2)) will afford compounds of formula (7), which are representative of compounds of the present invention.

Scheme 13

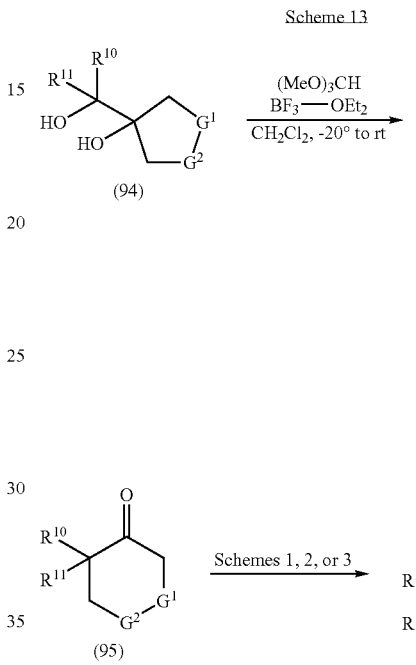

Compounds of formula (7), wherein $A^1$ and $R^1$ are defined as in formula (I), and wherein $G^1$ and $G^2$ are alkylene, $G^4$ is a bond, and $R^{10}$ and $R^1$ taken together are —CH$_2$CH$_2$CH$_2$CH$_2$—, —CH$_2$CH$_2$CH$_2$CH$_2$CH$_2$—, or —CH$_2$CH$_2$CH$_2$CH$_2$CH$_2$CH$_2$—, may be prepared according to the reaction sequence depicted in Scheme 13. Diols of formula (94), available commercially or prepared according to procedures known to those skilled in the art, can be reacted with trimethoxymethane and a Lewis acid such as boron trifluoride diethyl etherate, in a solvent such as dichloromethane, at moderately cold temperatures such as −20° C., followed by warming to room temperature, to afford compounds of formula (95). Such pinacol rearrangements are well-known to those of ordinary skill in the art. Processing of compounds of formula (95) according to the procedures outlined in Schemes 1, 2, or 3 (substituting compounds of formula (95) for compounds of formula (1)) will afford compounds of (7), which are representative of compounds of the present invention.

There are many groups of formulas (6), (6a), (13), (57), (58), (59), and (60) that are available commercially or that can be prepared as described in the scientific literature of synthetic organic chemistry. Non-exhaustive examples of diamine and aminoalcohol reagents for the synthesis of compounds of formula (I) are provided in Table 1, along with product compounds that may be produced by application of the methods in the Schemes described above (Scheme 1 through Scheme 13).

TABLE 1

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 2-Methyl-2,6-Diazaspiro[3.4]octane | 135380-30-2 | WO2004056784 A1 | 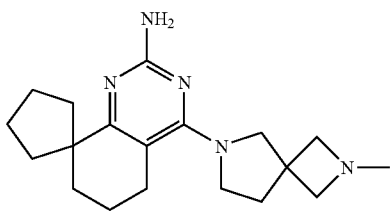<br>4-(2-methyl-2,6-diazaspiro[3.4]oct-6-yl)-6,7-dihydro-5H-benzo[6,7]cyclohepta[1,2-d]pyrimidin-2-amine |
| 7-Methyl-2,7-diazaspiro[3,5]nonane | 135380-50-6 | Frohlich, Johannes, et al. Heterocycles (1994), 37(3), 1879-91. | 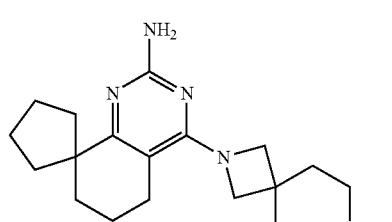<br>4-(7-methyl-2,7-diazaspiro[3.5]non-2-yl)-6,7-dihydro-5H-benzo[6,7]cyclohepta[1,2-d]pyrimidin-2-amine |
| 2,7-Diazaspiro[3.5]nonane-2-carboxylic acid, 1,1-dimethylethyl ester | 236406-55-6 | WO2005040159 A1 | 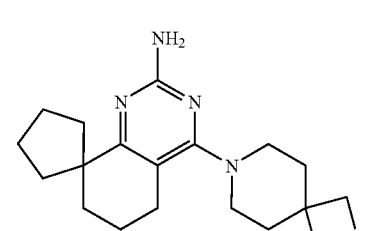<br>4'-(2,7-diazaspiro[3.5]nonan-7-yl)-6',7'-dihydro-5'H-spiro[cyclopentane-1,8'-quinazolin]-2'-amine |
| 2-(Phenylmethyl)-2,7-Diazaspiro[3.6]decane | 270257-44-8 | JP2001039950 A2 | 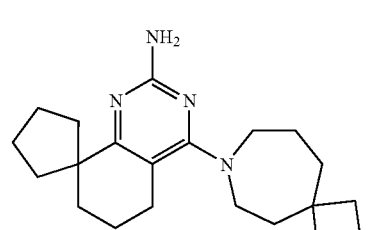<br>4'-(2,7-diazaspiro[3.6]decan-7-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 2-(Phenylmethyl)-2,7-Diazaspiro[3.6]decane | 270257-44-8 | JP2001039950 A2 | 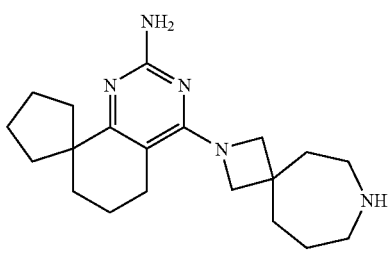 4'-(2,7-diazaspiro[3.6]decan-2-yl)-6',7'-dihydro-5'H-spiro[cyclopentane-1,8'-quinazolin]-2'-amine |
| 1-(Phenylmethyl)-1,7-diazaspiro[4.4]nonane | 128244-01-9 | Culbertson, T. P., et al. Journal of Medicinal Chemistry (1990), 33(8), 2270-5. | 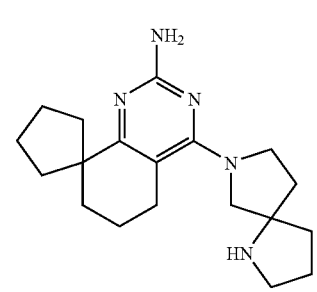 4'-(1,7-diazaspiro[4.4]nonan-7-yl)-6',7'-dihydro-5'H-spiro[cyclopentane-1,8'-quinazolin]-2'-amine |
| 1-(Phenylmethyl)-1,7-diazaspiro[4.4]nonane | 128244-01-9 | Culbertson, T. P., et al. Journal of Medicinal Chemistry (1990), 33(8), 2270-5. | 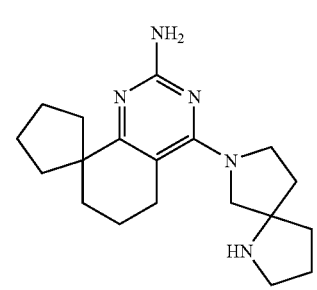 4'-(1,7-diazaspiro[4.4]nonan-7-yl)-6',7'-dihydro-5'H-spiro[cyclopentane-1,8'-quinazolin]-2'-amine |
| 2,7-Diazaspiro[4.4]nonane | 175-96-2 | Culbertson, T. P., et al. Journal of Medicinal Chemistry (1990), 33(8), 2270-5. | 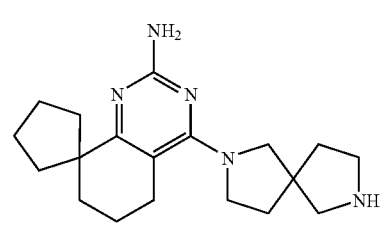 4'-(2,7-diazaspiro[4.4]nonan-2-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 1-(Phenylmethyl)-1,7-diazaspiro[4.5]decane | 867009-85-6 | WO2005097794 A1 | 4′-(1,7-diazaspiro[4.5]decan-7-yl)-6′,7′-dihydro-5′H-spiro[cyclopentane-1,8′-quinazolin]-2′-amine |
| 1-(Phenylmethyl)-1,7-diazaspiro[4.5]decane | 867009-85-6 | WO2005097794 A1 | 4′-(1,7-diazaspiro[4.5]decan-1-yl)-6′,7′-dihydro-5′H-spiro[cyclopentane-1,8′-quinazolin]-2′-amine |
| 2-Ethyl-2,8-Diazaspiro[4.5]decane | 64097-83-2 | Suess, Rudolf. Helvetica Chimica Acta (1977), 60(5), 1650-6 | 4′-(2-ethyl-2,8-diazaspiro[4.5]decan-8-yl)-6′,7′-dihydro-5′H-spiro[cyclopentane-1,8′-quinazolin]-2′-amine |
| 2,8-Diazaspiro[4.5]decane-8-carboxylic acid, 1,1-dimethylethyl ester | 236406-39-6 | US2006019985 A1 | 4′-(2,8-diazaspiro[4.5]decan-2-yl)-6′,7′-dihydro-5′H-spiro[cyclopentane-1,8′-quinazolin]-2′-amine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
| --- | --- | --- | --- |
| (R)-1,8-Diazaspiro[5.5]undecane | 151746-68-8 | Zhu, Jieping; et al. Journal of Organic Chemistry (1993), 58(23), 6451-6 | 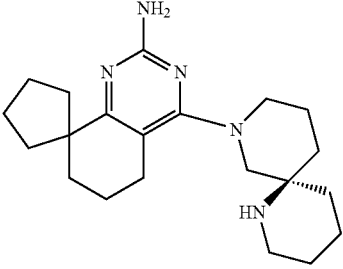<br>(R)-4'-(1,8-diazaspiro[5.5]undecan-8-yl)-6',7'-dihydro-5'H-spiro[cyclopentane-1,8'-quinazolin]-2'-amine |
| (R)-1,8-Diazaspiro[5.5]undecane | 151746-68-8 | Zhu, Jieping; et al. Journal of Organic Chemistry (1993), 58(23), 6451-6 | 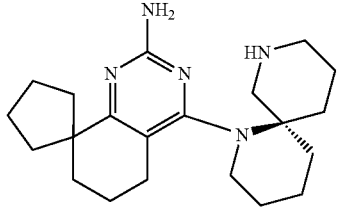<br>(R)-4'-(1,8-diazaspiro[5.5]undecan-1-yl)-6',7'-dihydro-5'H-spiro[cyclopentane-1,8'-quinazolin]-2'-amine |
| 2,8-Diazaspiro[5.5]undecane | 180-50-7 | US2005084446 A1 | 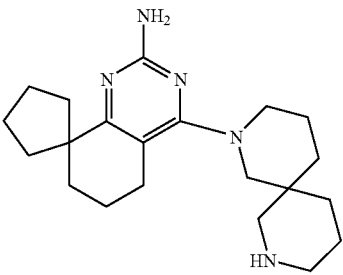<br>4'-(2,8-diazaspiro[5.5]undecan-2-yl)-6',7'-dihydro-5'H-spiro[cyclopentane-1,8'-quinazolin]-2'-amine |
| 3,9-Diazaspiro[5.5]undecane-3-carboxylic acid, 1,1-dimethylethyl ester | 173405-78-2 | WO2005040167 A1 | 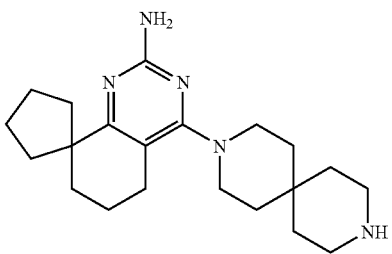<br>4'-(3,9-diazaspiro[5.5]undecan-3-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 2,5-Diazabicyclo[2.2.0]hexane | 186-07-2 | Krivdin, L. B.; et al. Russian Journal of Organic Chemistry (Translation of Zhurnal Organicheskoi Khimii) (2003), 39(5), 698-704 | 4'-(2,5-diazabicyclo[2.2.0]hexan-2-yl)-6',7'-dihydro-5'H-spiro[cyclopentane-1,8'-quinazolin]-2'-amine |
| 6-(Phenylmethyl)-2,6-diazabicyclo[3.2.0]heptane | 851526-88-0 | US2005101602 A1 | 4'-(2,6-diazabicyclo[3.2.0]heptan-2-yl)-6',7'-dihydro-5'H-spiro[cyclopentane-1,8'-quinazolin]-2'-amine |
| 6-(Phenylmethyl)-2,6-diazabicyclo[3.2.0]heptane | 851526-88-0 | US2005101602 A1 | 4'-(2,6-diazabicyclo[3.2.0]heptan-6-yl)-6',7'-dihydro-5'H-spiro[cyclopentane-1,8'-quinazolin]-2'-amine |
| tert-Butyl 3,7-diazabicyclo[4.2.0]octane-3-carboxylate | 885271-67-0 | MILESTONE PharmTec LLC 100 Jersey Avenue Building D, Box D-4 New Brunswick, NJ 08901 USA www.milestonepharmtech.com cat # 6M-0032 | 4'-(3,7-diazabicyclo[4.2.0]octan-7-yl)-6',7'-dihydro-5'H-spiro[cyclopentane-1,8'-quinazolin]-2'-amine |
| tert-Butyl 3,7-diazabicyclo[4.2.0]octane-7-carboxylate | 885271-73-8 | MILESTONE PharmTec LLC cat # 6M-0030 | 4'-(3,7-diazabicyclo[4.2.0]octan-3-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| ,8-Diazabicyclo[4.2.0]octane-8-carboxylic acid, 1,1-dimethylethyl ester | 848591-80-0 | US2005101602 A1 | 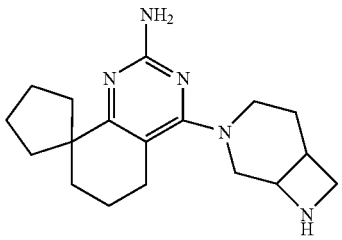<br>4'-(3,8-diazabicyclo[4.2.0]octan-3-yl)-6',7'-dihydro-5'H-spiro[cyclopentane-1,8'-quinazolin]-2'-amine |
| ,8-Diazabicyclo[4.2.0]octane-8-carboxylic acid, 1,1-dimethylethyl ester | 848591-80-0 | US2005101602 A1 | 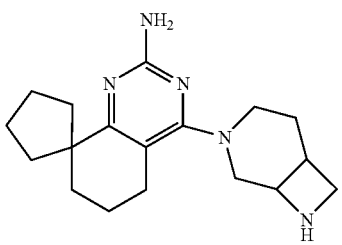<br>4'-(3,8-diazabicyclo[4.2.0]octan-3-yl)-6',7'-dihydro-5'H-spiro[cyclopentane-1,8'-quinazolin]-2'-amine |
| Octahydro-pyrrolo[3,2-b]pyrrole | 5839-99-6 | U.S. Pat. No. 2,932,650 | 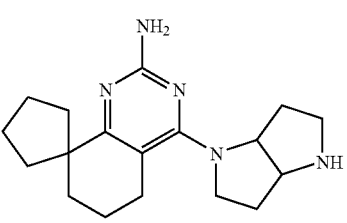<br>4'-(hexahydropyrrolo[3,2-b]pyrrol-1(2H)-yl)-6',7'-dihydro-5'H-spiro[cyclopentane-1,8'-quinazolin]-2'-amine |
| Hexahydro-pyrrolo[3,4-b]pyrrole-1-carboxylic acid tert-butyl ester | 185693-02-1 | ANICHEM LLC 7 Deer Park Drive Suite M6 Monmouth Junction, NJ 08852 www.anichemllc.com catalog # A21583 | 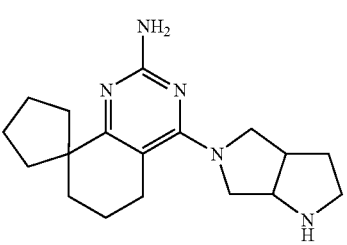<br>4'-(hexahydropyrrolo[3,4-b]pyrrol-5(1H)-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Hexahydro-pyrrolo[3,4-b]pyrrole-1-carboxylic acid tert-butyl ester | 185693-02-1 | ANICHEM LLC cat # A21583 | 4'-(hexahydropyrrolo[3,4-b]pyrrol-1(2H)-yl)-6',7'-dihydro-5'H-spiro[cyclopentane-1,8'-quinazolin]-2'-amine |
| 1H-Pyrrolo[3,2-c]pyridine, octahydro-1-methyl-, dihydrochloride | 172281-71-9 | U.S. Pat. No. 5,442,044 A | 4'-(1-methyltetrahydro-1H-pyrrolo[3,2-c]pyridin-5(6H,7H,7aH)-yl)-6',7'-dihydro-5'H-spiro[cyclopentane-1,8'-quinazolin]-2'-amine |
| 1H-Pyrrolo[2,3-c]pyridine-1-carboxylic acid, octahydro-, 1,1-dimethylethyl ester | 169750-88-3 | WO9510519A1 | 4'-(tetrahydro-1H-pyrrolo[2,3-c]pyridin-6(2H,7H,7aH)-yl)-6',7'-dihydro-5'H-spiro[cyclopentane-1,8'-quinazolin]-2'-amine |
| 1H-Pyrrolo[2,3-c]pyridine-1-carboxylic acid, octahydro-, 1,1-dimethylethyl ester | 169750-88-3 | WO9510519A1 | 4'-(tetrahydro-1H-pyrrolo[2,3-c]pyridin-6(2H,7H,7aH)-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Octahydro-6-(phenylmethyl)-1H-pyrrolo[3,4-b]pyridine | 128740-14-7 | TYGER (Aagile Labs Division of Tyger Scientific) 324 Stokes Ave. Ewing, NJ 08638 USA cat #B64518 | 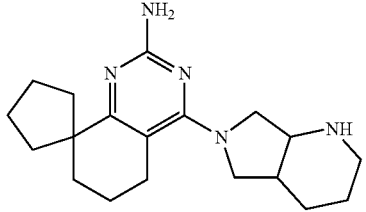<br>4′-(tetrahydro-1H-pyrrolo[3,4-b]pyridin-6(2H,7H,7aH)-yl)-6′,7′-dihydro-5′H-spiro[cyclopentane-1,8′-quinazolin]-2′-amine |
| Octahydro-6-(phenylmethyl)-1H-pyrrolo[3,4-b]pyridine | 128740-14-7 | TYGER (Aagile Labs Division of Tyger Scientific) 324 Stokes Ave. Ewing, NJ 08638 USA cat #B64518 | 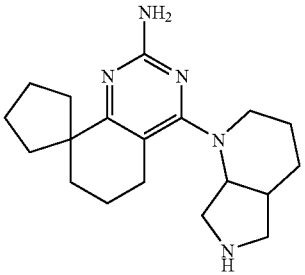<br>4′-(octahydro-1H-pyrrolo[3,4-b]pyridin-1-yl)-6′,7′-dihydro-5′H-spiro[cyclopentane-1,8′-quinazolin]-2′-amine |
| 5H-Pyrrolo[3,4-c]pyridine-5-carboxylic acid, octahydro-, 1,1-dimethylethyl ester | 351370-99-5 | TYGER (Aagile Labs Division of Tyger Scientific) 324 Stokes Ave. Ewing, NJ 08638 USA) cat # B64520 | 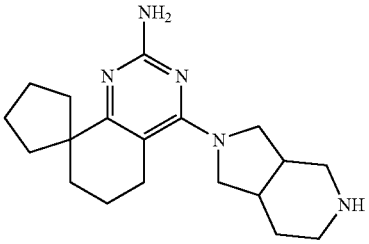<br>4′-(1H-pyrrolo[3,4-c]pyridin-2(3H,3aH,4H,5H,6H,7H,7aH)-yl)-6′,7′-dihydro-5′H-spiro[cyclopentane-1,8′-quinazolin]-2′-amine |
| Octahydro-2-(phenylmethyl)-1H-pyrrolo[3,4-c]pyridine | 351370-98-4 | TYGER (Aagile Labs Division of Tyger Scientific) 324 Stokes Ave. Ewing, NJ 08638 USA) cat # B64521 | 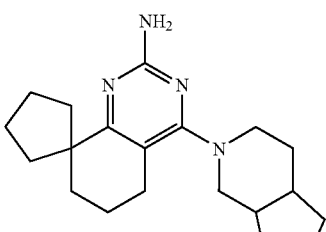<br>4′-(tetrahydro-1H-pyrrolo[3,4-c]pyridin-5(6H,7H,7aH)-yl)-6′,7′-dihydro-5′H-spiro[cyclopentane-1,8′-quinazolin]-2′-amine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| Pyrrolo[3,4-c]azepine-2(1H)-carboxylic acid, octahydro-5-(phenylmethyl)-, 1,1-dimethylethyl ester | 236406-58-9 | WO9940070A1 | 4'-(octahydropyrrolo[3,4-c]azepin-5(1H)-yl)-6',7'-dihydro-5'H-spiro[cyclopentane-1,8'-quinazolin]-2'-amine |
| Pyrrolo[3,4-c]azepine-2(1H)-carboxylic acid, octahydro-5-(phenylmethyl)-, 1,1-dimethylethyl ester | 236406-58-9 | WO9940070A1 | 4'-(octahydropyrrolo[3,4-c]azepin-2(1H)-yl)-6',7'-dihydro-5'H-spiro[cyclopentane-1,8'-quinazolin]-2'-amine |
| Pyrrolo[3,4-d]azepine-2(1H)-carboxylic acid, octahydro-6-(phenylmethyl)-, 1,1-dimethylethyl ester | 801253-06-5 | WO2004103992 A1 | 4'-(octahydropyrrolo[3,4-d]azepin-2(1H)-yl)-6',7'-dihydro-5'H-spiro[cyclopentane-1,8'-quinazolin]-2'-amine |
| Pyrrolo[3,4-d]azepine-2(1H)-carboxylic acid, octahydro-6-(phenylmethyl)-, 1,1-dimethylethyl ester | 801253-06-5 | WO2004103992 A1 | 4'-(octahydropyrrolo[3,4-d]azepin-6(7H)-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| (4aS,8aS)-1,5-Naphthyridine, decahydro-1-(phenylmethyl)- | 574001-72-2 | Li, Xiaolin; et al. Journal of Organic Chemistry (2003), 68(14), 5500-5511. | 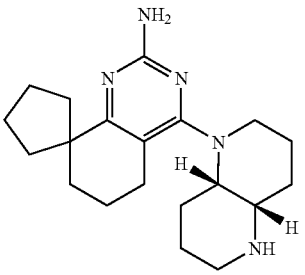<br>4′-((4aS,8aS)-octahydro-1,5-naphthyridin-1(2H)-yl)-6′,7′-dihydro-5′H-spiro[cyclopentane-1,8′-quinazolin]-2′-amine |
| (4aR,8aR)-1,5-Naphthyridine, decahydro-1-methyl- | 381227-92-5 | Li, Xiaolin, et al. Journal of Organic Chemistry (2003), 68(14), 5500-5511. | 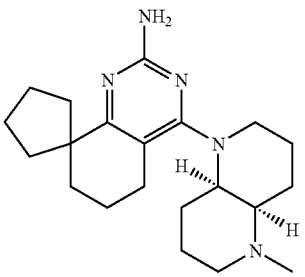<br>4′-((4aR,8aR)-5-methyloctahydro-1,5-naphthyridin-1(2H)-yl)-6′,7′-dihydro-5′H-spiro[cyclopentane-1,8′-quinazolin]-2′-amine |
| (4aR,8aR)-1,6-Naphthyridine-6(2H)-carboxylic acid, octahydro-1-(phenylmethyl)-, 1,1-dimethylethyl ester | 616875-95-7 | Kobashi, Seiichi; et al. Yakugaku Zasshi (2003), 123(5), 337-347. | 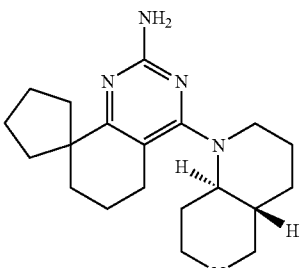<br>4′-((4aR,8aR)-octahydro-1,6-naphthyridin-1(2H)-yl)-6′,7′-dihydro-5′H-spiro[cyclopentane-1,8′-quinazolin]-2′-amine |
| (4aR,8aR)-1,6-Naphthyridine-6(2H)-carboxylic acid, octahydro-1-(phenylmethyl)-, 1,1-dimethylethyl ester | 616875-95-7 | Kobashi, Seiichi, et al. Yakugaku Zasshi (2003), 123(5), 337-347. | 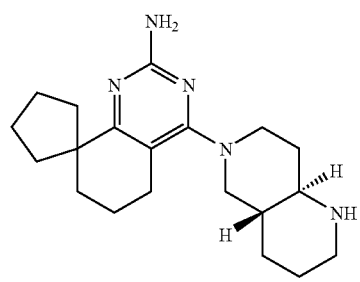<br>4′-((4aR,8aR)-octahydro-1,6-naphthyridin-6(7H)-yl)-6′,7′-dihydro-5′H-spiro[cyclopentane-1,8′-quinazolin]-2′-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Decahydro-6-methyl-1,6-naphthyridine | 135037-28-4 | MicroChemistry Building Blocks MicroChemistry Ltd., Kosygina St. 4, Moscow, 119993; Russia; Email: sale@mch.ru; Web: http://www.mch.ru cat # mch-bb-2003 11276 | 4'-(6-methyloctahydro-1,6-naphthyridin-1(2H)-yl)-6',7'-dihydro-5'H-spiro[cyclopentane-1,8'-quinazolin]-2'-amine |
| trans-Decahydro-1,7-Naphthyridine | 13623-82-0 | Hanus, Vladimir; et al. Organic Mass Spectrometry (1984), 19(9), 459-60. | 4'-((4aS,8aR)-octahydro-1,7-naphthyridin-1(2H)-yl)-6',7'-dihydro-5'H-spiro[cyclopentane-1,8'-quinazolin]-2'-amine |
| trans-Decahydro-1,7-Naphthyridine | 13623-82-0 | Hanus, Vladimir; et al. Organic Mass Spectrometry (1984), 19(9), 459-60. | 4'-((4aS,8aR)-octahydro-1,7-naphthyridin-7(1H)-yl)-6',7'-dihydro-5'H-spiro[cyclopentane-1,8'-quinazolin]-2'-amine |
| 2,7-Naphthyridine-2(1H)-carboxylic acid, octahydro-, 1,1-dimethylethyl ester | 885270-18-8 | MILESTONE PharmTec LLC cat # 6M-0007 | 4'-(octahydro-2,7-naphthyridin-2(1H)-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 8a-Ethyldecahydro-copyrine | 873999-52-1 | Iselin, B. M.; et al. Journal of the American Chemical Society (1954), 76 3220-2. | 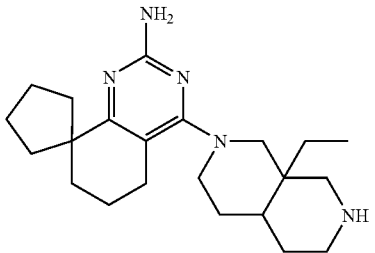<br>4'-(8a-ethyloctahydro-2,7-naphthyridin-2(1H)-yl)-6',7'-dihydro-5'H-spiro[cyclopentane-1,8'-quinazolin]-2'-amine |
| decahydro-1H-Pyrido[3,2-c]azepine | 344460-81-7 | Linden, Anthony; et al. Acta Crystallographica, Section C: Crystal Structure Communications (2001), C57(6), 764-766. | 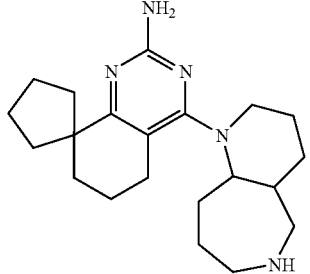<br>4'-(decahydro-1H-pyrido[3,2-c]azepin-1-yl)-6',7'-dihydro-5'H-spiro[cyclopentane-1,8'-quinazolin]-2'-amine |
| Decahydro-1H-Pyrido[3,2-c]azepine | 344460-81-7 | Linden, Anthony; et al. Acta Crystallographica, Section C: Crystal Structure Communications (2001), C57(6), 764-766. | 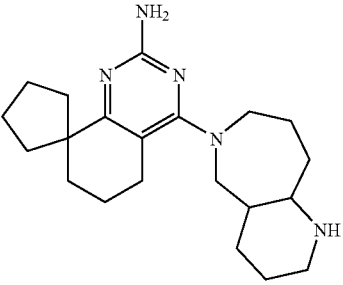<br>4'-(tetrahydro-1H-pyrido[3,2-c]azepin-6(2H,7H,8H,9H,9aH)-yl)-6',7'-dihydro-5'H-spiro[cyclopentane-1,8'-quinazolin]-2'-amine |
| Octahydro-3-isobutyl-pyrrolo[1,2-a]pyrazine | 718631-71-1 | Chemstep Product List 20 Avenue Victor Hugo; Carbon Blanc, 33560; France; Email: info@chemstep.com; Web: http://www.chemstep.com cat # 71454 | 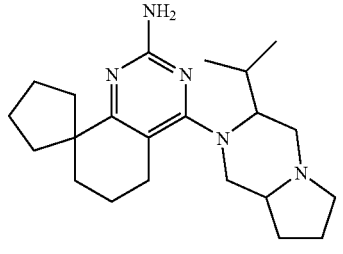<br>4'-(3-isopropylhexahydropyrrolo[1,2-a]pyrazin-2(1H)-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Octahydro-1-methyl-pyrrolo[1,2-a]pyrazine | 155206-39-6 | WO2006048750 A2 | 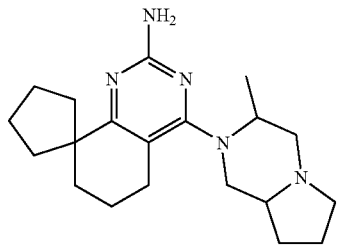<br>4'-(3-methylhexahydropyrrolo[1,2-a]pyrazin-2(1H)-yl)-6',7'-dihydro-5'H-spiro[cyclopentane-1,8'-quinazolin]-2'-amine |
| Octahydro-6-methyl-pyrrolo[1,2-a]pyrazine | 22177-06-6 | Ponomarev, A. A.; Set al. Metody Polucheniya Khimicheskikh Reaktivov i Preparativ (1967), (17), 5-6 | 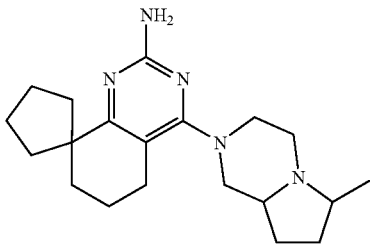<br>4'-(6-methylhexahydropyrrolo[1,2-a]pyrazin-2(1H)-yl)-6',7'-dihydro-5'H-spiro[cyclopentane-1,8'-quinazolin]-2'-amine |
| Octahydro-6-methyl-2H-Pyrido[1,2-a]pyrazine | 5762-99-2 | Chemstep Product List cat # 70166 | 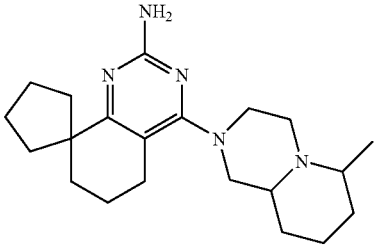<br>4'-(6-methyldihydro-1H-pyrido[1,2-a]pyrazin-2(6H,7H,8H,9H,9aH)-yl)-6',7'-dihydro-5'H-spiro[cyclopentane-1,8'-quinazolin]-2'-amine |
| Octahydro-pyrido[1,2-a]pyrazine | 4430-75-5 | Oakwood Products Catalog cat # 032054 | 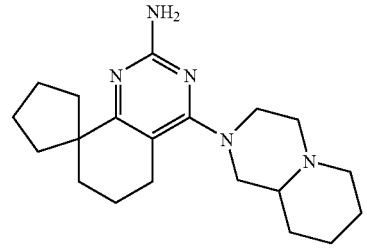<br>4'-(dihydro-1H-pyrido[1,2-a]pyrazin-2(6H,7H,8H,9H,9aH)-yl)-6',7'-dihydro-5'H-spiro[cyclopentane-1,8'-quinazolin]-2'-amine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| Octahydro-1H-Pyrrolo[1,2-a][1,4]diazepine | 109324-83-6 | MicroChemistry Building Blocks cat # mch-bb-2003 13717 | 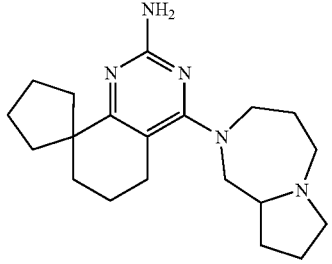 4'-(dihydro-1H-pyrrolo[1,2-a][1,4]diazepin-2(3H,7H,8H,9H,9aH)-yl)-6',7'-dihydro-5'H-spiro[cyclopentane-1,8'-quinazolin]-2'-amine |
| Decahydro-pyrazino[1,2-a]azepine | 49633-80-9 | Oakwood Products 1741 Old Dunbar Rd.; West Columbia, SC, 29172; USA; Email: sales@fluorochemusa.com; Web: http://www.oakwoodchemical.com Catalog cat # 032087 | 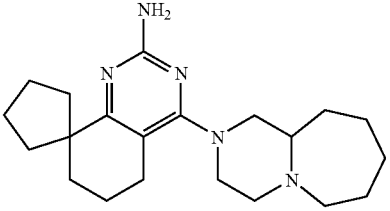 4'-(octahydropyrazino[1,2-a]azepin-2(1H)-yl)-6',7'-dihydro-5'H-spiro[cyclopentane-1,8'-quinazolin]-2'-amine |
| Octahydro-1H-Cyclopentapyrazine | 154393-81-4 | Chemstep Product List cat # 53753 | 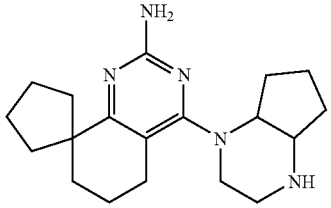 4'-(octahydro-1H-cyclopenta[b]pyrazin-1-yl)-6',7'-dihydro-5'H-spiro[cyclopentane-1,8'-quinazolin]-2'-amine |
| Decahydro-quinoxaline | 90410-24-5 | MicroChemistry Building Blocks cat # mch-bb-2003 11269 | 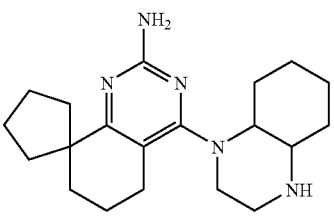 4'-(octahydroquinoxalin-1(2H)-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Decahydro-2-methyl-quinoxaline, dihydrochloride | 114062-34-9 | Maffei, Silvio; et al. Gazzetta Chimica Italiana (1958), 88 556-63. | 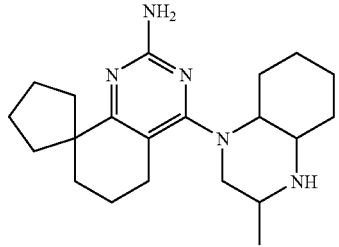<br>4'-(3-methyloctahydroquinoxalin-1(2H)-yl)-6',7'-dihydro-5'H-spiro[cyclopentane-1,8'-quinazolin]-2'-amine |
| Octahydro-3,3,7,7-tetramethyl-5-diazocine | 17288-14-1 | Kemp, D. S.; et al. Journal of Organic Chemistry (1979), 44(25), 4473-6. | 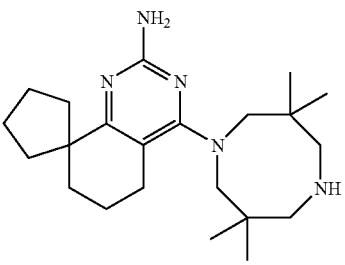<br>4'-(3,3,7,7-tetramethyl-1,5-diazocan-1-yl)-6',7'-dihydro-5'H-spiro[cyclopentane-1,8'-quinazolin]-2'-amine |
| Octahydro-1-methyl-1,5-diazocine, dihydrobromide | 4318-35-8 | U.S. Pat. No. 3,247,206 | 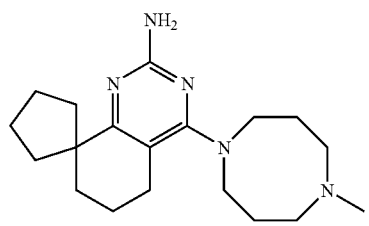<br>4'-(5-methyl-1,5-diazocan-1-yl)-6',7'-dihydro-5'H-spiro[cyclopentane-1,8'-quinazolin]-2'-amine |
| Octahydro-1H-1,5-diazonine, dihydrochloride | 118872-68-7 | Stetter, H.; et al. Chemische Berichte (1958), 91 1982-8. | 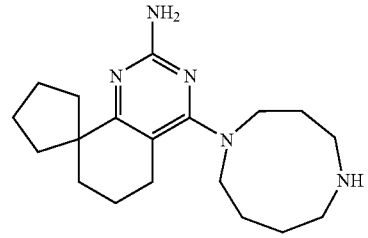<br>4'-(1,5-diazonan-1-yl)-6',7'-dihydro-5'H-spiro[cyclopentane-1,8'-quinazolin]-2'-amine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| Decahydro-1,6-diazecine, dihydrochloride | 118725-33-0 | Stetter, H.; et al. Chemische Berichte (1958), 91 1982-8. | 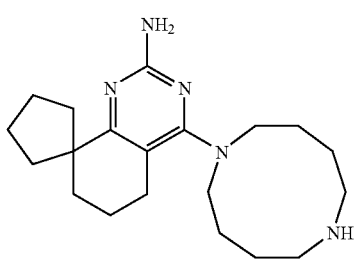<br>4'-(1,6-diazecan-1-yl)-6',7'-dihydro-5'H-spiro[cyclopentane-1,8'-quinazolin]-2'-amine |
| Decahydro-1-methyl-1,6-diazecine | 68388-04-5 | Horner, L.; et al. Justus Liebigs Annalen der Chemie (1978), (9), 1505-17. | 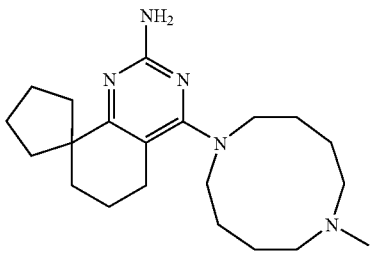<br>4'-(6-methyl-1,6-diazecan-1-yl)-6',7'-dihydro-5'H-spiro[cyclopentane-1,8'-quinazolin]-2'-amine |
| Decahydro-1,5-diazecine | 6573-62-2 | Bergmann, D. J.; et al. Chemical Communications (1999), (14), 1279-1280. | 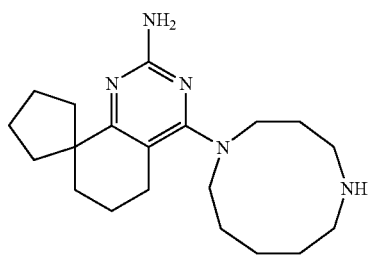<br>4'-(1,5-diazecan-1-yl)-6',7'-dihydro-5'H-spiro[cyclopentane-1,8'-quinazolin]-2'-amine |
| 1,6-Diazacycloundecane | 294-51-9 | Stetter, H.; et al. Chemische Berichte (1958), 91 677-80. | 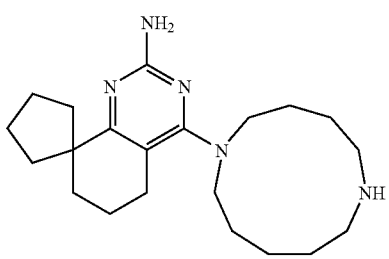<br>4'-(1,6-diazacycloundecan-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Azetidin-3-ylmethyl-carbamic acid tert-butyl ester | 91188-15-7 | TYGER (Aagile Labs Division of Tyger Scientific) 324 Stokes Ave. Ewing, NJ 08638 USA) cat # A58187 | 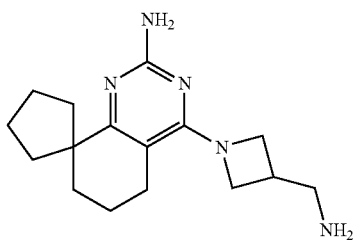<br>4'-(3-(aminomethyl)azetidin-1-yl)-6',7'-dihydro-5'H-spiro[cyclopentane-1,8'-quinazolin]-2'-amine |
| (3-Pyrrolidinyl-methyl)-carbamic acid tert-butyl ester | 149366-79-0 | TYGER (Aagile Labs Division of Tyger Scientific) 324 Stokes Ave. Ewing, NJ 08638 USA) cat # B64504 | 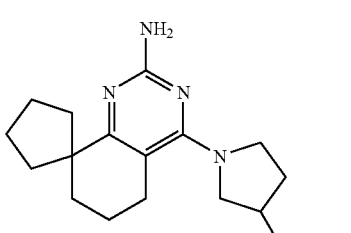<br>4'-(3-(aminomethyl)pyrrolidin-1-yl)-6',7'-dihydro-5'H-spiro[cyclopentane-1,8'-quinazolin]-2'-amine |
| (3R)-3-((Dimethyl-amino)methyl) pyrrolidine dihydrochloride | 859213-49-3 | WO2005082855 A1 | 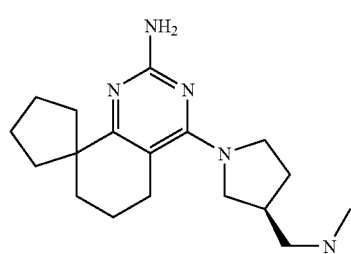<br>(S)-4'-(3-((dimethylamino)methyl)pyrrolidin-1-yl)-6',7'-dihydro-5'H-spiro[cyclopentane-1,8'-quinazolin]-2'-amine |
| Piperidin-4-ylmethyl-carbamic acid tert-butyl ester | 135632-53-0 | Fluorochem Ltd.; Wesley Street; Old Glossop, Derbyshire, SK13 7RY; United Kingdom; Email: enquiries@fluorochem.co.uk; Web: http://www.fluorochem.net cat # 17246 | 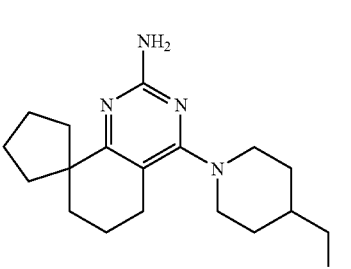<br>4'-(4-(aminomethyl)piperidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Dimethyl-(2-piperidin-4-yl-ethyl)-amine | 102308-48-5 | MATRIX (Matrix Scientific, P O Box 25067; Columbia, SC, 29224-5067 USA; Email: sales@matrixscientific.com; Web: http://www.matrixscientific.com) cat # 020420 | 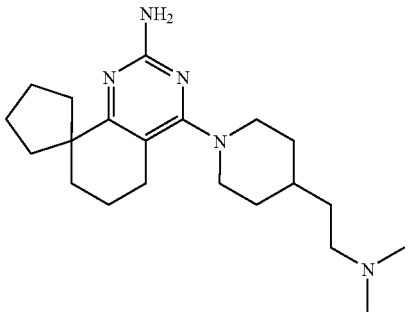 4′-(4-(2-(dimethylamino)ethyl)piperidin-1-yl)-6′,7′-dihydro-5′H-spiro[cyclopentane-1,8′-quinazolin]-2′-amine |
| 3-N-Boc-aminomethyl piperidine | 142643-29-6 | ALDRICH (Aldrich Chemical Company, Inc. 1001 West Saint Paul Avenue Milwaukee, WI 53233 USA) cat # 653896 | 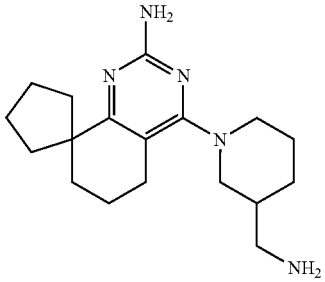 4′-(3-(aminomethyl)piperidin-1-yl)-6′,7′-dihydro-5′H-spiro[cyclopentane-1,8′-quinazolin]-2′-amine |
| 3-(2-Boc-aminoethyl) piperidine | 215305-98-9 | TYGER (Aagile Labs Division of Tyger Scientific) 324 Stokes Ave. Ewing, NJ 08638 USA) cat # B28400 | 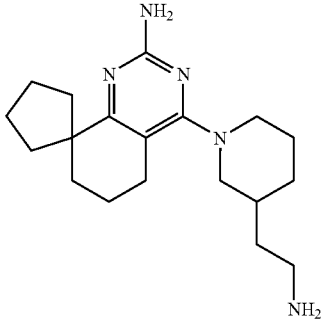 4′-(3-(2-aminomethyl)piperidin-1-yl)-6′,7′-dihydro-5′H-spiro[cyclopentane-1,8′-quinazolin]-2′-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
| --- | --- | --- | --- |
| 3-Aminomethyl-azetidine-1-carboxylic acid tert-butyl ester | 325775-44-8 | TYGER (Aagile Labs Division of Tyger Scientific) 324 Stokes Ave. Ewing, NJ 08638 USA) cat # A57126 | 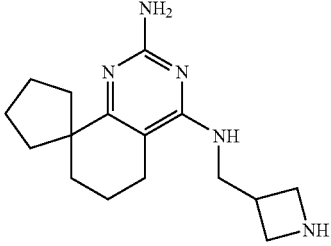<br>N4'-(azetidin-3-ylmethyl)-6',7'-dihydro-5'H-spiro[cyclopentane-1,8'-quinazoline]-2',4'-diamine |
| 3-Aminomethyl-pyrrolidine-1-carboxylic acid tert-butyl ester | 270912-72-6 | FLROCHEM cat # 11395 | 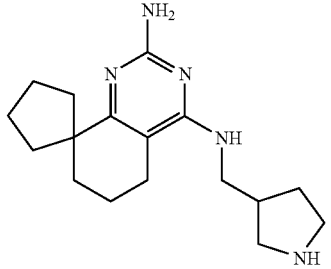<br>N4'-(pyrrolidin-3-ylmethyl)-6',7'-dihydro-5'H-spiro[cyclopentane-1,8'-quinazoline]-2',4'-diamine |
| Methyl-(1-methyl-pyrrolidin-3-ylmethyl)-amine | 89850-95-3 | MATRIX catalog # 019128 | 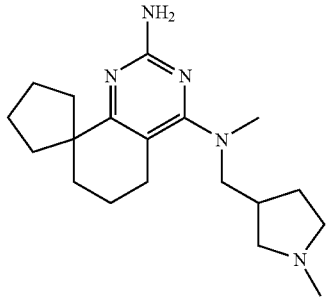<br>N4'-methyl-N4'-((1-methylpyrrolidin-3-yl)methyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 3-Aminoethyl-1-n-cbz-pyrrolidine | 811842-07-6 | OAKWOOD cat # 11381 | 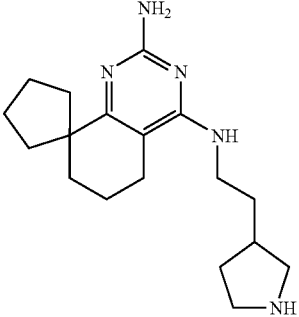 N4'-(2-(pyrrolidin-3-yl)ethyl)-6',7'-dihydro-5'H-spiro[cyclopentane-1,8'-quinazoline]-2',4'-diamine |
| 1-N-Boc-4-(aminomethyl)piperidine | 144222-22-0 | ALDRICH cat # 641472 | 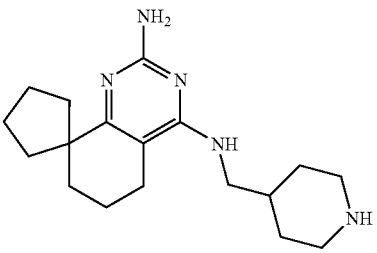 N4'-(piperidin-4-ylmethyl)-6',7'-dihydro-5'H-spiro[cyclopentane-1,8'-quinazoline]-2',4'-diamine |
| 4-(Pyrrolidin-1-ylmethyl)piperidine | 683772-11-4 | MATRIX cat # 016344 | 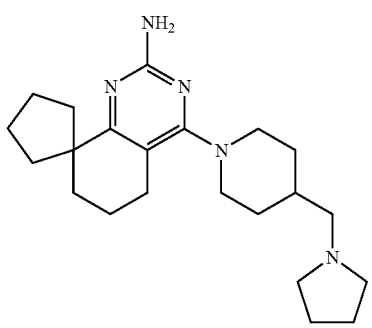 4'-(4-(pyrrolidin-1-ylmethyl)piperidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 3-(Aminomethyl)-1-N-Boc-piperidine | 162167-97-7 | OAKWOOD cat # 11388 | N4'-(piperidin-3-ylmethyl)-6',7'-dihydro-5'H-spiro[cyclopentane-1,8'-quinazoline]-2',4'-diamine |
| 4-(N-Boc-amino)piperidine | 73874-95-0 | ALDRICH cat # 540935 | 4'-(4-aminopiperidin-1-yl)-6',7'-dihydro-5'H-spiro[cyclopentane-1,8'-quinazolin]-2'-amine |
| 4-(2-Boc-aminoethyl)piperidine | 165528-81-4 | Tyger catalog # B32000 | 4'-(4-(2-aminoethyl)piperidin-1-yl)-6',7'-dihydro-5'H-spiro[cyclopentane-1,8'-quinazolin]-2'-amine |
| 3-Boc-aminopiperidine | 172603-05-3 | Tyger Scientific Product List cat # B50100 | 4'-(3-aminopiperidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| C-(1-Benzyl-piperidin-3-yl)-methylamine | 124257-62-1 | OAKWOOD cat # 30699 | 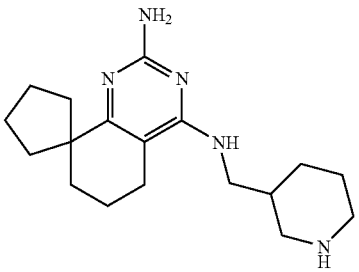<br>N4'-(piperidin-3-ylmethyl)-6',7'-dihydro-5'H-spiro[cyclopentane-1,8'-quinazoline]-2',4'-diamine |
| (1-Methyl-piperidin-4-yl)-methylamine | 7149-42-0 | OAKWOOD cat # 32204 | 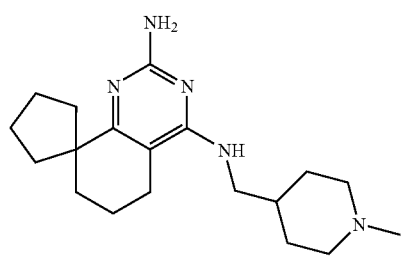<br>N4'-((1-methylpiperidin-4-yl)methyl)-6',7'-dihydro-5'H-spiro[cyclopentane-1,8'-quinazoline]-2',4'-diamine |
| (1-Isopropyl-piperidin-3-ylmethyl)-methyl-amine | 876716-01-7 | Matrix Scientific catalog # 19173 | 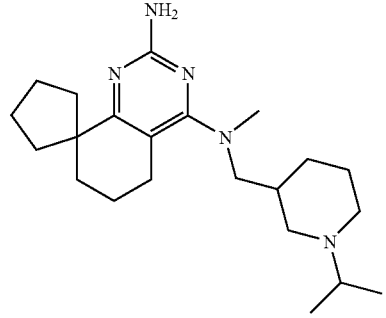<br>N4'-((1-isopropylpiperidin-3-yl)methyl)-N4'-methyl-6',7'-dihydro-5'H-spiro[cyclopentane-1,8'-quinazoline]-2',4'-diamine |
| (1-Isopropyl-piperidin-4-ylmethyl)-methyl-amine | 876716-04-0 | Matrix Scientific catalog # 19174 | 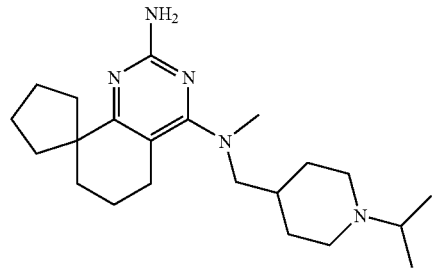<br>N4'-((1-isopropylpiperidin-4-yl)methyl)-N4'-methyl-6',7'-dihydro-5'H-spiro[cyclopentane-1,8'-quinazoline]-2',4'-diamine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| 4-(1-Azetidinylmethyl)-piperidine, dihydrochloride | 864441-51-0 | WO2005082854 A1 | 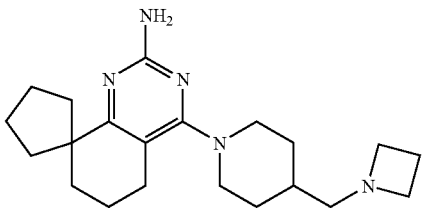<br>4'-(4-(azetidin-1-ylmethyl)piperidin-1-yl)-6',7'-dihydro-5'H-spiro[cyclopentane-1,8'-quinazolin]-2'-amine |
| 4-(1-Azetidinyl)-piperidine, dihydrochloride | 864246-02-6 | WO2005082855 A1 | 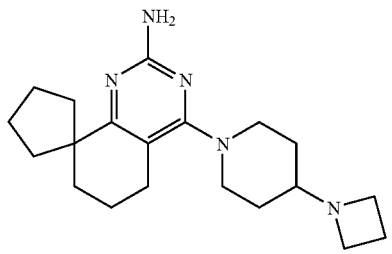<br>4'-(4-(azetidin-1-yl)piperidin-1-yl)-6',7'-dihydro-5'H-spiro[cyclopentane-1,8'-quinazolin]-2'-amine |
| 1-(3-Azetidinyl)-pyrrolidine, bis(trifluoroacetate) | 864248-58-8 | WO2005082854 A1 | 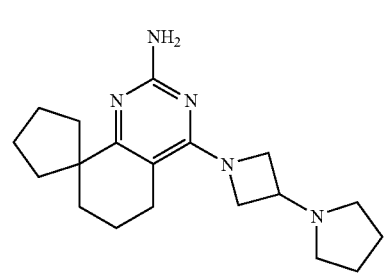<br>4'-(3-(pyrrolidin-1-yl)azetidin-1-yl)-6',7'-dihydro-5'H-spiro[cyclopentane-1,8'-quinazolin]-2'-amine |
| [1,3']Bipyrrolidinyl | 267241-99-6 | Oakwood Products Catalog; catalog # 031602 | 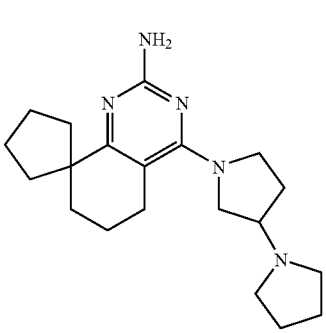<br>4'-(1,3'-bipyrrolidin-1'-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 4-(1-Pyrrolidinyl)piperidine | 5004-07-9 | Aldrich catalog # 437352 | 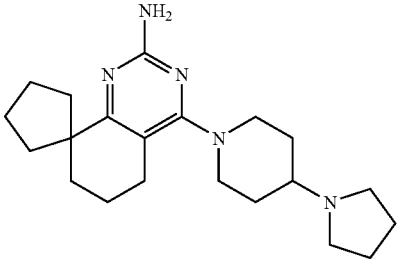 4'-(4-(pyrrolidin-1-yl)piperidin-1-yl)-6',7'-dihydro-5'H-spiro[cyclopentane-1,8'-quinazolin]-2'-amine |
| 3-Pyrrolidin-1-ylmethyl-piperidine | 514842-98-9 | Oakwood Products Catalog; catalog # 032019 | 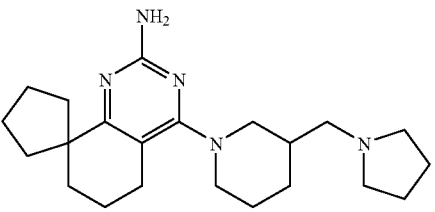 4'-(3-(pyrrolidin-1-ylmethyl)piperidin-1-yl)-6',7'-dihydro-5'H-spiro[cyclopentane-1,8'-quinazolin]-2'-amine |
| 3-[2-(1-Pyrrolidinyl)ethyl]piperidine | 122373-96-0 | DE3726908A1 | 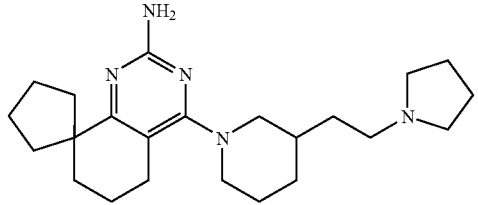 4'-(3-(2-(pyrrolidin-1-yl)ethyl)piperidin-1-yl)-6',7'-dihydro-5'H-spiro[cyclopentane-1,8'-quinazolin]-2'-amine |
| 4-(2-Pyrrolidin-1-yl-ethyl)-piperidine | 14759-08-1 | Oakwood Products Catalog; catalog # 025057 | 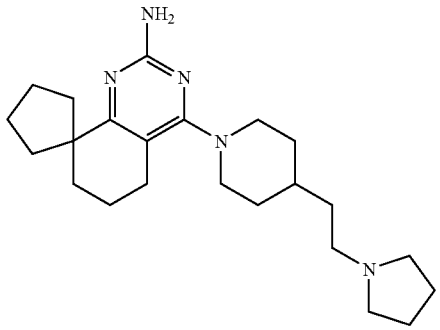 4'-(4-(2-(pyrrolidin-1-yl)ethyl)piperidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| N-Methyl-1-azetidinepropanamine | 864246-87-7 | WO2005082855 A1 | 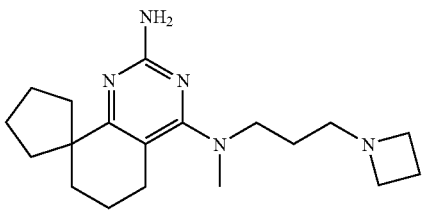 N4'-(3-(azetidin-1-yl)propyl)-N4'-methyl-6',7'-dihydro-5'H-spiro[cyclopentane-1,8'-quinazolin]-2',4'-diamine |
| N-Methyl-1-pyrrolidineethanamine | 32776-22-0 | Aurora Screening Library catalog # kec-0001338 | 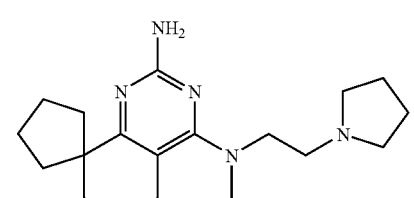 N4'-methyl-N4'-(2-(pyrrolidin-1-yl)ethyl)-6',7'-dihydro-5'H-spiro[cyclopentane-1,8'-quinazoline]-2',4'-diamine |
| Methyl[3-(pyrrolidin-1-yl)propyl]amine | 99114-68-8 | Surleraux, D. L. N. G.; et al. Journal of Medicinal Chemistry 2005, 48(6), 1965-1973. | 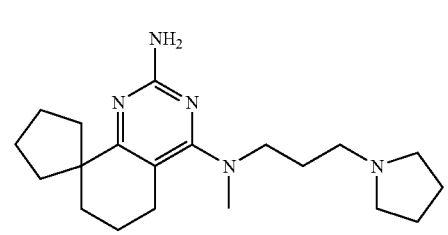 N4'-methyl-N4'-(3-(pyrrolidin-1-yl)propyl)-6',7'-dihydro-5'H-spiro[cyclopentane-1,8'-quinazoline]-2',4'-diamine |
| N-Methyl-1-pyrrolidinebutanamine | 153905-93-2 | WO2005082855 A1 | 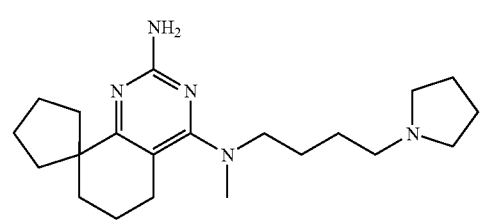 N4'-methyl-N4'-(4-(pyrrolidin-1-yl)butyl)-6',7'-dihydro-5'H-spiro[cyclopentane-1,8'-quinazoline]-2',4'-diamine |
| 2-(Azetidin-1-yl)ethylamine | 795299-77-3 | WO2006021544 A1 | 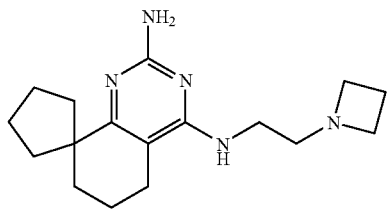 N4'-(2-(azetidin-1-yl)ethyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| N-(3-Aminopropyl) azetidine | 54262-75-8 | Murahashi, S.; et al. Journal of the American Chemical Society (1983), 105(15), 5002-11. | N4'-(3-(azetidin-1-yl)propyl)-6',7'-dihydro-5'H-spiro[cyclopentane-1,8'-quinazoline]-2',4'-diamine |
| 1-(2-Aminoethyl) pyrrolidine | 7154-73-6 | ALDRICH catalog # A55357 | N4'-(2-(pyrrolidin-1-yl)ethyl)-6',7'-dihydro-5'H-spiro[cyclopentane-1,8'-quinazoline]-2',4'-diamine |
| 1-(3-Aminopropyl) pyrrolidine | 23159-07-1 | Lancaster Synthesis catalog # 4739 | N4'-(3-(pyrrolidin-1-yl)propyl)-6',7'-dihydro-5'H-spiro[cyclopentane-1,8'-quinazoline]-2',4'-diamine |
| 4-(1-Pyrrolidino) butylamine | 24715-90-0 | Matrix Scientific catalog # 7650 | N4'-(4-(pyrrolidin-1-yl)butyl)-6',7'-dihydro-5'H-spiro[cyclopentane-1,8'-quinazoline]-2',4'-diamine |
| (1-Benzyl-azetidin-2-yl)-methylamine | 46193-94-6 | PharmLab Product List catalog # 25-0007 | N4'-(azetidin-2-ylmethyl)-6',7'-dihydro-5'H-spiro[cyclopentane-1,8'-quinazoline]-2',4'-diamine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| 2-(2-Aminoethyl)-1-methylpyrrolidine | 51387-90-7 | Aldrich catalog # 139505 | 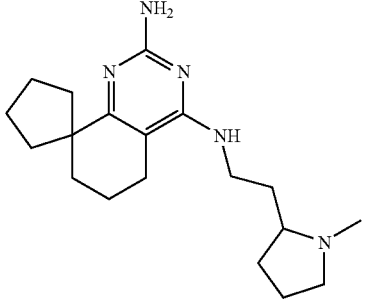<br>N4′-(2-(1-methylpyrrolidin-2-yl)ethyl)-6′,7′-dihydro-5′H-spiro[cyclopentane-1,8′-quinazoline]-2′,4′-diamine |
| 2-(Aminomethyl)-1-N-Boc-piperidine | 370069-31-1 | Fluorochem catalog # 11387 | 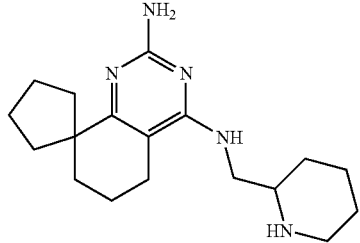<br>N4′-(piperidin-2-ylmethyl)-6′,7′-dihydro-5′H-spiro[cyclopentane-1,8′-quinazoline]-2′,4′-diamine |
| (+/−)-2-(Aminomethyl)-1-N-Boc-pyrrolidine | 177911-87-4 | Fluorochem catalog # 11393 | 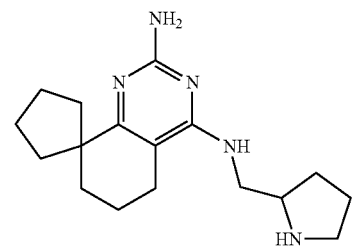<br>N4′-(pyrrolidin-2-ylmethyl)-6′,7′-dihydro-5′H-spiro[cyclopentane-1,8′-quinazoline]-2′,4′-diamine |
| 2-(Aminoethyl)-1-N-Boc-piperidine | 239482-98-5 | Fluorochem catalog # 11378 | 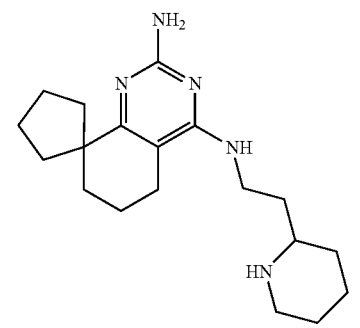<br>N4′-(2-(piperidin-2-yl)ethyl)-6′,7′-dihydro-5′H-spiro[cyclopentane-1,8′-quinazoline]-2′,4′-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 2-(3-Amino-propyl)-pyrrolidine-1-carboxylic acid tert-butyl ester | 887587-47-5 | Tyger Scientific Product List catalog # A57685 | N4'-(3-(pyrrolidin-2-yl)propyl)-6',7'-dihydro-5'H-spiro[cyclopentane-1,8'-quinazoline]-2',4'-diamine |
| 1,4-Cyclohexanediamine | 3114-70-3 | TCI-US catalog # C0814 | N4'-(4-aminocyclohexyl)-6',7'-dihydro-5'H-spiro[cyclopentane-1,8'-quinazoline]-2',4'-diamine |
| N,N-Dimethyl-cyclohexane-1,4-diamine | 42389-50-4 | PharmLab Product List catalog # 20-0268 | N4'-(4-(dimethylamino)cyclohexyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 1,3-Cyclohexanediamine | 3385-21-5 | TCI-US catalog # C0813 | 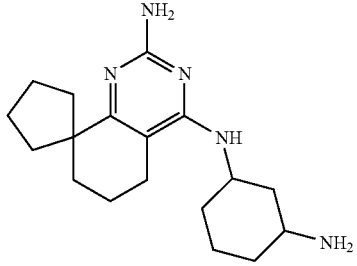 N4'-(3-aminocyclohexyl)-6',7'-dihydro-5'H-spiro[cyclopentane-1,8'-quinazoline]-2',4'-diamine |
| 1,3-Cyclopentanediamine | 73211-32-2 | Chemgenx Product List catalog # CX-01566 | 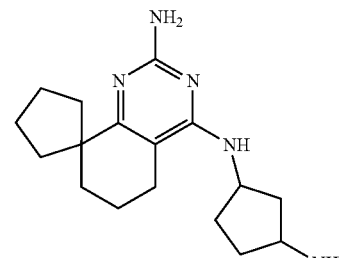 N4'-(3-aminocyclopentyl)-6',7'-dihydro-5'H-spiro[cyclopentane-1,8'-quinazoline]-2',4'-diamine |
| Benzyl trans-4-aminomethylcyclo-hexylcarbamate | 177582-74-0 | AMRI Fine Chemicals catalog # A00095 | 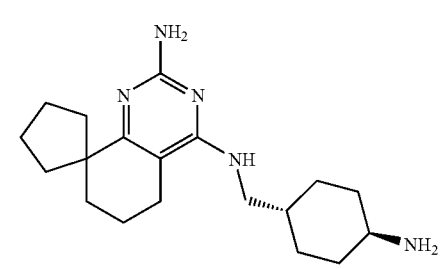 N4'-(((1r,4r)-4-aminocyclohexyl)methyl)-6',7'-dihydro-5'H-spiro[cyclopentane-1,8'-quinazoline]-2',4'-diamine |
| tert-Butyl trans-4-aminocyclohexyl-methylcarbamate | 192323-07-2 | AMRI Fine Chemicals catalog # A00096 | 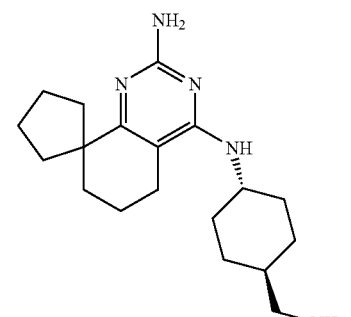 N4'-((1r,4r)-4-(aminomethyl)cyclohexyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| tert-Butyl trans-4-(2-aminoethyl)cyclohexylcarbamate | | AMRI Fine Chemicals catalog # A00049 | 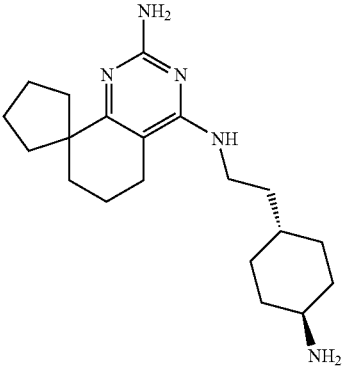<br>N4'-(2-((1r,4r)-4-aminocyclohexyl)ethyl)-6',7'-dihydro-5'H-spiro[cyclopentane-1,8'-quinazoline]-2',4'-diamine |
| 1,3-Cyclohexanebis(methylamine) | 2579-20-6 | Aldrich catalog # 180467 | 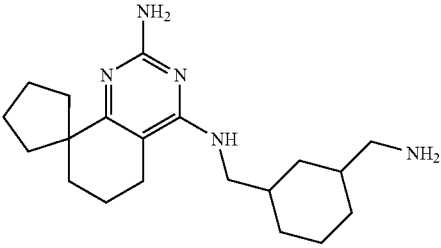<br>N4'-((3-(aminomethyl)cyclohexyl)methyl)-6',7'-dihydro-5'H-spiro[cyclopentane-1,8'-quinazoline]-2',4'-diamine |
| 1,4-Bis(aminomethyl)cyclohexane | 2549-93-1 | TCI-US catalog # B1083 | 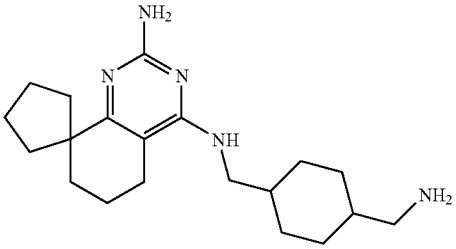<br>N4'-((4-(aminomethyl)cyclohexyl)methyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 1-(2-Aminoethyl) pyrrolidine | 7154-73-6 | Aldrich catalog # A55357 | N4'-(2-pyrrolidin-1-yl)ethyl)-6',7'-dihydro-5'H-spiro[cyclopentane-1,8'-quinazoline]-2',4'-diamine |
| 1-(3-Aminopropyl) pyrrolidine | 23159-07-1 | Acros catalog # 36809 | N4'-(3-(pyrrolidin-1-yl)propyl)-6',7'-dihydro-5'H-spiro[cyclopentane-1,8'-quinazoline]-2',4'-diamine |
| 1-(4-Aminobutyl) pyrrolidine | 24715-90-0 | Matrix catalog # 007650 | N4'-(4-(pyrrolidin-1-yl)butyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| Methyl-(3-piperidin-1-yl-propyl)-amine | 86010-41-5 | Matrix catalog # 018963 | 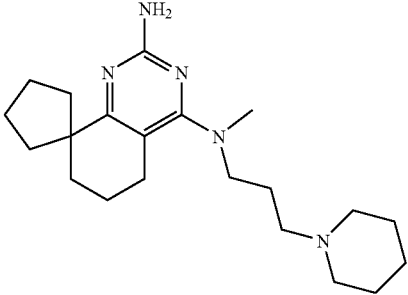<br>N4'-methyl-N4'-(3-(piperidin-1-yl)propyl)-6',7'-dihydro-5'H-spiro[cyclopentane-1,8'-quinazoline]-2',4'-diamine |
| Methyl-(2-piperidin-1-yl-ethyl)-amine | 41239-39-8 | Metrix catalog # 018964 | 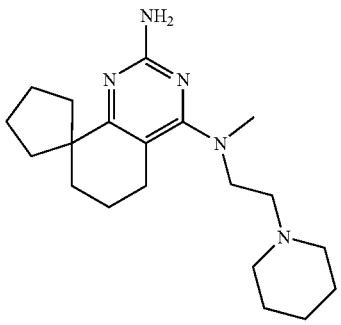<br>N4'-methyl-N4'-(2-(piperidin-1-yl)propyl)-6',7'-dihydro-5'H-spiro[cyclopentane-1,8'-quinazoline]-2',4'-diamine |
| 4,4'-Bipiperidine dihydrochloride | 78619-84-8 | Aldrich catalog # 180742 | 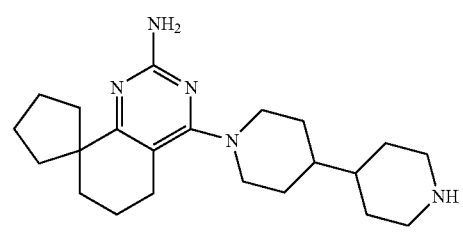<br>4'-(4,4'-bipiperidin-1-yl)-6',7'-dihydro-5'H-spiro[cyclopentane-1,8'-quinazoline]-2'-amine |
| 4,4'-Ethylene-dipiperidine dihydrochloride | 80997-86-0 | Aldrich catalog # 214140 | 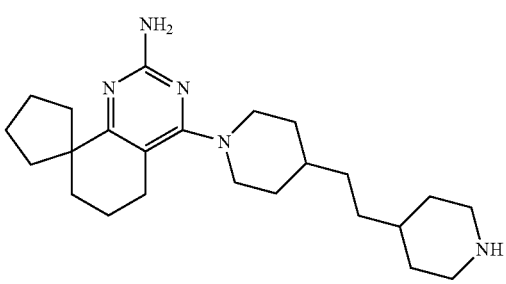<br>4'-(4-(2-piperidin-4-yl)ethyl)piperidin-1-yl)-6',7'-dihydro-5'H-spiro[cyclopentane-1,8'-quinazoline]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 2-(1-N-Boc-Aminomethyl-cyclohexyl)-ethylamine | 886362-17-0 | AstaTech Product List catalog # 46643 | 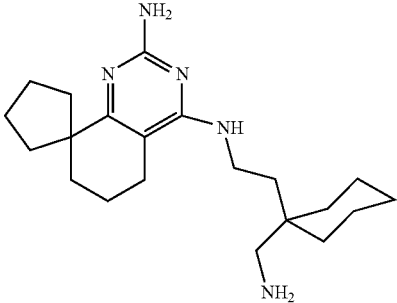 N4'-(2-(1-(aminomethyl)cyclohexyl)ethyl)-6',7'-dihydro-5'H-spiro[cyclopentane-1,8'-quinazoline]-2',4'-diamine |
| (1-Aminomethyl-cyclopentyl)-carbamic acid tert-butyl ester | 889949-09-1 | Tyger Scientific Product List catalog # A57914 | 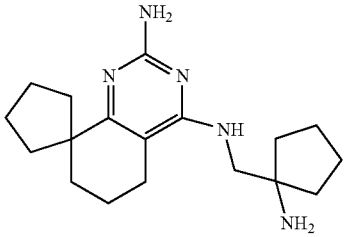 N4'-((1-(aminocyclopentyl)methyl)-6',7'-dihydro-5'H-spiro[cyclopentane-1,8'-quinazoline]-2',4'-diamine |
| 1-Pyrrolidin-1-ylmethyl-cyclohexylamine | 876717-44-1 | MATRIX catalog # 019232 | 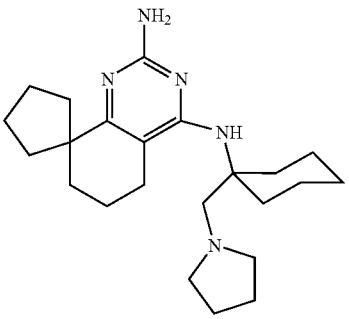 N4'-(1-(pyrrolidin-1-ylmethyl)cyclohexyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| cis-N-methyl-4-(1-pyrrolidinyl)-Cyclohexanamine, dihydrochloride | 883864-57-1 | WO2006040281 A1 | 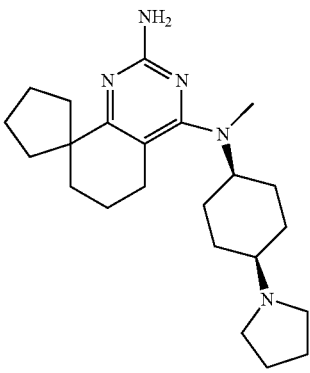<br>N4'-methyl-N4'-((1s,4s)-4-(pyrrolidin-1-yl)cyclohexyl)-6',7'-dihydro-5'H-spiro[cyclopentane-1,8'-quinazoline]-2',4'-diamine |
| trans-3-(1-Pyrrolidinyl)-cyclobutanamine | 878156-28-6 | WO2006021544 A1 | 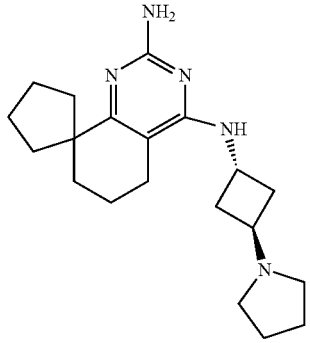<br>N4'-((1r,3r)-3-(pyrrolidin-1-yl)cyclobutyl)-6',7'-dihydro-5'H-spiro[cyclopentane-1,8'-quinazoline]-2',4'-diamine |
| trans-4-(1-Azetidinylmethyl)-cyclohexanamine | 878155-27-2 | WO2006021544 A1 | 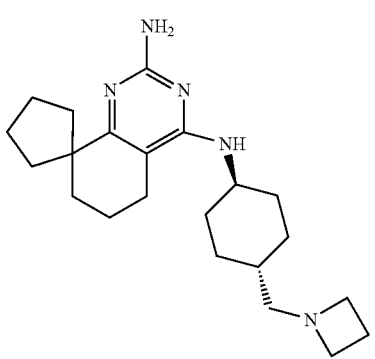<br>N4'-((1r,4r)-4-(azetidin-1-ylmethyl)cyclohexyl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| trans-4-(1-Pyrrolidinyl)-cyclohexanamine | 734527-26-5 | Chemstep Product List catalog # 43301 | 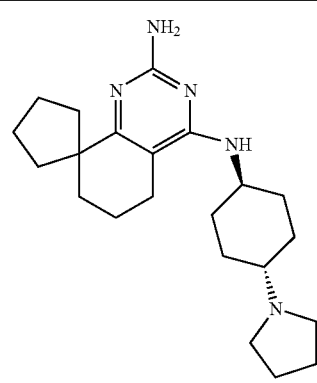<br>N4'-((1r,4r)-4-(pyrrolidin-1-yl)cyclohexyl)-6',7'-dihydro-5'H-spiro[cyclopentane-1,8'-quinazoline]-2',4'-diamine |
| 1-Methyl-4-(1-pyrrolidinyl)-cyclohexanamine, dihydrochloride | 412356-30-0 | WO2002030890 A1 | 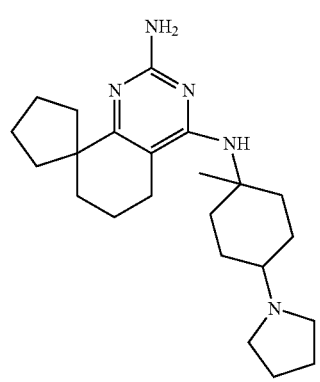<br>N4'-(1-methyl-4-(pyrrolidin-1-yl)cyclohexyl)-6',7'-dihydro-5'H-spiro[cyclopentane-1,8'-quinazoline]-2',4'-diamine |
| 4-amino-quinuclidine | 22766-61-6 | Prepared from 4-cyano-quinuclidine (CAS # 26458-78-6), Fluorochem, catalog # 017382. EP0202062A2 | 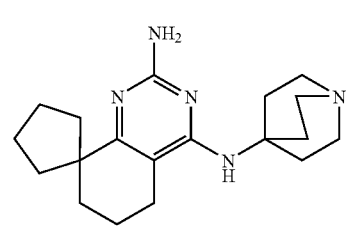<br>N4'-(quinuclidin-4-yl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 4-(aminomethyl)-quinuclidine | 67496-78-0 | Prepared from 4-cyano-quinuclidine (CAS # 26458-78-6), Fluorochem, catalog # 017382. WO99/21855 | N4'-(quinuclidin-4-ylmethyl)-6',7'-dihydro-5'H-spiro[cyclopentane-1,8'-quinazoline]-2',4'-diamine |
| (S)-(−)-3-amino-quinuclidine dihydrochloride | 119904-90-4 | Aldrich catalog # 415,723 | (R)-N4'-(quinuclidin-3-yl)-6',7'-dihydro-5'H-spiro[cyclopentane-1,8'-quinazoline]-2',4'-diamine |
| (R)-(+)-3-amino-quinuclidine dihydrochloride | 123536-14-1 | Aldrich catalog # 415,715 | (R)-N4'-(quinuclidin-3-yl)-6',7'-dihydro-5'H-spiro[cyclopentane-1,8'-quinazoline]-2',4'-diamine |
| 1-azatricyclo[3.3.1.1$^{3.7}$]decan-4r-amine | | Prepared from 1,4-cyclohexanedione monoethylene acetal (CAS # 4746-97-8), Aldrich catalog # 274879. Becker, D. P. and Flynn, D. L. Synthesis 1992, 1980-82 | N$^4$-(1-azatricyclo[3.3.1.13,7]decan-4r-yl)-6',7'-dihydro-5'H-spiro[cyclopentane-1,8'-quinazoline]-2',4'-diamine |
| 1-(2-hydroxyethyl)pyrrolidine | 2955-88-6 | ALDRICH catalog # H29404 | 4'(2-(pyrrolidin-1-yl)ethoxy)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| N-BOC-D-prolinol | 83435-58-9 | ALDRICH catalog # 469440 | 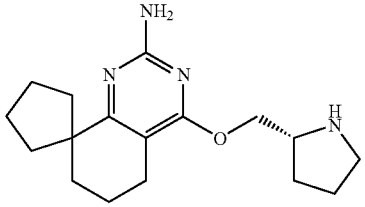<br>(R)-4'-(pyrrolidin-2-ylmethoxy)-6',7'-dihydro-5'H-spiro[cyclopentane-1,8'-quinazolin]-2'-amine |
| BOC-L-prolinol | 69610-40-8 | ALDRICH catalog # 446327 | 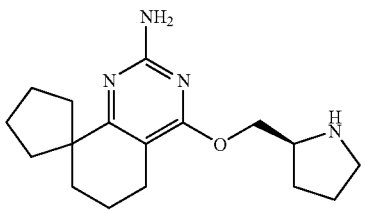<br>(S)-4'-(pyrrolidin-2-ylmethoxy)-6',7'-dihydro-5'H-spiro[cyclopentane-1,8'-quinazolin]-2'-amine |
| (R)-2-hydroxymethyl-piperidine-1-carboxylic acid tert-butyl ester | | CHEM-IMPEX catalog # 16141 | 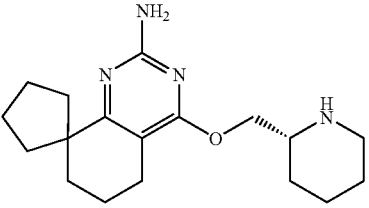<br>(R)-4'-(piperidin-2-ylmethoxy)-6',7'-dihydro-5'H-spiro[cyclopentane-1,8'-quinazolin]-2'-amine |
| BOC-S-PIP-2MEOH | | CHEM-IMPEX catalog # 16146 | 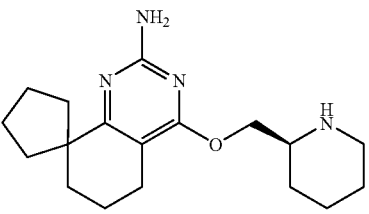<br>(S)-4'-(piperidin-2-ylmethoxy)-6',7'-dihydro-5'H-spiro[cyclopentane-1,8'-quinazolin]-2'-amine |
| 3-amino-cyclohexanol | 6850-39-1 | TYGER catalog # A58076 | 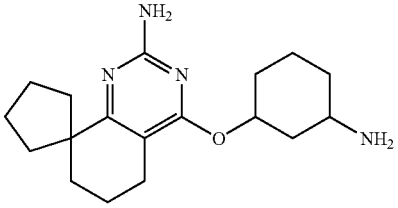<br>4'-(3-aminocyclohexyloxy)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| trans-4-aminocyclohexanol | 27489-62-9 | ALFA catalog # B22365 | 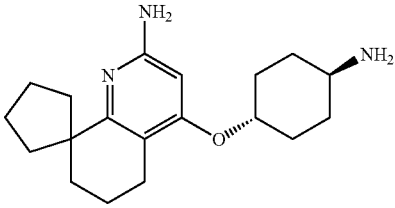 4'-((1r,4r)-4-aminocyclohexyloxy)-6',7'-dihydro-5'H-spiro[cyclopentane-1,8'-quinazolin]-2'-amine |
| tert-butyl cis-4-hydroxycyclo-hexylcarbamate | 167081-25-6 | AMRI catalog # A00071 | 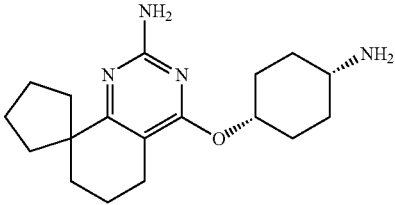 4'-((1s,4s)-4-aminocyclohexyloxy)-6',7'-dihydro-5'H-spiro[cyclopentane-1,8'-quinazolin]-2'-amine |
| (cis)-3-aminocyclobutanol | | ALLWEYS catalog # 11331 | 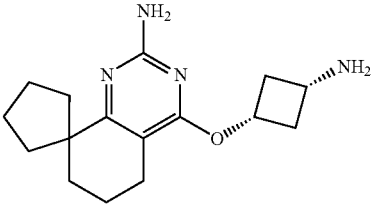 4'-((1s,3s)-4-aminocyclobutoxy)-6',7'-dihydro-5'H-spiro[cyclopentane-1,8'-quinazolin]-2'-amine |
| (trans)-3-aminocyclobutanol | 389890-42-0 | ALLWEYS catalog # 11361 | 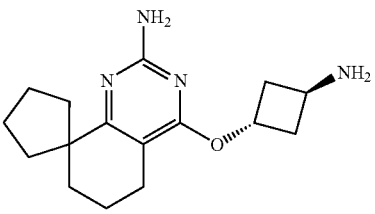 4'-((1r,3r)-3-aminocyclobutoxy)-6',7'-dihydro-5'H-spiro[cyclopentane-1,8'-quinazolin]-2'-amine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| N-((3R,4S)-4-methylpyrrolidine-3-yl)acetamide | | | 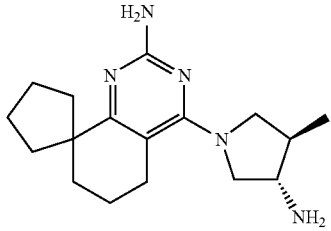 4'-((3S,4R)-3-amino-4-methylpyrrolidin-1-yl)-6',7'-dihydro-5'H-spiro[cyclopentane-1,8'-quinazolin]-2'-amine |
| (3S,4R)-1-benzyl-1-methyl-pyrrolidine-3-amine | | | 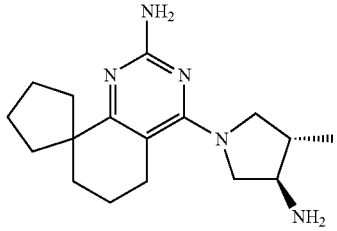 4'-((3R,4S)-3-amino-4-methylpyrrolidin-1-yl)-6',7'-dihydro-5'H-spiro[cyclopentane-1,8'-quinazolin]-2'-amine |
| (3S,4R)-1-benzyl-4-methyl-pyrrolidine-3-amine | | | 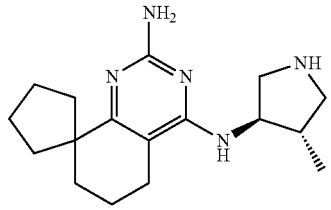 N4'-((3R,4S)-4-methylpyrrolidin-3-yl)-6',7'-dihydro-5'H-spiro[cyclopentane-1,8'-quinazolin]-2',4'-diamine |
| tert-butyl (3S,4R)-4-(trifluoromethyl)pyrrolidin-3-ylcarbamate | 168544-95-4 | Qun Li, et al., Bioorganic & Medicinal Chemistry Letters (1998), 8(15), 1953-1958. | 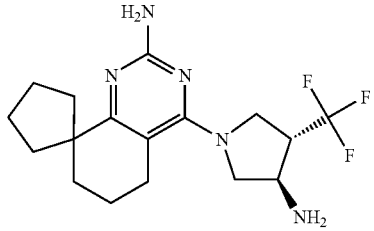 4'-((3R,4S)-3-amino-4-(trifluoromethyl)pyrrolidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| tert-butyl (3S,4R)-1-(trifluoromethyl)pyrrolidin-3-ylcarbamate | | | 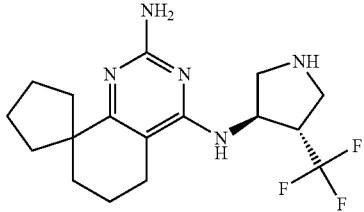<br>N4'-((3R,4S)-4-(trifluoromethyl)pyrrolidin-3-yl)-6',7'-dihydro-5'H-spiro[cyclopentane-1,8'-quinazoline]-2',4'-diamine |
| tert-butyl ((3S,4S)-4-(trifluoromethyl)pyrrolidin-3-yl)methylcarbamate | 168544-90-9 | Qun Li, et al, Bioorganic & Medicinal Chemistry Letters (1998), 8(15), 1953-1958. | 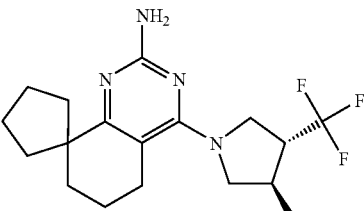<br>4'-((3S,4R)-3-(aminomethyl)-4-(trifluoromethyl)pyrrolidin-1-yl)-6',7'-dihydro-5'H-spiro[cyclopentane-1,8'-quinazolin]-2'-amine |
| tert-butyl ((3S,4S)-4-(trifluoromethyl)pyrrolidin-3-yl)methylcarbamate | | | 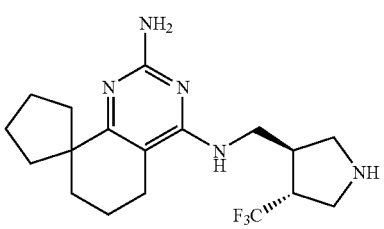<br>N4'-(((3R,4R)-4-(trifluoromethyl)pyrrolidin-3-yl)methyl)-6',7'-dihydro-5'H-spiro[cyclopentane-1,8'-quinazoline]-2',4'-diamine |
| tert-butyl (3S,5S)-5-methylpyrrolidin-3-ylcarbamate | 139161-75-4 | Qun Li, et al, Tetrahedron Letters (1995), 36(46), 8391-4 | 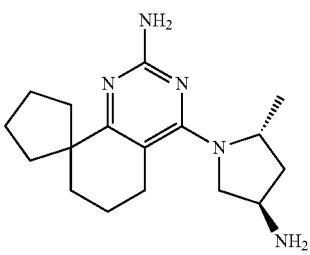<br>4'-((2R,4R)-4-amino-2-methylpyrrolidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| tert-butyl (3S,5S)-5-methylpyrrolidin-3-ylcarbamate | | | 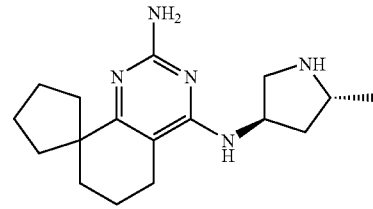<br>N4'-((3R,5R)-5-methylpyrrolidin-3-yl)-6',7'-dihydro-5'H-spiro[cyclopentane-1,8'-quinazoline]-2',4'-diamine |
| tert-butyl (3R,5S)-5-methylpyrrolidin-3-ylcarbamate | | | 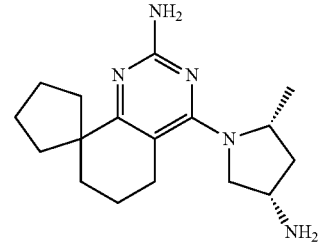<br>4'-((2R,4S)-4-amino-2-methylpyrrolidin-1-yl)-6',7'-dihydro-5'H-spiro[cyclopentane-1,8'-quinazolin]-2'-amine |
| tert-butyl (3R,5S)-5-methylpyrrolidin-3-ylcarbamate | | | 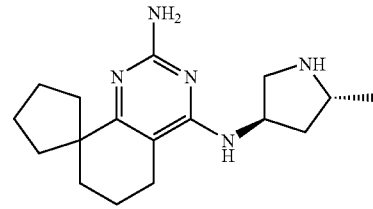<br>N4'-((3S,5R)-5-methylpyrrolidin-3-yl)-6',7'-dihydro-5'H-spiro[cyclopentane-1,8'-quinazoline]-2',4'-diamine |
| tert-butyl 1-benzyl-3-methylpyrrolidin-3-ylcarbamate | 181417-39-0 | T. Yoshida, et al, Chemical & Pharmaceutical Bulletin (1996), 44(7), 1376-1386. | 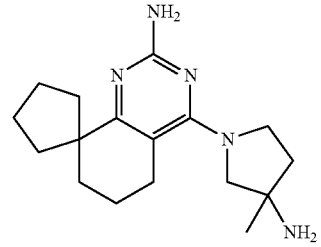<br>4'-(3-amino-3-methylpyrrolidin-1-yl)-6',7'-dihydro-5'H-spiro[cyclopentane-1,8'-quinazolin]-2'-amine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| tert-butyl 1-benzyl-3-methylpyrrolidin-3-ylcarbamate | | | 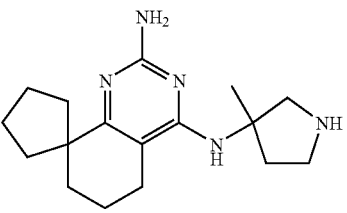<br>N4'-(3-methylpyrrolidin-3-yl)-6',7'-dihydro-5'H-spiro[cyclopentane-1,8'-quinazoline]-2',4'-diamine |
| (R)-benzyl 2-((tert-butoxycarbonylamino)methyl)pyrrolidine-1-carboxylate | 141774-69-8 | R. M. Burch, WO 9203415 A1 (1992) | 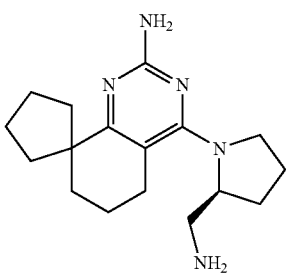<br>(S)-4'-(2-(aminomethyl)pyrrolidin-1-yl)-6',7'-dihydro-5'H-spiro[cyclopentane-1,8'-quinazolin]-2'-amine |
| (R)-benzyl 2-((tert-butoxycarbonylamino)methyl)pyrrolidine-1-carboxylate | | | 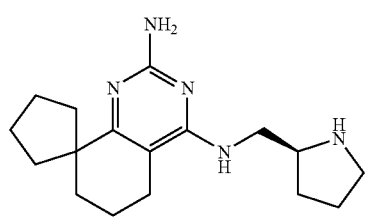<br>(S)-N4'-(pyrrolidin-2-ylmethyl)-6',7'-dihydro-5'H-spiro[cyclopentane-1,8'-quinazoline]-2',4'-diamine |
| tert-butyl (1-benzyl-pyrrolidin-3-yl)methylcarbamate | 155497-10-2 | Matrix 018167 | 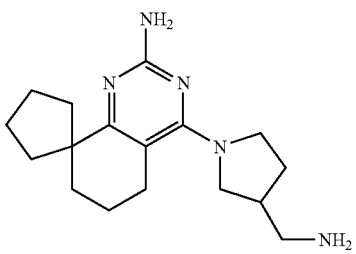<br>4'-(3-aminomethyl)pyrrolidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| tert-butyl (1-benzyl-pyrrolidin-3-yl)methylcarbamate | | | 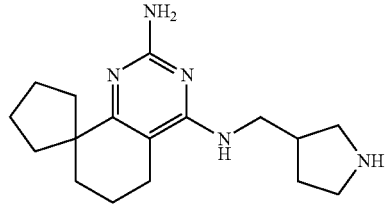<br>N4'-(pyrrolidin-3-ylmethyl)-6',7'-dihydro-5'H-spiro[cyclopentane-1,8'-quinazoline]-2',4'-diamine |
| N-((1-benzyl-pyrrolidin-3-yl)methyl)ethanamine | 91189-07-0 | Fulcrum B64503 | 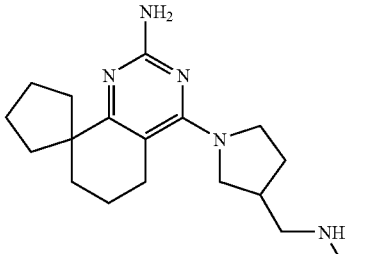<br>4'-(3-((ethylamino)methyl)pyrrolidin-1-yl)-6',7'-dihydro-5'H-spiro[cyclopentane-1,8'-quinazolin]-2'-amine |
| N-((1-benzyl-pyrrolidin-3-yl)methyl)ethanamine | | | 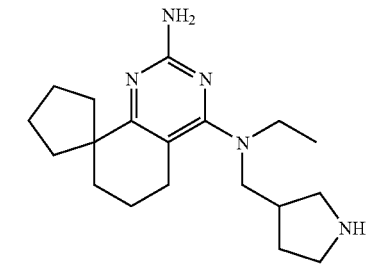<br>N4'-ethyl-N4'-(pyrrolidin-3-ylmethyl)-6',7'-dihydro-5'H-spiro[cyclopentane-1,8'-quinazoline]-2',4'-diamine |
| tert-butyl ethyl(((5S)-5-methylpyrrolidin-3-yl)methyl)carbamate | | | 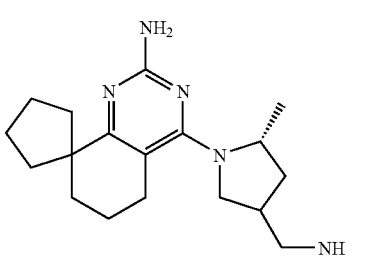<br>4'-((2R)-4-((ethylamino)methyl)-2-methylpyrrolidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| tert-butyl ethyl(((5S)-5-methylpyrrolidin-3-yl)methyl)carbamate | | | 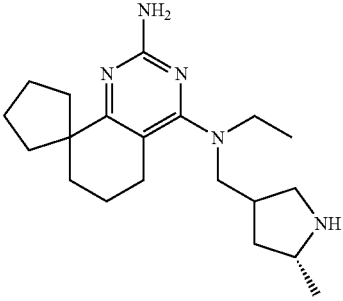<br>N4'-ethyl-N4'-(((5R)-5-methylpyrrolidin-3-yl)methyl)-6',7'-dihydro-5'H-spiro[cyclopentane-1,8'-quinazoline]-2',4'-diamine |
| (4S)-1-tert-butyl 3-methyl 4-aminopyrrolidine-1,3-dicarboxylate | 362491-96-1 | J. Duan, WO 2001070673 A2 (2001) | 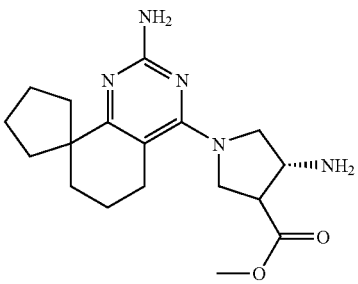<br>(4R)-methyl 4-amino-1-(2'-amino-6',7'-dihydro-5'H-spiro[cyclopentane-1,8'-quinazoline]-4'-yl)pyrrolidine-3-carboxylate |
| (4S)-1-tert-butyl 3-methyl 4-aminopyrrolidine-1,3-dicarboxylate | | | 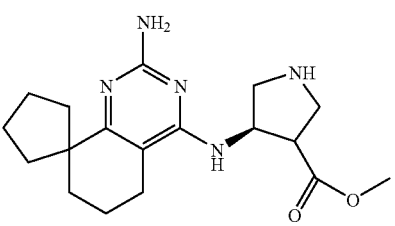<br>(4R)-methyl 4-(2'-amino-6',7'-dihydro-5'H-spiro[cyclopentane-1,8'-quinazoline]-4'-ylamino)pyrrolidine-3-carboxylate |
| 1-cyclopropylpiperazine | 139256-79-4 | Fulcrunm C-1450 | 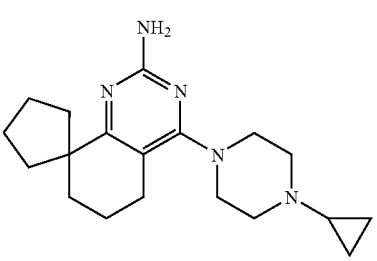<br>4'-(4-cyclopropylpiperazin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| 1,3-dimethylpiperazine | 22317-01-7 | G. Steiner, et al, Journal of Medicinal Chemistry (1986), 29(10), 1877-88. | 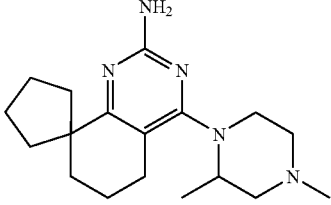<br>4'-(2,4-dimethylpiperazin-1-yl)-6',7'-dihydro-5'H-spiro[cyclopentane-1,8'-quinazolin]-2'-amine |
| 2-(azetidin-2-yl)ethanamine | 90324-66-6 | H. Taniyama, et al, Yakugaku Zasshi (1961), 81 1497-500 | 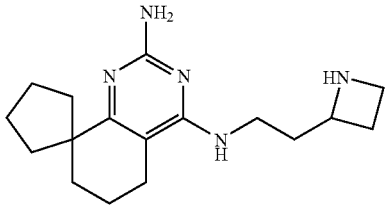<br>N4'-(2-(azetidin-2-yl)ethyl)-6',7'-dihydro-5'H-spiro[cyclopentane-1,8'-quinazoline]-2',4'-diamine |
| 2-(azetidin-2-yl)ethanamine | | | 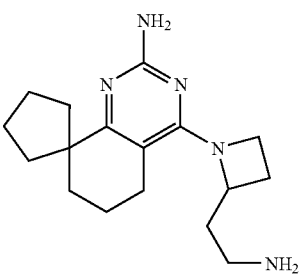<br>4'-(2-(2-aminoethyl)azetidin-1-yl)-6',7'-dihydro-5'H-spiro[cyclopentane-1,8'-quinazolin]-2'-amine |
| azetidin-2-ylmethanamine | 103550-76-1 | ABCHEM-INC AB1135 | 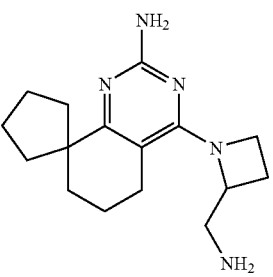<br>4'-(2-(2-aminomethyl)azetidin-1-yl)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| azetidin-2-ylmethanamine | | | 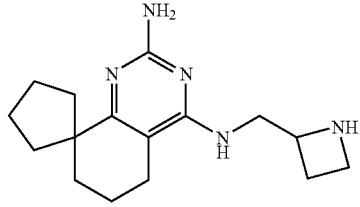<br>N4'-(azetidin-2-ylmethyl)-6',7'-dihydro-5'H-spiro[cyclopentane-1,8'-quinazoline]-2',4'-diamine |
| tert-butyl octahydro-1H-pyrrolo[3,4-b]pyridine-1-carboxylate | 159877-36-8 | Fulcrum B64519 | 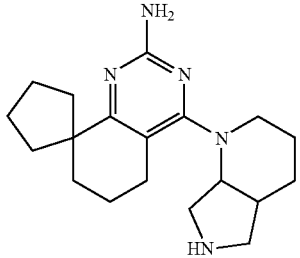<br>4'-(octahydro-1H-pyrrolo[3,4-b]pyridin-1-yl)-6',7'-dihydro-5'H-spiro[cyclopentane-1,8'-quinazolin]-2'-amine |
| tert-butyl (3aR,4R,7aS)-octahydro-1H-isoindol-4-ylcarbamate | 181141-44-6 | Qun Li, et al, Journal of Medicinal Chemistry (1996), 39(16), 3070-3088. | 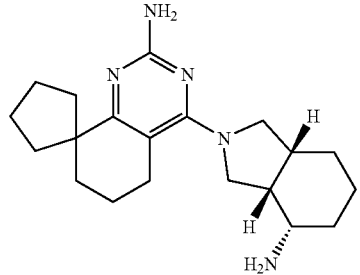<br>4'-((3aS,4S,7aR)-4-amino-1H-isoindol-2(3H,3aH,4H,5H,6H,7H,7aH)-yl)-6',7'-dihydro-5'H-6',7'-dihydro-5'H-spiro[cyclopentane-1,8'-quinazolin]-2'-amine |
| tert-butyl (3aR,4R,7aS)-octahydro-1H-isoindol-4-ylcarbamate | | | 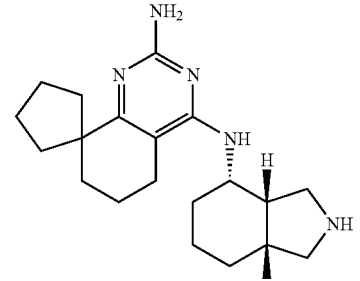<br>N4'-((3aS,4S,7aR)-octahydro-1H-isoindol-4-yl)-6',7'-dihydro-5'H-spiro[cyclopentane-1,8'-quinazoline]-2',4'-diamine |

TABLE 1-continued

Prospective Examples of synthetic intermediate groups, and Product Compounds
that may be prepared by the methods described in Schemes 1-13.

| Group | CAS # | Commercial Source or Literature, or Patent Reference | Product from group |
|---|---|---|---|
| tert-butyl (1R,5S)-3-azabicyclo[3.1.0]hexan-6-ylcarbamate | 134575-17-0 | G. Anquetin, et al, European Journal of Medicinal Chemistry (2006), 41(12), 1478-1493. | 4'-((1R,5S)-6-amino-3-azabicyclo[3.1.0]hexan-3-yl)-6',7'-dihydro-5'H-spiro[cyclopentane-1,8'-quinazolin]-2'-amine |
| tert-butyl (1R,5S)-3-azabicyclo[3.1.0]hexan-6-ylcarbamate | 134575-17-0 | G. Anquetin, et al, European Journal of Medicinal Chemistry (2006), 41(12), 1478-1493. | N4'-((1R,5S)-3-azabicyclo[3.1.0]hexan-6-yl)-6',7'-dihydro-5'H-spiro[cyclopentane-1,8'-quinazoline]-2',4'-diamine |
| tert-butyl (1R)-3-(1-phenylethyl)-3-azabicyclo[3.1.0]hexan-1-ylcarbamate | 182075-89-4 | M. Takemura, WO 9623782 A1 (1996) | 4'-((1S)-1-amino-3-azabicyclo[3.1.0]hexan-3-yl)-6',7'-dihydro-5'H-spiro[cyclopentane-1,8'-quinazolin]-2'-amine |
| tert-butyl (1R)-2-(1-phenylethyl)-3-azabicyclo[3.1.0]hexan-1-ylcarbamate | 182075-89-4 | M. Takemura, WO 9623782 A1 (1996) | N4'-((1S)-3-azabicyclo[3.1.0]hexan-1-yl)-6',7'-dihydro-5'H-spiro[cyclopentane-1,8'-quinazoline]-2',4'-diamine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| tert-butyl (1R)-3-(1-phenylethyl)-3-azabicyclo[3.1.0]hexan-1-ylcarbamate | 181941-43-5 | M. Takemura, WO 9623782 A1 (1996) | 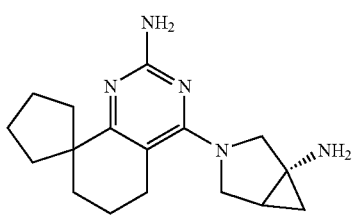<br>4'-((1R)-1-amino-3-azabicyclo[3.1.0]hexan-3-yl)-6',7'-dihydro-5'H-spiro[cyclopentane-1,8'-quinazolin]-2'-amine |
| tert-butyl (1R)-3-(1-phenylethyl)-3-azabicyclo[3.1.0]hexan-1-ylcarbamate | 181941-43-5 | M. Takemura, WO 9623782 A1 (1996) | 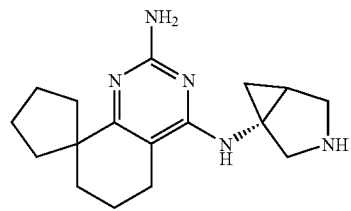<br>N4'-((1R)-3-azabicyclo[3.1.0]hexan-1-yl)-6',7'-dihydro-5'H-spiro[cyclopentane-1,8'-quinazoline]-2',4'-diamine |
| tert-butyl 3-hydroxypyrrolidine-1-carboxylate | 40499-83-0 | Aldrich P74354 | 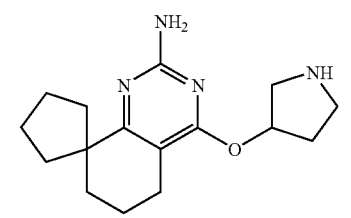<br>4'-(pyrrolidin-3-yloxy)-6',7'-dihydro-5'H-spiro[cyclopentane-1,8'-quinazolin]-2'-amine |
| (2S,4R)-tert-butyl-4-hydroxy-2-methylpyrrolidine-1-carboxylate | 114676-61-8 | Chu, Daniel T,; Li, Qun. U.S. Pat. No. 5,252,747 A (1993) | 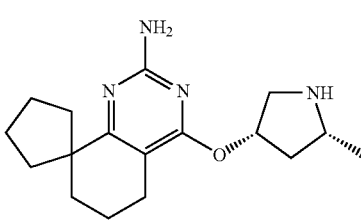<br>4'-((3S,5R)-5-methylpyrrolidin-3-yloxy)-6',7'-dihydro-5'H-spiro[cyclopentane-1,8'-quinazolin]-2'-amine |

TABLE 1-continued

Prospective Examples of synthetic intermediate groups, and Product Compounds that may be prepared by the methods described in Schemes 1-13.

| Group | CAS # | Commercial Source or Literature, or Patent Reference | Product from group |
|---|---|---|---|
| (3S,5S)-1-benzyl-5-methylpyrrolidin-3-ol | 152673-21-7 | Qun Li, et al, Tetrahedron Letters (1995), 36(46), 8391-4. | 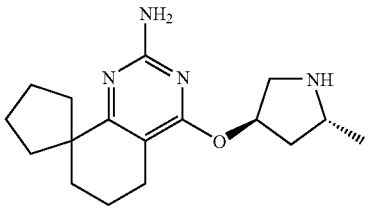<br>4'-((3R,5R)-5-methylpyrrolidin-3-yloxy)-6',7'-dihydro-5'H-spiro[cyclopentane-1,8'-quinazolin]-2'-amine |
| (R)-tert-butyl 2-(hydroxymethyl)azetidine-1-carboxylate | 161511-90-6 | TCI-US B2174 | 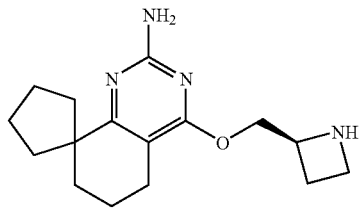<br>(S)-4'-(azetidin-2-ylmethoxy)-6',7'-dihydro-5'H-spiro[cyclopentane-1,8'-quinazolin]-2'-amine |

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral, intravenous, subcutaneous, intramuscular, intraperitoneal, intra-arterial, or intradermal injection, or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions; as well as other non-toxic compatible lubricants such as sodium lauryl sulfate and magnesium stearate. Coloring agents, releasing agents, coating agents, sweetening, flavoring and perfuming agents, preservatives, and antioxidants can also be present in the composition, according to the judgment of one skilled in the art of formulations.

The pharmaceutical compositions of this invention can be administered to humans and other mammals by oral administration or by injection, including by intravenous, subcutaneous, intramuscular, intraperitoneal, intra-arterial, and intradermal injection. The pharmaceutical compositions of this invention also can be administered to humans and other mammals topically (as by powders, lotions, ointments, or drops applied to the skin), bucally, or by inhalation, as an oral or nasal spray. The pharmaceutical compositions of this invention can be administered to humans and other mammals intrarectally or intravaginally. The term "parenterally," as used herein, refers to modes of administration which include intravenous, intramuscular, intraperitoneal, intrasternal, subcutaneous, and intraarticular.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents that delay absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, propionic, hydrobromic, glucuronic, methanesulfonic, ethanesulfonic, naphthalene sulfonic, lactic, fumaric, oxalic, and succinic acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound having a carboxylic acid moiety with an acid such as hydrochloric acid and an alcohol such methanol or ethanol.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl acid chloride. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

The compounds and processes of the invention will be better understood by reference to the following examples, which are intended as an illustration of and not a limitation upon the scope of the invention.

Unless otherwise described, reactions were carried out under ambient conditions (ranging 17-27° C.), under nitrogen. Unless otherwise described, column chromatography means flash chromatography carried out using silica gel, a technique well known to those of ordinary skill in the art of organic synthesis.

EXAMPLES

Example 1

(R)-4'-(3-(methylamino)pyrrolidin-1-yl)-6',7'-dihydro-5'H-spiro[cyclopentane-1,8'-quinazolin]-2'-amine Example 1A spiro[4.5]decan-6-one To a solution of bi(cyclopentane)-1,1'-diol (5.16 g, 29.4 mmol) in $CH_2Cl_2$ (80 mL), cooled to −20° C., was added trimethoxymethane (3.22 mL, 29.4 mmol), followed by boron trifluoride etherate (2.98 mL, 23.52 mmol). The cold bath was removed, and the reaction was stirred at ambient temperature for 2 hours. The mixture was then diluted with $CH_2Cl_2$ (100 mL), washed with saturated $NaHCO_3$, dried with $MgSO_4$, and concentrated under reduced pressure. The resulting residue was chromatographed on silica gel (100% hexane to 15:85 EtOAc/hexane, eluant) to provide the title compound. $^1H$ NMR (300 MHz, $CDCl_3$) δ 2.40 (t, 2H), 2.00-2.11 (m, 2 H), 1.78-1.87 (m, 2 H), 1.71 (t, 4H), 1.59 (t, 4H), 1.39 (t, 2 H). MS ($DCI^+$) m/z 153 (M+H).

Example 1B

Methyl 6-oxospiro[4.5]decane-7-carboxylate

A solution of diisopropylamine (5.97 mL, 41.9 mmol) in ether (30 mL) was cooled to −78° C. and then was treated slowly with n-butyllithium (16.75 mL, 41.9 mmol). The mixture was stirred at −78° C. for 30 minutes, then this solution was transferred via cannula into a −78° C. solution of Example 1A (4.25 g, 27.9 mmol) in ether (30 mL). The mixture was stirred at this temperature for 30 minutes and then was treated with dimethyl carbonate (23.50 mL, 279 mmol). The resulting mixture was warmed to ambient temperature and stirred for 16 hours. The mixture was quenched with saturated $NH_4Cl$ and diluted with ether (100 mL), then the layers were separated. The aqueous layer was extracted with additional ether, then the organic layers were combined, dried with $MgSO_4$, and concentrated under reduced pressure. The residue was chromatographed on silica gel (100% hexane to 85:15 EtOAc/hexanes, eluant) to provide the title product. $^1H$ NMR (300 MHz, $CDCl_3$) δ 12.40-12.42 (m, 1 H), 3.72-3.76 (m, 3 H), 2.18-2.26 (m, 2 H), 2.00-2.12 (m, 2 H), 1.74- 1.86 (m, 2 H), 1.57-1.62 (m, 2 H), 1.54-1.57 (m, 2 H), 1.35-1.48 (m, 4 H). MS (DCI+) m/z 211 (M+H).

Example 1C

2'-amino-6',7'-dihydro-5'H-spiro[cyclopentane-1,8'-quinazolin]-4'-ol

A solution of Example 1B (4.5 g, 21.4 mmol), guanidine hydrochloride (6.13 g, 64.2 mmol), and $K_2CO_3$ (9.46 g, 68.5 mmol) in DMF (30 mL) was heated at 105-110° C. for 3 hours. The mixture was then filtered through a layer of diatomaceous earth, and the filter pad was washed with a small amount of DMF. Approximately two volumes of water were then added, and the pH of the resulting mixture was adjusted to pH 6-7 with HOAc. The precipitate was collected, washed with $H_2O$, and dried under vacuum to provide the title product. $^1H$ NMR (300 MHz, DMSO-$d_6$) δ 10.50-10.61 (m, 1 H), 5.98-6.08 (m, 2 H), 2.20 (t, 2 H), 1.95-2.04 (m, 2 H), 1.68-1.76 (m, 2 H), 1.61-1.68 (m, 2 H), 1.48-1.58 (m, 4 H), 1.34-1.45 (m, 2 H). MS ($DCI^+$) m/z 220 (M+H).

Example 1D

2'-amino-6',7'-dihydro-5'H-spiro[cyclopentane-1,8'-quinazoline]-4'-yl 4-methylbenzenesulfonate A solution of Example 1C (2.91 g, 13.27 mmol), p-toluenesulfonyl chloride (3.79 g, 19.91 mmol), and DMAP (324 mg, 2.65 mmol) in $CH_2Cl_2$ (60 mL) was treated with TEA (3.7 ml, 4.40 mmol) at ambient temperature, and the resulting solution was stirred for 3 hours. It was then diluted with $CH_2Cl_2$ (100 mL) and $H_2O$ (50 mL), and the layers were separated. The organic layer was dried with $MgSO_4$ and concentrated under reduced pressure, then the residue was chromatographed on silica gel (1:2:2 EtOAc/$CH_2Cl_2$/hexane, eluant) to provide the title product (750 mg). $^1H$ NMR (300 MHz, $CD_3OD$) δ 7.95 (d, 2 H), 7.44 (d, 2 H), 2.45-2.47 (m, 3 H), 2.40-2.45 (m, 2 H), 1.99-2.10 (m, 2 H), 1.79-1.90 (m, 2 H), 1.65-1.75 (m, 6 H), 1.52-1.62 (m, 2 H). MS ($DCI^+$) m/z 374 (M+H).

Example 1E (1-Benzyl-(3R)-pyrrolidin-3-yl)-methyl-carbamic Acid tert-butyl Ester To a solution of (3R)-(−)-1-benzyl-3-(methylamino)pyrrolidine (200 mg, 1.05 mmol) and di-tert-butyl-dicarbonate (230 mg, 1.06 mmol) in MeOH (10 mL) was added NaOH (10%, 4 mL), and the mixture was stirred at ambient temperature for 1 hour. The mixture was diluted with $H_2O$ (20 mL) and EtOAc (100 mL). The organic layer was separated, and the aqueous layer was extracted with additional EtOAc. The combined organic layers were dried with $MgSO_4$, filtered, and concentrated under reduced pressure to provide the title compound. $^1H$ NMR (300 MHz, $CD_3OD$): δ 7.32 (m, 5H), 4.71 (m, 1H), 2.81 (s, 3H), 2.73 (m, 1H), 2.60 (dd, J=27 Hz, J=15 Hz, 2H), 2.53 (m, 2H), 2.07 (m, 1H), 1.80 (m, 1H), 1.43 (s, 9H). MS ($DCI^+$) m/z 291 (M+H).

Example 1F (R)-Methyl-pyrrolidin-3-yl-carbamic Acid tert-butyl Ester

To a solution of Example 1E (285 mg, 0.98 mmol) in 4.4% $HCO_2H$/MeOH (20 mL) under a nitrogen atmosphere was added Pd(OH)$_2$ on carbon (20%, 40 mg), and the resulting mixture was heated at 60° C. for 16 hours. The mixture was cooled to room temperature and filtered through a layer of diatomaceous earth, the filter pad was washed with extra MeOH (30 mL), and the filtrate was concentrated under reduced pressure. The residue was diluted with CH$_2$Cl$_2$ (30 mL) and washed with 1 M NaOH, then the organic solution was dried (MgSO$_4$), filtered, and concentrated under reduced pressure to provide the title compound. $^1$H NMR (300 MHz, CD$_3$OD) δ 4.57 (d, J=6 Hz, 1H), 3.03 (m, 2H), 2.87 (m, 1H), 2.79 (s, 3H), 2.76 (m, 1H), 1.99 (m, 1H), 1.79 (m, 1H), 1.46 (s, 9H). MS (DCI$^+$) m/z 201 (M+H).

Example 1G (R)-tert-butyl 1-(2'-amino-6',7'-dihydro-5'H-spiro [cyclopentane-1,8'-quinazoline]-4'-yl)pyrrolidin-3-yl (methyl)carbamate A microwave reaction vessel was charged with Example 1D (40 mg, 0.11 mmol), Example 1F (45 mg, 0.16 mmol), acetonitrile (3 mL), and triethylamine (0.1 mL), then the mixture was heated under microwave irradiation at 150° C. for 10 minutes. The mixture was cooled to ambient temperature and concentrated under reduced pressure, and the resulting residue was chromatographed on silica gel (100% EtOAc to 95-5 MeOH/EtOAc, eluant) to provide the title product.

Example 1H (R)-4'-(3-(methylamino)pyrrolidin-1-yl)-6',7'-dihydro-5'H-spiro[cyclopentane-1,8'-quinazolin]-2'-amine A solution of Example 1G (38 mg, 0.09 mmol) in CH$_2$Cl$_2$ (2 mL) was treated with trifluoroacetic acid (0.1 mL) at ambient temperature, and the reaction was stirred for 16 hours. The mixture was diluted with CH$_2$Cl$_2$ (20 mL) and washed with 1N NaOH and water. The organic layer was dried (MgSO$_4$) and concentrated under reduced pressure, and the resulting residue was chromatographed on silica gel (0.8:7.2:92 NH$_4$OH/MeOH/CH$_2$Cl$_2$, eluant) to provide the title product. $^1$H NMR (300 MHz, CD$_3$OD) δ 3.55-3.78 (m, 3 H), 3.37-3.44 (m, 1 H), 3.22 (t, 1 H), 2.57-2.65 (m, 2 H), 2.38-2.41 (m, 3 H), 2.02-2.17 (m, 3 H), 1.51-1.91 (m, 11 H). MS (DCI$^+$) m/z 302 (M+H).

Example 2

4'-(piperazin-1-yl)-6',7'-dihydro-5'H-spiro[cyclopentane-1,8'-quinazolin]-2'-amine A microwave reaction vessel was charged with Example 1D (35 mg, 0.094 mmol), piperazine (26 mg, 0.28 mmol), triethylamine (0.02 mL, 0.14 mmol), and acetonitrile (3 mL). The mixture was heated under microwave irradiation at 150° C. for 10 minutes. The mixture was then cooled to ambient temperature and concentrated under reduced pressure. The resulting residue was chromatographed on silica gel (0.8:7.2: 92 NH$_4$OH/MeOH/CH$_2$Cl$_2$, eluant) to provide the title product. $^1$H NMR (300 MHz, CD$_3$OD) δ 3.22 (t, 4 H), 2.90 (t, 4 H), 2.47 (t, 2 H), 2.03-2.14 (m, 2 H), 1.81-1.91 (m, 2 H), 1.52-1.81 (m, 8 H). MS (DCI$^+$) m/z 288 (M+H).

Example 3

4'-(3-(methylamino)azetidin-1-yl)-6',7'-dihydro-5'H-spiro[cyclopentane-1,8'-quinazolin]-2'-amine

Example 3A 1-benzhydryl-N-methylazetidin-3-amine

A solution of 1-benzhydryl-azetidin-3-ol (15 g, 62.7 mmol) in pyridine (60 mL) was chilled to 0° C., then treated with methanesulfonyl chloride (6.3 mL, 81 mmol). The reaction was warmed to room temperature and stirred for 3 hours. The mixture was partitioned between ether (300 mL) and H$_2$O (150 mL), and the ether layer was washed with H$_2$O and brine, dried (MgSO$_4$), and concentrated to provide the crude methanesulfonate. This crude methanesulfonate was taken up in DMF (60 mL) and treated with methyl amine (40% in H$_2$O, 90 mL), and the reaction was stirred at 85° C. for 48 hours. After cooling to room temperature, the mixture was partitioned between H$_2$O (200 mL) and EtOAc (400 mL). The aqueous layer was extracted with additional EtOAc, then the combined organics were extracted with 2N HCl (2×200 mL). The acidic aqueous extracts were combined, basified with 50% aqueous NaOH, and extracted with ether. Finally, these ethereal extracts were washed with brine, dried (MgSO$_4$), concentrated under reduced pressure, and purified by chromatography on silica gel (0.4:3.6:96 NH$_4$OH/MeOH/ CH$_2$Cl$_2$, eluant) to afford the title compound. $^1$H NMR (300 MHz, CDCl$_3$): δ 7.36-7.4 (m, 4H), 7.24-7.29 (m, 4H), 7.15-7.20 (m, 2H), 3.46 (t, J=6 Hz, 2H), 3.33 (m, 1H), 2.83 (t, J=6 Hz, 2H), 2.26 (s, 3H). MS (DCI$^+$) m/z 254 (M+H).

Example 3B tert-butyl azetidin-3-yl(methyl)carbamate

The title compound was prepared using the procedures of Examples 1E and 1F, substituting the product from Example 3A for (3R)-(−)-1-benzyl-3-(methylamino)pyrrolidine. $^1$H NMR (300 MHz, CDCl$_3$): δ 3.77 (t, J=6 Hz, 2H), 3.62 (t, J=6 Hz, 2H), 3.55 (m, 1H), 2.87 (s, 3H), 1.45 (s, 9H). MS (DCI$^+$) m/z 187 (M+H).

Example 3C

4'-(3-(methylamino)azetidin-1-yl)-6',7'-dihydro-5'H-spiro[cyclopentane-1,8'-quinazolin]-2'-amine The title compound was prepared using the procedures outlined in Examples 1G and 1H, substituting the product from Example 3B for the product from Example 1F. $^1$H NMR (300 MHz, CD$_3$OD) δ 4.35 (t, 2 H), 4.34 (t, 2 H), 3.50-3.60 (m, 1 H), 2.46 (t, 2 H), 2.32-2.34 (m, 3 H), 1.99-2.10 (m, 2 H), 1.51-1.89 (m, 10 H). MS (DCI$^+$) m/z 288 (M+H).

Example 4

(R)-4'-(3-aminopyrrolidin-1-yl)-6',7'-dihydro-5'H-spiro[cyclopentane-1,8'-quinazolin]-2'-amine The title compound was prepared using the procedures outlined in Examples 1G and 1H, substituting (R)-tert-butyl pyrrolidin-3-ylcarbamate for the product from Example 1F. $^1$H NMR (300 MHz, CDCl$_3$) δ 4.36-4.45 (m, 2 H), 3.67-3.78 (m, 2 H), 3.51-3.64 (m, 2 H), 3.27 (dd, 1 H), 2.53-2.60 (m, 2

H), 2.03-2.17 (m, 3 H), 1.78-1.91 (m, 2 H), 1.45-1.74 (m, 9 H). MS (DCI+) m/z 288 (M+H).

Example 5

(S)-4'-(3-aminopyrrolidin-1-yl)-6',7'-dihydro-5'H-spiro[cyclopentane-1,8'-quinazolin]-2'-amine The title compound was prepared using the procedures outlined in Examples 1G and 1H, substituting (S)-tert-butyl pyrrolidin-3-ylcarbamate for the product from Example 1F. $^1$H NMR (300 MHz, CD$_3$OD) δ 3.87-4.16 (m, 5 H), 2.69-2.76 (m, 2 H), 2.33-2.47 (m, 1 H), 2.09-2.22 (m, 1 H), 1.64-1.97 (m, 12 H). MS (DCI+) m/z 288 (M+H).

Example 6

4'-((3aR,6aR)-hexahydropyrrolo[3,4-b]pyrrol-1(2H)-yl)-6',7'-dihydro-5'H-spiro[cyclopentane-1,8'-quinazolin]-2'-amine Example 6A (3aR,6aR)-Hexahydro-pyrrolo[3,4-b]pyrrole-1,5-dicarboxylic Acid 5-benzyl Ester 1-tert-butyl Ester (3aR,6aR)-Hexahydro-pyrrolo[3,4-b]pyrrole-1-carboxylic acid tert-butyl ester (3.0 g, 12.5 mmol) and N-(benzyloxycarbonyloxy)-succinimide (3.42 g, 13.7 mmol) were mixed in 15 mL of dichloromethane. The mixture was stirred at room temperature overnight and then concentrated under vacuum to provide the crude product. The residue was purified by chromatography on silica gel (4:1 hexane-EtOAc, eluant) to provide the title compound. $^1$H NMR (CDCl3) δ 7.29-7.43 (m, 5 H), 5.13 (s, 2 H), 4.15-4.33 (m, 1 H), 3.39-3.74 (m, 5 H), 3.20-3.37 (m, 1 H), 2.84-2.96 (m, 1 H), 1.92-2.03 (m, 1 H), 1.66-1.82 (m, 1 H), 1.46 (s, 9 H). MS: (DCI+) m/z 347 (M+H).

The starting material (3aR,6aR)-hexahydro-pyrrolo[3,4-b]pyrrole-1-carboxylic acid tert-butyl ester (CAS # 370880-09-4) may be prepared as described in the literature, for example the method of Schenke, et al., "Preparation of 2,7-Diazabicyclo[3.3.0]octanes" U.S. Pat. No. 5,071,999 (1991) which provides a racemate which may be resolved by chromatography on a chiral column or by fractional crystallization of diastereomeric salts, or as described in Basha, et al. "Substituted diazabicycloalkane derivatives", US 2005101602 (2005).

Example 6B

4'-((3aR,6aR)-hexahydropyrrolo[3,4-b]pyrrol-1(2H)-yl)-6',7'-dihydro-5'H-spiro[cyclopentane-1,8'-quinazolin]-2'-amine The Boc group of Example 6A was removed as outlined in the procedure for Example 1H, substituting Example 6A for Example 1G. The resulting (3aR,6aR)-benzyl hexahydropyrrolo[3,4-b]pyrrole-5(1H)-carboxylate was reacted with the product from Example 1D according to the procedure of Example 1G, substituting (3aR,6aR)-benzyl hexahydropyrrolo[3,4-b]pyrrole-5(1H)-carboxylate for Example 1F. The product from this reaction (520 mg) was then heated at 50° C. under a H$_2$ atmosphere (60 psi) in the presence of 20% Pd(OH)$_2$ on charcoal. After cooling to room temperature, the hydrogen atmosphere was displaced with nitrogen, and the mixture was filtered through a layer of diatomaceous earth and concentrated under reduced pressure to provide the title compound. $^1$H NMR (300 MHz, CD$_3$OD) δ 4.70-4.77 (m, 1 H), 3.74-3.85 (m, 1 H), 3.50-3.59 (m, 1 H), 2.99-3.14 (m, 2 H), 2.72-2.89 (m, 3 H), 2.52-2.59 (m, 2 H), 2.16-2.28 (m, 1 H), 2.01-2.11 (m, 1 H), 1.63-1.97 (m, 9 H), 1.42-1.54 (m, 3 H). MS (DCI+) m/z 314 (M+H).

Example 7

4'-((3aS,6aS)-hexahydropyrrolo[3,4-b]pyrrol-1(2H)-yl)-6',7'-dihydro-5'H-spiro[cyclopentane-1,8'-quinazolin]-2'-amine The title compound was prepared using the procedures outlined in Examples 1G and 1H, substituting (3aS,6aS)-tert-butyl hexahydropyrrolo[3,4-b]pyrrole-5(1H)-carboxylate (CAS#: 370882-55-6, prepared according to the procedures in the patent US 2005101602) for the product from Example 1F. $^1$H NMR (300 MHz, CD$_3$OD) δ 4.73-4.80 (m, 1 H), 3.78-3.88 (m, 1 H), 3.52-3.61 (m, 1 H), 3.07-3.20 (m, 2 H), 2.78-2.93 (m, 3 H), 2.54-2.61 (m, 2 H), 2.15-2.27 (m, 1 H), 2.02-2.13 (m, 1 H), 1.63-1.96 (m, 9 H), 1.44-1.54 (m, 3 H). MS (DCI+) m/z 314 (M+H).

Example 8

4'-(1,4-diazepan-1-yl)-6',7'-dihydro-5'H-spiro[cyclopentane-1,8'-quinazolin]-2'-amine The title compound was prepared using the procedures outlined n Example 2, substituting homopiperazine for piperazine. $^1$H NMR (300 MHz, CDCl$_3$) δ 4.47-4.53 (m, 2 H), 3.58 (t, 4 H), 3.02 (t, 2 H), 2.91 (t, 2 H), 2.42-2.48 (m, 2 H), 2.06-2.17 (m, 2 H), 1.79-1.90 (m, 4 H) 1.63-1.72 (m, 6 H) 1.48-1.56 (m, 2 H). MS (DCI+) m/z 302 (M+H).

Example 9

4'-((4aR,7aR)-tetrahydro-1H-pyrrolo[3,4-b]pyridin-6(2H,7H,7aH)-yl)-6',7'-dihydro-5'H-spiro[cyclopentane-1,8'-quinazolin]-2'-amine The title compound was prepared using the procedures outlined in Examples 1G and 1H, substituting tert-butyl octahydro-1H-pyrrolo[3,4-b]pyridine-1-carboxylate (CAS# 159877-36-8) for the product from Example 1D. $^1$H NMR (300 MHz, CDCl$_3$) δ 4.38-4.47 (m, 2 H), 3.70-3.82 (m, 2 H), 3.38-3.52 (m, 2 H), 3.31 (td, 1 H), 3.00 (dt, 1 H), 2.57-2.69 (m, 3 H), 2.16-2.26 (m, 2 H), 1.96-2.07 (m, 1 H), 1.79-1.92 (m, 2 H), 1.64-1.76 (m, 6 H), 1.42-1.59 (m, 6 H). MS (DCI+) m/z 328 (M+H).

Example 10

N4'-(1-methylpiperidin-4-yl)-6',7'-dihydro-5'H-spiro[cyclopentane-1,8'-quinazoline]-2',4'-diamine The title compound was prepared using the procedures outlined in Example 2, substituting 1-methylpiperidin-4-amine for piperazine. $^1$H NMR (300 MHz, CDCl$_3$) δ 4.39-4.46 (m, 2 H), 4.14-4.21 (m, 1 H), 3.90-4.03 (m, 1 H), 2.72-2.82 (m, 2 H), 2.28-2.30 (m, 3 H), 2.19 (t, 2 H), 1.99-2.15 (m, 5 H), 1.81-1.90 (m, 2 H) 1.72-1.79 (m, 2 H), 1.64-1.71 (m, 2 H), 1.59-1.63 (m, 2 H), 1.43-1.54 (m, 4 H). MS (DCI+) m/z 316 (M+H).

Example 11

Methyl 4-amino-1-(2'-amino-6',7'-dihydro-5'H-spiro[cyclopentane-1,8'-quinazoline]-4'-yl)piperidine-4-carboxylate The title product was prepared using the procedures outlined in Examples 1G and 1H, substituting methyl 4-(tert-butoxycarbonylamino)piperidine-4-carboxylate (CAS# 115655-44-2) for the product from Example 1D. $^1$H NMR (300 MHz, CDCl$_3$) δ 4.50 (s, 2 H), 3.74 (s, 3 H), 3.30-3.36 (m, 4 H), 2.45 (t, J=4.58 Hz, 2 H), 2.04-2.21 (m, 4 H), 1.79-1.92 (m, J=4.07 Hz, 2 H), 1.49-1.73 (m, 10 H). MS (DCI$^+$) m/z 360 (M+H).

Example 12

4-amino-1-(2'-amino-6',7'-dihydro-5'H-spiro[cyclopentane-1,8'-quinazoline]-4'-yl)piperidine-4-carboxylic Acid A solution of the product from Example 11 (30 mg, 0.083 mmol) in MeOH (5 mL) was treated with NaOH solution (1 mL, 10%) and stirred for 16 hours. The mixture was concentrated under reduced pressure, and the resulting oil was chromatographed on silica gel (6:1:1 EtOAc/HCO$_2$H/H$_2$O, eluant). The fractions containing the still-impure product were combined and concentrated under reduced pressure, then the residue was again chromatographed on silica gel, this time eluting with NH$_4$OH/MeOH/CH$_2$Cl$_2$ (1.5:13.5:85), to provide the title product. $^1$H NMR (300 MHz, CD$_3$OD) δ 3.70-3.81 (m, 2 H), 3.45-3.57 (m, 2 H), 2.52 (t, J=5.43 Hz, 2 H), 2.25-2.36 (m, 2 H), 1.98-2.09 (m, 2 H), 1.76-1.94 (m, 6 H), 1.61-1.74 (m, 6 H). MS (DCI$^+$) m/z 346 (M+H) and 368 (M+Na).

Example 13

4'-(3-aminoazetidin-1-yl)-6',7'-dihydro-5'H-spiro[cyclopentane-1,8'-quinazolin]-2'-amine The title compound was prepared according to the procedures of Examples 1G and 1H, substituting tert-butyl azetidin-3-ylcarbamate for the product from Example 1D. $^1$H NMR (300 MHz, CDCl$_3$) δ 4.49 (br, 2H), 3.33 (m, 4H), 2.38-2.52 (m, 3H), 2.02-2.22 (m, 4H), 1.79-1.93 (m, 2H), 1.53-1.68 (m, 6H). MS (DCI$^+$) m/z 274 (M+H).

Example 14

4'-(2-(dimethylamino)ethoxy)-6',7'-dihydro-5'H-spiro[cyclopentane-1,8'-quinazolin]-2'-amine

Example 14A

4'-chloro-6',7'-dihydro-5'H-spiro[cyclopentane-1,8'-quinazolin]-2'-amine

To a solution of the product from Example 1D (300 mg, 0.803 mmol) in CH$_2$Cl$_2$ (10 mL) was added HCl in dioxane (0.6 mL, 4M), and the mixture stirred at ambient temperature for 16 hours. The mixture was concentrated under reduced pressure, and the resulting residue was chromatographed on silica gel, eluting with 5-20% EtOAc/hexane, to provide the title product. $^1$H NMR (300 MHz, CDCl$_3$) δ 4.79 (s, 2 H), 2.60 (t, J=6.35 Hz, 2 H), 2.02-2.13 (m, 2 H), 1.82-1.92 (m, 2 H), 1.63-1.79 (m, 6 H), 1.55-1.62 (m, 2 H). MS (DCI$^+$) m/z 357 (M+H).

Example 14B

4'-(2-(dimethylamino)ethoxy)-6',7'-dihydro-5'H-spiro[cyclopentane-1,8'-quinazolin]-2'-amine A solution of 2-(dimethylamino)ethanol (63.9 μL, 0.631 mmol) in THF (5 mL) was treated with potassium tert-butoxide (78 mg, 0.694 mmol) at 0° C., and the reaction mixture was stirred for 30 minutes at ambient temperature. It was then treated with a solution of the product from Example 14A (30 mg, 0.126 mmol) in THF (2 mL) at ambient temperature, and the whole was stirred for 2 hours. The mixture was diluted with CH$_2$Cl$_2$ (20 mL) and H$_2$O (10 mL), then the organic layer was separated, dried with MgSO$_4$, and concentrated under reduced pressure. The resulting residue was chromatographed on silica gel, eluting with NH$_4$OH/MeOH/CH$_2$Cl$_2$ (0.8/7.2/92), to afford the title product. $^1$H NMR (300 MHz, CDCl$_3$) δ 4.56 (s, 2 H), 4.37 (t, 2 H), 2.68 (t, J=5.93 Hz, 2 H), 2.43 (t, J=6.10 Hz, 2 H), 2.32 (s, 6 H), 2.01-2.13 (m, 2 H), 1.79-1.90 (m, 2 H), 1.59-1.74 (m, 6 H), 1.47-1.57 (m, 2 H). MS (DCI$^+$) m/z 291 (M+H).

Example 15

(R)-4'-(1-methylpyrrolidin-3-yloxy)-6',7'-dihydro-5'H-spiro[cyclopentane-1,8'-quinazolin]-2'-amine The title product was prepared using the procedures outlined in Example 14B, substituting (R)-1-methylpyrrolidin-3-ol for 2-(dimethylamino)ethanol. $^1$H NMR (300 MHz, CDCl$_3$) δ 4.54 (s, 2 H), 2.87 (dd, J=10.85, 6.44 Hz, 1 H), 2.73-2.80 (m, 1 H), 2.65-2.72 (m, 1 H), 2.39-2.48 (m, 3 H), 2.37 (s, 3 H), 2.24-2.35 (m, J=6.10 Hz, 1 H), 2.02-2.12 (m, 2 H), 1.90-2.00 (m, 1 H), 1.78-1.90 (m, 3 H), 1.59-1.73 (m, 6 H), 1.47-1.57 (m, 2 H). MS (DCI$^+$) m/z 303 (M+H).

Example 16

4-(piperazin-1-yl)-5,6,7,8-tetrahydrospiro[cyclohepta[d]pyrimidine-9,1'-cyclohexan]-2-amine

Example 16A spiro[5.6]dodecan-7-one

To a solution of cycloheptanone (2.1 mL, 17.83 mmol) and potassium tert-butoxide (2.60 g, 23.18 mmol) in THF (10 mL) was dropwise added a solution of 1-chloro-5-iodopentane (2.74 mL, 19.61 mmol) in THF (10 mL). The mixture was stirred at ambient temperature for 16 hours. It was then diluted with ether (200 mL), washed with saturated NH$_4$Cl and brine, dried with MgSO$_4$, and concentrated under reduced pressure. The resulting residue was chromatographed on silica gel (95:5 hexane-EtOAc, eluant) to provide the title compound. $^1$H NMR (300 MHz, CDCl$_3$) δ 2.50 (t, 2 H), 1.55-1.79 (m, 8 H), 1.30-1.52 (m, 10 H). MS (DCI$^+$) m/z 198 (M+H).

Example 16B

Methyl 7-oxospiro[5.6]dodecane-8-carboxylate

A solution of diisopropylamine (1.130 mL, 7.93 mmol) in THF (10 mL) was treated with n-butyllithium (3.17 mL, 7.93 mmol) at −78° C., and the reaction was stirred at this temperature for 30 minutes. The above solution was then transferred via cannula into a solution of the product from Example 16A (1.1 g, 6.10 mmol) in THF (10 mL) at −78° C., and the resulting mixture was stirred at this temperature for 30 minutes. Dimethyl carbonate (5.14 mL, 61.0 mmol) was added, the cold bath was removed, and HMPA (1.062 mL, 6.10 mmol) was then added. The resulting mixture was stirred at ambient temperature for 16 hours. It was quenched with HCl (1N) and diluted with ether (200 mL), then the organic layer was separated, washed with $H_2O$ and brine, dried with $MgSO_4$, and concentrated under reduced pressure. The residue was chromatographed on silica gel (95:5 hexane-EtOAc, eluant) to provide the title compound. $^1$H NMR (300 MHz, $CDCl_3$) δ 3.88 (dd, J=11.87, 3.05 Hz, 1 H), 3.68 (s, 3 H), 2.06-2.16 (m, 1 H), 1.92-2.04 (m, 2 H), 1.59-1.90 (m, 5 H), 1.29-1.51 (m, 8 H), 0.98-1.16 (m, 2 H). MS ($DCI^+$) m/z 239 (M+H).

Example 16C 2-amino-5,6,7,8-tetrahydrospiro[cyclohepta[d]pyrimidine-9,1'-cyclohexan]-4-ol A mixture of guanidine hydrochloride (430 mg, 4.5 mmol), the product from Example 16B (430 mg, 1.8 mmol), and potassium carbonate (623 mg, 4.5 mmol) in DMF (8 mL) was heated at 100° C. for 16 hours. Then, the temperature was raised to 120° C. for 2 hours. The mixture was cooled to ambient temperature and filtered through a layer of diatomaceous earth, then the filter pad was washed with a small amount of DMF. The filtrate was concentrated under reduced pressure, and the residue was chromatographed on silica gel (10:45:45 MeOH/$CH_2Cl_2$/EtOAc, eluant) to provide the title compound as a white solid. $^1$H NMR (300 MHz, DMSO-$d_6$) ppm 10.62 (s, 1 H), 6.04 (s, 2 H), 2.57-2.64 (m, 2 H), 1.93-2.05 (m, 2 H), 1.60-1.71 (m, 4 H), 1.35-1.57 (m, 9 H), 1.15-1.28 (m, 1 H). MS ($DCI^+$) m/z 248 (M+H).

Example 16D 2-amino-5,6,7,8-tetrahydrospiro[cyclohepta[d]pyrimidine-9,1'-cyclohexane]-4-yl 4-methylbenzenesulfonate The title compound was prepared using the procedures outlined in Example 1D, substituting the product from Example 16C for the product from Example 1C. $^1$H NMR (300 MHz, $CDCl_3$) δ 7.93 (d, J=8.48 Hz, 2 H), 7.34 (d, J=8.14 Hz, 1 H), 4.69 (s, 2 H), 2.70-2.77 (m, 2 H), 2.46 (s, 3 H), 1.89-2.02 (m, 2 H), 1.65-1.75 (m, 4 H), 1.41-1.64 (m, 10 H), 1.23-1.34 (m, 1 H). MS ($DCI^+$) m/z 402 (M+H).

Example 16E A-1047450.0

4-(piperazin-1-yl)-5,6,7,8-tetrahydrospiro[cyclohepta[d]pyrimidine-9,1'-cyclohexan]-2-amine The title compound was prepared using the procedures outlined in Example 2, substituting the product from Example 16D for the product from Example 1D. $^1$H NMR (300 MHz, $CDCl_3$) δ 4.52 (s, 2 H), 3.07-3.15 (m, 4 H), 2.93-2.98 (m, 4 H), 2.63-2.70 (m, 2 H), 2.01-2.16 (m, 2 H), 1.42-1.80 (m, 14 H). MS ($DCI^+$) m/z 316 (M+H).

Example 17

(R)-4-(3-aminopyrrolidin-1-yl)-5,6,7,8-tetrahydrospiro[cyclohepta[d]pyrimidine-9,1'-cyclohexan]-2-amine (R)-tert-butyl pyrrolidin-3-ylcarbamate (56 mg, 0.3 mmol), the product from Example 16D (60 mg, 0.15 mmol), and triethylamine (0.042 mL, 0.3 mmol) were placed in a 10 mL vial. The vial was capped, and the mixture was heated at 70° C. for 16 hours. It was then cooled to ambient temperature and concentrated under reduced pressure. The residue was chromatographed on silica gel, eluting with 97:3 EtOAc-MeOH, to provide the Boc-protected intermediate (35 mg). The intermediate was dissolved in $CH_2Cl_2$ (2 mL) and stirred with trifluoroacetic acid (0.1 mL) for 16 hours, then the mixture was basified with NaOH (10%) and diluted with $CH_2Cl_2$ (20 mL). The organic layer was separated, dried with $MgSO_4$, and concentrated under reduced pressure. The residue was chromatographed on silica gel (0.8:7.2:92 $NH_4OH$/MeOH/$CH_2Cl_2$, eluant) to afford the title compound. $^1$H NMR (300 MHz, $CDCl_3$) δ 4.51 (s, 2 H), 3.53-3.65 (m, 3 H), 3.42-3.52 (m, 1 H), 3.16 (dd, J=10.11, 4.56 Hz, 1 H), 2.57 (dd, J=6.74, 4.36 Hz, 2 H), 2.00-2.19 (m, 3 H), 1.36-1.85 (m, 15 H). MS ($DCI^+$) m/z 316 (M+H).

Example 18

4-((4aR,7aR)-tetrahydro-1H-pyrrolo[3,4-b]pyridin-6(2H,7H,7aH)-yl)-5,6,7,8-tetrahydrospiro[cyclohepta[d]pyrimidine-9,1'-cyclohexan]-2-amine The title compound was prepared using the procedures outlined in Example 17, substituting cis-tert-butyl octahydro-1H-pyrrolo[3,4-b]pyridine-1-carboxylate (CAS# 159877-36-8) for (R)-tert-butyl pyrrolidin-3-ylcarbamate. $^1$H NMR (300 MHz, $CDCl_3$) δ 4.40 (s, 2 H), 3.71-3.83 (m, 2 H), 3.30 (t, J=4.36 Hz, 2 H), 3.14-3.26 (m, 2 H), 2.98-3.06 (m, 1 H), 2.55-2.68 (m, 3 H), 2.13-2.26 (m, 2 H), 1.97-2.09 (m, 1 H), 1.66-1.82 (m, 8 H), 1.30-1.64 (m, 9 H). MS ($DCI^+$) m/z 356 (M+H).

Example 19

4-(piperazin-1-yl)-1',3',5,6,7,8-hexahydrospiro[cyclohepta[d]pyrimidine-9,2'-inden]-2-amine Example 19A 1',3'-dihydrospiro[cycloheptane-1,2'-inden]-2-one A solution of cycloheptanone (5.30 mL, 45.0 mmol) and 1,2-bis(bromomethyl)benzene (11.88 g, 45.0 mmol) in toluene (65 mL) was treated all at once with potassium tert-butoxide (10.10 g, 90 mmol). The reaction stirred for 20 hours at 85° C. After this time, the mixture was washed with 25 mL water and 65 mL of 15% HCl, then the aqueous washes were extracted three times with ether. The combined organics were washed with brine, dried over $Na_2SO_4$, and evaporated to a yellow oil, which was purified by chromatography on silica gel (93:7 to 85:15 EtOAc-hexane, eluant) to afford the title compound. $^1$H NMR (300 MHz, $d_6$-DMSO) δ 7.09-7.18 (m, 4H), 3.26 (d, J=16.0 Hz, 2H), 2.75 (d, J=16.0, 2H), 2.59 (m, 2H), 1.84 (m, 2H), 1.57-1.66 (m, 4H), 1.47 (m, 2H). MS ($DCI^+$) m/z 215 (M+H, 232 (M+$NH_4$).

Example 19B

Methyl 2-oxo-1',3'-dihydrospiro[cycloheptane-1,2'-inden]-3-carboxylate

A mixture of Example 19A (1.8 g, 8.40 mmol) in dimethyl carbonate (7.1 mL, 84 mmol) was treated with sodium hydride (60% dispersion in mineral oil, 0.672 g, 16.80 mmol) and a catalytic amount of MeOH (2 drops), then the mixture was heated at reflux. After 3 hours, the reaction was cooled to room temperature, and then it was quenched with 2N HCl. The mixture was extracted with ether, then the extracts were dried ($Na_2SO_4$) and evaporated. Purification by silica gel chromatography (10 to 25% EtOAc-hexane, eluant) afforded the title compound. $^1$H NMR (300 MHz, DMSO-$d_6$) δ 7.10-7.21 (m, 4H), 4.25 (dd, J=11.1, 2.8 Hz, 1H), 3.57 (s, 3H), 3.51 (d, J=15.9 Hz, 1H), 3.15 (d, J=15.9 Hz, 1H), 3.00 (m, 1H), 2.60 (d, J=16.3 Hz, 1H), 2.09 (m, 1H), 1.90 (d, J=5.2 Hz, 2H), 1.72-1.85 (m, 2H), 1.44-1.56 (m, 2H), 1.02-1.15 (m, 1H). MS ($DCI^+$) m/z 273 (M+H), 290 (M+$NH_4$).

Example 19C 2-amino-1',3',5,6,7,8-hexahydrospiro[cyclohepta[d]pyrimidine-9,2'-inden]-4-ol A mixture of Example 19B (490 mg, 1.799 mmol), guanidine nitrate (439 mg, 3.60 mmol), and potassium carbonate (497 mg, 3.60 mmol) in DMF (4 mL) was heated overnight at 120° C. After this time, the mixture was cooled to room temperature, then poured into 50 mL of water. The pH was adjusted to about 5 with acetic acid, then the precipitate was collected by filtration, washed with water, and air-dried. The sample was further dried azeotropically with toluene to yield the title compound. $^1$H NMR (300 MHz, DMSO-$d_6$) δ 10.70 (br, 1H), 7.07-7.20 (m, 4H), 6.14 (br s, 2H), 3.58 (d, J=16.0 Hz, 2H), 2.95 (m, 1H), 2.90 (m, 1H), 2.57-2.66 (m, 2H), 1.59-1.74 (m, 4H), 1.49 (m, 2H). MS ($DCI^+$) m/z 282 (M+H).

Example 19D 2-amino-1',3',5,6,7,8-hexahydrospiro[cyclohepta[d]pyrimidine-9,2'-inden]-4-yl 4-methylbenzenesulfonate Example 19C (0.395 g, 1.404 mmol), p-toluenesulfonyl chloride (0.535 g, 2.81 mmol), triethylamine (0.59 ml, 4.23 mmol), and DMAP (0.043 g, 0.351 mmol) were stirred in dichloromethane (23 ml) overnight at room temperature. The mixture was then diluted with $CH_2Cl_2$ and washed with water. The organics were dried over $Na_2SO_4$ and evaporated, then triturated with EtOAc to yield an orange-brown solution and a black tar. The solution was chromatographed on silica gel (15% EtOAc-hexane to 100% EtOAc, eluant) to yield the title compound. NMR (300 MHz, DMSO-$d_6$) δ 7.98 (d, J=8.3 Hz, 2H), 7.48 (d, J=7.9 Hz, 2H), 7.08-7.22 (m, 4H), 6.64 (br s, 2H), 3.56 (d, J=15.9 Hz, 2H), 3.04 (d, J=16.3 Hz, 2H), 2.61 (m, 2H), 2.43 (s, 3H), 1.75 (m, 2H), 1.57-1.70 (m, 2H), 1.47 (m, 2H). MS ($DCI^+$) m/z 436 (M+H).

Example 19E 4-(piperazin-1-yl)-1',3',5,6,7,8-hexahydrospiro[cyclohepta[d]pyrimidine-9,2'-inden]-2-amine Example 19D (0.191 g, 0.439 mmol), piperazine (0.050 g, 0.580 mmol), and triethylamine (0.13 mL, 0.933 mmol) were heated in 2-methoxyethanol (2.5 mL) at 115° C. overnight, then the mixture was evaporated in vacuo. Chromatography on silica gel (5 to 20% MeOH—$CH_2Cl_2$, eluant) afforded the p-toluenesulfonate salt of the title compound. $^1$H NMR (300 MHz, DMSO-$d_6$) δ 7.47 (d, J=7.93 Hz, 2H), 7.08-7.20 (m, 6H), 5.99 (br s, 2H), 3.59 (m, 2H), 2.96-3.18 (m, 11H), 2.62 (m, 2H), 2.29 (s, 3H), 1.65-1.80 (m, 4H), 1.50-1.62 (m, 2H). MS ($ESI^+$) 350 (M+H).

Example 20

(R)-4-(3-aminopyrrolidin-1-yl)-1',3',5,6,7,8-hexahydrospiro[cyclohepta[d]pyrimidine-9,2'-inden]-2-amine

Example 20A (R)-tert-butyl 1-(2-amino-1',3',5,6,7,8-hexahydrospiro[cyclohepta[d]pyrimidine-9,2'-inden]-4-yl)pyrrolidin-3-ylcarbamate The title compound was prepared according to the procedure of Example 19E, substituting (R)-tert-butyl pyrrolidin-3-ylcarbamate for piperazine. $^1$H NMR (300 MHz, DMSO-$d_6$) δ 7.08-7.18 (m, 4H), 6.10 (br, 2H), 5.65 (br s, 1H), 3.99 (m, 1H), 3.39-3.73 (m, 3H), 3.17-3.28 (m, 3H), 2.95 (m, 3H), 2.58 (m, 2H), 2.28 (m, 1H), 1.64-1.79 (m, 4H), 1.57 (m, 2H), 1.39 (s, 9H). MS ($ESI^+$) m/z 450 (M+H).

Example 20B (R)-4-(3-aminopyrrolidin-1-yl)-1',3',5,6,7,8-hexahydrospiro[cyclohepta[d]pyrimidine-9,2'-inden]-2-amine A solution of Example 20A (0.141 g, 0.314 mmol) in THF (10 mL) was treated with hydrogen chloride (4M in dioxane, 3.2 mL, 12.80 mmol), and the mixture was stirred for 2 hours at 60° C. The mixture was then evaporated, and the residue was triturated with EtOAc. The precipitate was collected by filtration and air-dried, then it was triturated again with $CH_2Cl_2$ to afford the dihydrochloride salt of the title compound. $^1$H NMR (300 MHz, DMSO-$d_6$) 8.22 (br, 2H), 7.21-7.27 (m, 4H), 3.88 (m, 2H), 3.47-3.80 (m, 3H), 2.86-3.22 (m, 3H), 2.58-2.85 (m, 2H), 1.96-2.37 (m, 3H), 1.91 (m, 1H), 1.46-1.85 (m, 5H). MS ($ESI^+$) m/z 350 (M+H).

Determination of Biological Activity

There are many methods available to show the effectiveness of compounds as histamine $H_4$ receptor ligands. Histamine $H_4$ receptors from mammalian species have been cloned. Methods to clone, express, and assess the potency and functional activity of such cloned genes are well known to those skilled in the art of molecular biology. Examples of methods of cloning and expressing histamine $H_4$ receptors, and of assessing the potency and functional activity, are described in Nguyen, et al. Molecular Pharmacology (2001) vol. 59 pp. 427-433; Zhu, et al. Molecular Pharmacology (2001) vol. 59 pp. 434-441; Coge, et al., Biochemical and Biophysical Research Communications (2001) vol. 284, pp. 301-309; Liu, et al. Molecular Pharmacology (2001) vol. 59 pp. 420-426; Liu, et al. Journal of Pharmacology and Experimental Therapeutics (2001) v. 299, pp. 121-130; and Thurmond, et al. Journal of Pharmacology and Experimental Therapeutics (2004) v. 309, pp. 404-413. In the present case, to determine the potency and effectiveness of representative compounds of this invention as histamine-$H_4$ receptor ligands ($H_4$ receptor ligands), the following tests were conducted according to previously described methods (see Esbenshade, et al., Biochemical Pharmacology (2004), vol. 68, pp. 933-945, and in Krueger, et al., Journal of Pharmacology and Experimental Therapeutics (2005) v. 314, pp. 271-281): histamine $H_4$ receptors were cloned and stably expressed in HEK-293 (human embryonic kidney) cells coexpressing a G$\alpha$qi5. Before testing, cells are loaded with a $Ca^{+2}$ sensitive fluorescent dye, in this case Fluo-4. In the case of partial agonist or agonist ligands, addition of compound to the cells leads to the increase in intracellular $Ca^{+2}$, which is detected by FLIPR (Fluorescence Imaging Plate Reader; Molecular Devices, Sunnyvale, Calif.) technology. In a similar manner, compounds that are antagonists or inverse agonists block the increase in fluorescence induced by the full histamine $H_4$ agonist histamine, and partial agonists reduce the amount of fluorescence induced by the full histamine $H_4$ agonist histamine. The fluorescence intensities measured before addition of the test compound are subtracted from the fluorescence intensities at later time points. Peak response values determined at each concentration of ligand are expressed as a percentage of the response obtained with the full agonist histamine. Concentration versus response data are analyzed to obtain compound potency as Kb values for antagonists and inverse agonists and as $EC_{50}$ values for partial agonists.

TABLE 2

In vitro histamine $H_4$ potency of compounds in FLIPR

| Example # | Potency (nM) |
|---|---|
| 1 | 2.9 |
| 2 | 2.8 |
| 3 | 4.6 |
| 4 | 2.7 |
| 5 | 53 |
| 6 | 1097 |
| 7 | 1027 |
| 8 | 9.8 |
| 9 | 8.5 |
| 10 | 22 |
| 11 | 12624 |
| 12 | 21251 |
| 13 | 68851 |
| 14 | 7.8 |
| 15 | 20 |
| 16 | 48 |
| 17 | 47 |
| 18 | 99 |
| 19 | 26915 |
| 20 | 499 |

Generally, representative compounds of the invention demonstrated potencies in the above FLIPR assay from about 1 nM to about 70000 nM. Preferred compounds of the invention have potencies at histamine-$H_4$ receptors from about 1 nM to about 100 nM. More preferred compounds of the invention have potencies at histamine $H_4$ receptors from about 1 nM to about 20 nM.

The potency of compounds of the invention in displacing $^3$H-histamine in competition binding assays is assessed by methods described in Esbenshade, et al., Biochemical Pharmacology (2004), vol. 68, pp. 933-945. In this assay, membranes were prepared from HEK-293 cells transiently transfected with the pCINeo expression vector harboring the histamine $H_4$ receptor by homogenization of the cells on ice in TE buffer (50 mM Tris-HCl buffer, pH 7.4, containing 5 mM EDTA), 1 mM benzamidine, 2 µg/ml aprotinin, 1 g/ml leupeptin, and 1 µg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer. Competition radioligand binding assays were performed with increasing concentrations of test compound in the presence of [$^3$H]-histamine incubated at 25° C. for 1 hour in a total volume of 0.5 mL of 50 mM Tris, 5 mM EDTA, pH 7.4. All binding reactions were terminated by filtration under vacuum onto polyethylenimine (0.3%) presoaked Unifilters (PerkinElmer Life Sciences) or Whatman GF/B filters (Whatman, Clifton, N.J.), followed by three brief washes with 4 ml of ice-cold TE buffer. Bound radiolabel was determined by liquid scintillation counting. For all of the radioligand competition binding assays, $IC_{50}$ values and Hill slopes were determined by Hill transformation of the data, and $K_i$ values were determined by the Cheng-Prusoff equation. The following table of representative histamine $H_4$ receptor ligands is provided, along with potency values:

| Compound Name (Example Number) | Potency (nM) |
|---|---|
| (R)-4'-(3-(methylamino)pyrrolidin-1-yl)-6',7'-dihydro-5'H-spiro[cyclopentane-1,8'-quinazolin]-2'-amine (1) | 2.6 |
| 4'-(piperazin-1-yl)-6',7'-dihydro-5'H-spiro[cyclopentane-1,8'-quinazolin]-2'-amine (2) | 1.1 |
| 4'-(3-(methylamino)azetidin-1-yl)-6',7'-dihydro-5'H-spiro[cyclopentane-1,8'-quinazolin]-2'-amine (3) | 1.4 |
| (R)-4'-(3-aminopyrrolidin-1-yl)-6',7'-dihydro-5'H-spiro[cyclopentane-1,8'-quinazolin]-2'-amine (4) | 4.6 |
| 4'-(1,4-diazepan-1-yl)-6',7'-dihydro-5'H-spiro[cyclopentane-1,8'-quinazolin]-2'-amine (8) | 2.8 |
| 4'-((4aR,7aR)-tetrahydro-1H-pyrrolo[3,4-b]pyridin-6(2H,7H,7aH)-yl)-6',7'-dihydro-5'H-spiro[cyclopentane-1,8'-quinazolin]-2'-amine (9) | 3.4 |
| 4-(piperazin-1-yl)-5,6,7,8-tetrahydrospiro[cyclohepta[d]pyrimidine-9,1'-cyclohexan]-2-amine (16) | 9.3 |
| (R)-4-(3-aminopyrrolidin-1-yl)-5,6,7,8-tetrahydrospiro[cyclohepta[d]pyrimidine-9,1'-cyclohexan]-2-amine (17) | 18 |

Generally, representative compounds of the invention demonstrate potencies from about 0.5 nM to about 20 nM. Preferred compounds of the invention have potencies at histamine-$H_4$ receptors from about 0.5 nM to about 10 nM. More preferred compounds of the invention have potencies at histamine $H_4$ receptors from about 0.5 nM to about 3 nM.

In addition to the utility of in vitro methods for characterizing the potency of compounds at the $H_4$ receptor, there are animal disease models available that demonstrate the utility of compounds. There are a number of methods to test the activity of compounds in different pain models that are well known to those skilled in the art. A description of the formalin test in rats, of neuropathic pain models in rats, and general descriptions of methods of testing and descriptions of pain models are found in the book 'Drug Discovery and Evaluation, $2^{nd}$ edition' (H. Gerhard Vogel, editor; Springer-Verlag, New York, 2002; pp. 702-706).

The usefulness of histamine $H_4$ receptor ligands in treating pain has been demonstrated (U.S. patent application Ser. No. 11/863,925;

also Coruzzi, et al, Eur. J. Pharmacol. 2007, Vol. 563, pp. 240-244). This invention discloses the novel utility of the compounds of the invention to treat pain, including multiple types of pain, including inflammatory pain, non-inflammatory pain, and neuropathic pain. Neuropathic pain is distinct from other types of pain (e.g. inflammatory pain) in that it can develop in response to previous or ongoing tissue injury, nerve injury, or diabetes, but it persists long after signs of the original injury or damage have disappeared. Neuropathic pain is not currently well treated, and therefore there is a strong need for methods to treat this particular type of pain. The topic of neuropathic pain has been reviewed in the scientific literature, for example, Smith, et al., Drug Development Research (2001) Vol. 54(3), pp. 140-153; Collins and Chessell, Expert Opinion on Emerging Drugs (2005) vol. 10(1), pp. 95-108; Vinik and Mehrabyan, Medical Clinics of North America (2004), vol. 88(4), pp. 947-999; Dray, Urban, and Dickenson, Trends in Pharmacological Sciences (1994) vol. 15(6) pp. 190-7; Dworkin, Clinical Journal of Pain (2002) vol. 18(6) pp. 343-9. There do exist a number of animal models of neuropathic pain that can be used to assess the ability of the compounds of the invention to treat neuropathic pain, as discussed herein.

Animal models of neuropathic pain are predictive of efficacy of treatment of neuropathic pain in humans. These models can be used to assess the efficacy of compounds of the invention in treating neuropathic pain. Examples of models well known to those skilled in the art include the Chung model (Kim and Chung, Pain (1992) vol. 50 pp. 355-363) and the Bennett model (Bennett and Xie, Pain (1988) vol. 30 pp. 87-107).

Determination of Analgesic Effect Against Neuropathic Pain

Animals are prepared for testing, by use of a surgical procedure that induces neuropathic pain in one paw. Male Sprague Dawley rats can be purchased from Charles River (Portage, Mich.). Prior to surgery, animals are housed in groups and maintained in a temperature-regulated environment. Following nerve ligation surgery, animals are housed in groups and have access to food and water ad libitum.

The L5 and L6 spinal nerves of anesthetized rats are tightly ligated in a manner described previously (see Kim and Chung, Pain (1992) vol. 50 pp. 355-363). An incision is made on the dorsal portion of the hip, and the muscle is blunt-dissected to reveal the spinal processes. The L6 transverse process is removed, and the left side L5 and L6 spinal nerves are tightly ligated with 5.0 braided silk suture. The wound is cleaned, the membrane sewn with 4.0 dissolvable Vicryl suture, and the skin closed with wound clips. The paw affected by the surgical procedure (the left paw) develops an allodynic response, a hypersensitivity to mechanical and other stimuli; neuropathic pain is assessed as an increased sensitivity in the surgically affected (left) allodynic paw compared to the control paw on the right side, and measured by comparing the response of the (left side) allodynic paw to the response of the unaffected right side control paw.

For the assessment of neuropathic pain, mechanical allodynia in the affected paw of animals that had undergone spinal nerve ligation can be evaluated using testing with von Frey filaments. As described previously by S. R. Chaplan, et al. ("Quantitative assessment of tactile allodynia in the rat paw" J. Neurosci. Meth. (1994) vol. 53 pp. 55-63), two weeks following surgery rats are acclimated to a testing box constructed of plexiglass with a wire mesh floor which allows access to the plantar surface of the animal's hindpaws. Using an Up-Down method (Dixon, Ann. Rev. Pharmacol. Toxicol. (1980) vol. 20, pp. 441-462; Chaplan et al., "Quantitative assessment of tactile allodynia in the rat paw" J. Neuroscience Methods (1994) vol. 53 pp. 55-63), von Frey filaments of increasing stiffness are applied to the plantar surface of the hindpaws, and the withdrawal response of the animals is observed; for the surgically affected paw with neuropathic pain (the left side paw), the baseline level of allodynia has a withdrawal threshold of $\leq 4$ g of pressure. By comparison, for the control paw without allodynia (in this case, the right side paw), the typical withdrawal pressure is around 15 g. The efficacy of the compound in reducing neuropathic pain at different doses is determined by comparing response in the surgery-affected paw versus the response in the control paw. This is expressed as the MPE (maximum percent effect), or 100 times the withdrawal threshold of the allodynic (left side) divided by the withdrawal threshold of the control (right side).

Determination of Analgesic Effect Against Inflammatory Pain

To assess the effectiveness of representative compounds of the invention against acute model inflammatory pain, animals can be tested in an acute model of carrageenan-induced thermal hyperalgesia (see for example, Honore, et al. Behavioural Brain Research 167 (2006) pp. 355-364; Porreca, et al., Journal of Pharmacology and Experimental Therapeutics (2006) vol. 318 pp. 195-205). Carrageenan is injected into the test paw of the animal, and after 90 minutes, the test drug is administered by intraperitoneal dosing; the effect on thermal hyperalgesia is assessed in a hotbox assay which is done 30 minutes after the intraperitoneal dosing of the test drug. The MPE (maximal percent effect) is reported by comparison to the control paw (not injected with carrageenan), MPE being expressed as 100 times the withdrawal latency of the carrageenan injected paw (in seconds) divided by the withdrawal latency of the control (not injected with carrageenan) paw.

Determination of Analgesic Effect Against Pain in a Surgical Skin Incision Model Analgesic effect against pain can also be determined using a surgical skin incision model (Joshi, et al., Pain 123 (2006) 75-82). Under sterile conditions, animals (rats) are prepared for testing by subjecting them to a surgical procedure, where the plantaris muscle is elevated and incised longitudinally with the origin and insertion of the muscle remaining intact. The skin is then closed with two mattress sutures (e.g. 5-0 nylon sutures). After surgery, animals are allowed to recover on a warming plate and are housed individually in cages with soft bedding. After this surgery, the animals develop a hypersensitivity called allodynia (that is, pain due to a stimulus that does not normally provoke pain). Animals can be tested for mechanical allodynia using von Frey hair mechanical stimulation 2, 24, and 48 hours after surgery as described for the Chung model.

Compounds of the invention are histamine $H_4$ receptor ligands that modulate function of the histamine $H_4$ receptor by altering the activity of the receptor. These compounds may be antagonists that block the action of receptor activation induced by histamine $H_4$ receptor agonists such as histamine; they may be histamine $H_4$ receptor inverse agonists that inhibit the basal activity of the receptor and block the action of receptor activation induced by histamine $H_4$ receptor agonists such as histamine; and they may be partial agonists that partially block the action of receptor activation induced by histamine H$_4$ receptor agonists such as histamine and prevent full activation of histamine H$_4$ receptors.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

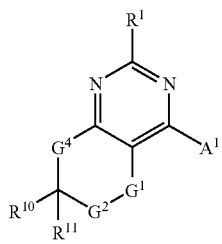

or a pharmaceutically acceptable salt thereof, wherein:
G$^1$ is CH$_2$CH$_2$;
G$^2$ is CH$_2$;
wherein each carbon of G$^1$ and G$^2$ may be optionally substituted with one or more groups selected from acyl, acyloxy, alkenyl, alkoxy, alkoxyalkyl, alkoxyalkoxy, alkoxycarbonyl, alkyl, alkylcarbonyl, alkylcycloalkyl, alkylsulfonyl, alkylthio, alkynyl, amido, carboxy, cyano, cyanoalkyl, cycloalkoxyalkyl, cycloalkyl, fluoroalkoxy, fluoroalkyl, fluorocycloalkyl, fluorocycloalkylalkyl, formyl, haloalkoxy, haloalkyl, halogen, hydroxy, hydroxyalkyl, mercapto, nitro, and oxo;
G$^4$ is a bond;
R$^1$ is selected from hydrogen, NH$_2$, —NH(acyl), —NH(alkyl), —N(alkyl)$_2$, —NH(C=O)aryl, —NH-alkylene (NR$^8$R$^9$), —NH(C=O)-alkylene(NR$^8$R$^9$), —NR$^8$(C=O)NR$^8$R$^9$, —NH-alkylene-heteroaryl, —NHOH, —NHOCH$_3$, —O-alkylene(NR$^8$R$^9$), alkoxy, alkoxycarbonyl, alkyl, carboxy, —(C=O)—(NR$^8$R$^9$), —(C=O)—NH-alkylene(NR$^8$R$^9$), cyano, cyanoalkyl, cycloalkyl, fluoroalkyl, fluorocycloalkyl, hydroxyalkyl, and piperazinyl;

R$^8$ and R$^9$ each are each independently selected from acyl, alkoxyalkyl, alkoxycarbonyl, alkyl, alkylcarbonyl, alkylcycloalkyl, alkylsulfonyl, amido, aryl, cyanoalkyl, cycloalkoxyalkyl, cycloalkyl, fluorocycloalkyl, fluorocycloalkylalkyl, heteroaryl, heterocyclyl, hydrogen, formyl, hydroxy, and hydroxyalkyl;
R$^{10}$ and R$^{11}$ taken together are alkylene, —OCH$_2$CH$_2$O—, —OCH$_2$CH$_2$CH$_2$O—, or —CH$_2$CH$_2$OCH$_2$CH$_2$—,
A$^1$ is

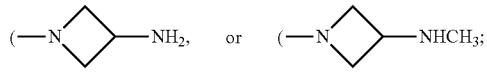

and
wherein each carbon atom of groups A$^1$ may be optionally substituted with one or more groups selected from acyl, acyloxy, alkenyl, alkoxy, alkoxyalkoxy, alkoxyalkyl, alkoxycarbonyl, alkyl, alkylcarbonyl, alkylcycloalkyl, alkylsulfonyl, alkylthio, alkynyl, amido, carboxy, cyano, cyanoalkyl, cycloalkoxyalkyl, cycloalkyl, fluoroalkoxy, fluoroalkyl, fluorocycloalkyl, fluorocycloalkylalkyl, formyl, haloalkoxy, haloalkyl, halogen, hydroxy, hydroxyalkyl, mercapto, and nitro.

2. The compound of claim 1, wherein R$^1$ is selected from hydrogen, NHOH, —NHOCH$_3$, alkoxy, cyano, cyanoalkyl, cycloalkyl, fluoroalkyl, fluorocycloalkyl, and hydroxyalkyl.

3. The compound of claim 1, wherein R$^1$ is hydrogen, NH$_2$, —NHCH$_3$, —NH(C=O)CH$_3$, —NH(C=O)phenyl, —NH(C=O)NHCH$_3$, —NH(C=O)CH$_2$NH$_2$, —NH(C=O)CH$_2$NHCH$_3$, —NH(C=O)CH$_2$N(CH$_3$)$_2$, —NH(C=O)CH$_2$CH$_2$CH$_2$NH$_2$, —NHCH$_2$(pyridin-3-yl), —NHCH$_2$(imidazol-4-yl), —NHCH$_2$CH$_2$N(CH$_3$)$_2$, piperazin-1-yl, —(C=O)OCH$_3$, or —(C=O)OH.

4. The compound of claim 1, wherein R$^{10}$ and R$^{11}$ taken together are —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —OCH$_2$CH$_2$O—, —OCH$_2$CH$_2$CH$_2$O—, or —CH$_2$CH$_2$OCH$_2$CH$_2$.

5. The compound of claim 1, wherein the compound is selected form the group consisting of:
4'-(3-(methylamino)azetidin-1-yl)-6',7'-dihydro-5'H-spiro[cyclopentane-1,8'-quinazolin]-2'-amine; and
4'-(3-aminoazetidin-1-yl)-6',7'-dihydro-5'H-spiro[cyclopentane-1,8'-quinazolin]-2'-amine.

6. A pharmaceutical composition comprising a compound of claim 1 and a pharmaceutically acceptable carrier.

* * * * *